US009127233B2

(12) United States Patent
Dietz

(10) Patent No.: US 9,127,233 B2
(45) Date of Patent: Sep. 8, 2015

(54) DEVICE AND METHOD FOR SOLUBILIZING, SEPARATING, REMOVING AND REACTING CARBOXYLIC ACIDS IN OILS, FATS, AQUEOUS OR ORGANIC SOLUTIONS BY MEANS OF MICRO-OR NANOEMULSIFICATION

(75) Inventor: Ulrich Dietz, Wiesbaden (DE)

(73) Assignee: Ulrich Dietz, Wiesbaden (DE)

( * ) Notice: Subject to any disclaimer, the term of this patent is extended or adjusted under 35 U.S.C. 154(b) by 256 days.

(21) Appl. No.: 13/805,492

(22) PCT Filed: Jun. 22, 2011

(86) PCT No.: PCT/EP2011/003182
§ 371 (c)(1),
(2), (4) Date: Dec. 19, 2012

(87) PCT Pub. No.: WO2011/160857
PCT Pub. Date: Dec. 29, 2011

(65) Prior Publication Data
US 2013/0090488 A1      Apr. 11, 2013

Related U.S. Application Data

(60) Provisional application No. 61/344,311, filed on Jun. 28, 2010.

(30) Foreign Application Priority Data

Jun. 22, 2010   (EP) ..................................... 10075274

(51) Int. Cl.
*C11B 13/00*   (2006.01)
*C11B 3/04*    (2006.01)
*C07B 63/04*   (2006.01)

(52) U.S. Cl.
CPC .. *C11B 3/04* (2013.01); *C07B 63/04* (2013.01)

(58) Field of Classification Search
CPC .......... C11B 3/03; C11B 3/001; C11B 3/006; C11B 3/10; C11B 3/14
USPC ......................................................... 554/184
See application file for complete search history.

(56) References Cited

PUBLICATIONS

Ayako Hirai et al: "Ellects of I-arginine on aggregates of fatty-acid/potassium soap in the aqueous media", Colloid and Polymer Science; Kolloid-Zeitschrift Und Zeitschrift Fur Polymere, vol. 284, No. 5, Feb. 1, 2006, pp. 520-528.*

(Continued)

*Primary Examiner* — Deborah D Carr
(74) *Attorney, Agent, or Firm* — Amin, Turocy & Watson, LLP

(57) ABSTRACT

The present invention is directed to solubilizing compounds, a device and a method for solubilizing and removing carboxylic acids and especially fatty acids from oils, fats, aqueous emulsion, aqueous media and organic solutions. Devices utilizing the inventive method shall be used for separating carboxylic acids from oils, fats, aqueous emulsion, lipophilic media or organic solutions, respectively by preparing an aqueous micro- or nanoemulsion of the carboxylic acids especially the fatty acids and the solubilizing compound which contains at least one amidino and/or gianidino group. Solubilization effects of solubilizing compounds combined with the inventive use of separation methods for carboxylic acids can be used to treat persons in need of removal of fatty acids or analyze carboxylic acids from blood or process other solutions in food, pharmacy, chemistry, bio fuel industry or other industrial processings.

12 Claims, 7 Drawing Sheets

(56) References Cited

PUBLICATIONS

Masako Koyama: "Effect of Arginine as a Counterion on Surfactant Properties of Fatty Acid Salts", Journal of Dispersion Science and Technology, vol. 26, 2005, pp. 785-789.*
Selma Turkay et al. : "Deacidification of Sulfur Olive Oil. 1. Single Stage Liquid-Liquid Extraction of Miscella with Ethyl Alcohol", Journal of the American Oil Chemists' Society, vol. 68, No. 2, 1991, pp. 83-86.*
Giovanni Bucolo et al. : "Quantitative Determination of Serum Triglycerides by the Use of Enzymes", Clinical Chemistry, vol. 19, No. 5, 1973, pp. 476-482.*
International Search Report for PCT/EP2011/003182 mailed on Dec. 12, 2011.

* cited by examiner

DEVICE AND METHOD FOR SOLUBILIZING, SEPARATING, REMOVING AND REACTING CARBOXYLIC ACIDS IN OILS, FATS, AQUEOUS OR ORGANIC SOLUTIONS BY MEANS OF MICRO-OR NANOEMULSIFICATION

A. BACKGROUND OF THE INVENTION

The present invention is directed to solubilizing compounds, a device and a method for solubilizing and removing carboxylic acids and especially fatty acids from oils, fats, aqueous emulsions, aqueous or organic solutions. Devices utilizing the inventive method shall be used for separating carboxylic acids from oils, fats, aqueous emulsions, lipophilic media, aqueous media or organic solutions, respectively, thus changing their reaction conditions. One application is a device for removing fatty acids from the blood of subjects in the need thereof. It shall be used further for analytic, respectively diagnostic purposes of fatty acid concentrations in corporal fluids of subjects, foods or pharmaceutical preparations. Furthermore, this technique shall be applied for the removal of carboxylic acid residues in industrial solutions, for example as arising in the food and oil industry.

In general, fatty acids are highly lipophilic molecules which are barely soluble in aqueous solutions. Therefore only small concentrations of fatty acids can be solubilized in aqueous solutions while all fatty acid molecules exceeding this concentration are present in form of micelles, form an emulsion by phase separation, or are absorbed to container walls and/or other lipophilic or amphilic molecules such as proteins in the solution. Above the critical micelle concentration (CMC) of esterified and non-esterified carboxylic acids the concentration of free fatty acids in an aqueous medium remains unchanged.

Fatty acids tend to form emulsions in aqueous media. In presence of proteins or cellular structures fatty acids can be absorbed by them or adsorb to them. Solubilizing of such immobilized fatty acids mainly depends on the critical micelle concentration (CMC) of the fatty acid in the surrounding aqueous medium. Emulators and detergents are able to increase the CMC of hydrophobic substances and thus help to detach immobilized lipophilic molecules. These emulators and detergents may convert emulsions into mini-, micro- or nano-emulsions. Herein the contacting area of the solubilised fatty acids with the aqueous phase is increased. This allows for a better separability and extractability of the solubilised fatty acids. Thus also the reactivity with other molecules is augmented.

Emulsions of esterified and non-esterified fatty acids with an aqueous medium can be completely separated only by means of an organic solvent. Without the help of a membrane this can only be achieved by transferring the fatty acids into an organic phase by mixing with an organic solvent. Extraction is also possible by adsorption to an acceptor. In the presence of adsorber molecules such as proteins the separation of fatty acids in an emulsion or suspension by phase separation or extraction often is incomplete. Furthermore, the capacity of this technique is limited and usually not suited for online (continuous) processing. When filtering such emulsions the aqueous fraction can be filtered almost entirely. However, also hydrophilic molecules, in particular large proteins, are retained and separated along with the organic phase. A molecular separation can be achieved with chromatographic methods. These methods, however, are time-consuming and limited in their capacity.

Another method to separate carboxylic acids from aqueous or organic media is distillation. However, this procedure has a high energy demand and might generate isomerization of the carboxylic acids or denaturate organic components within the medium. A further method is saponification. Added salts are often difficult to remove from the organic as well as from the aqueous solution during further processing.

Thus there is a need for a continuous and selective extraction of fatty acids from emulsions of aqueous or organic solutions. The aim of the present invention is to provide a simple, quick and biocompatible separation of fatty acids from aqueous emulsions or organic media.

Surprisingly, it was found that this aim can be achieved by adding a solubilizing compound to the aqueous emulsion or aqueous media such as blood, lipophilic medium or organic medium containing the carboxylic acids or mixtures of carboxylic acids with other organophilic molecules. An inventive solubilizing compound having the characteristics as defined herein is able to solubilize carboxylic acids and convert the emulgated carboxylic acids into micro- or nanoemulsions which allow a separation by means of separation methods such as dialysis, filtration and electrophoresis.

Thus the task is solved by the ensuing technical teachings of the independent claims of the present invention. Further advantageous embodiments of the invention result from the dependent claims, the description and the examples.

Fatty Acids

In general, fatty acids have a carboxylic head group and a long aliphatic chain. Depending on the presence of double bonds they are differentiated into saturated and unsaturated fatty acids. There are differing definitions in literature about fatty acids. One definition states that carboxylic acids with 4 carbon atoms or higher are regarded as fatty acids. Naturally occurring fatty acids, however, have at least 8 carbon atoms. At these carbon atoms at least one nitro group can replace hydrogen atom(s) and turn them into nitro-fatty acids. Also nitro-fatty-acids may carry further substituents, such as listed above.

Examples for linear saturated fatty acids are octanoic acid (caprylic acid), decanoic acid (caprinic acid), dodecanoic acid (lauric acid), tetradecanoic acid (myristic acid), hexadecaoic acid (palmitic acid), heptadecanoic acid (margaric acid), octadecanoic acid (stearic acid), eicosanoic acid (arachidic acid), docosanoic acid (behenic acid) and tetracosanoic acid (lignoceric acid).

According to the invention a preferred subgroup of the saturated fatty acids to be separated are myristic acid, palmitic acid, and stearic acid.

Examples for monoolefinic fatty acids are cis-9-tetradecenoic acid (myristoleic acid), cis-9-hexadecenoic acid (palmitoleic acid), cis-6-hexadecenoic acid (salpenic acid), cis-6-octadecenoic acid (petroselinic acid), cis-9-octadecenoic acid (oleic acid), cis-11-octadecenoic acid (vaccenic acid), 12-hydroxy-9-cis-octadecenoic acid (ricinoleic acid), cis-9-eicosenoic acid (gadoleinic acid), cis-1'-eicosenoic acid (gondoic acid), cis-13-docosenoic acid (erucic acid), cis-15-tetracosenoic acid (nervonic acid), t9-octadecenoic acid (elaidic acid), t11-octadecenoic acid (t-vaccenic acid) and t3-hexadecenoic acid. According to the invention a preferred subgroup of the unsaturated fatty acids to be separated are the trans-isomers t9-octadecenoic acid, t11-octadecenoic acid, and t3-hexadecenoic acid.

Examples for polyolefinic fatty acids are 9,12-octadecadienoic acid (linoleic acid), 6,9,12-octadecatrienoic acid (γ-linoleic acid), 8,11,14-eicosatrienoic acid (dihomo-γ-linoleic acid), 5,8,11,14-eicosatrienoic acid (arachidonic acid), 7,10, 13,16-docosatetraenoic acid, 4,7,10,13,16-docosapentaenoic acid, 9,12,15-octadecatrienoic acid (α-linolenic acid), 6,9, 12,15-octadecatetraenic acid (stearidonic acid), 8,11,14,17-eicosatetraenoic acid, 5,8,11,14,17-eicosapentaenoic acid (EPA), 7,10,13,16,19-docosapentaenoic acid (DPA), 4,7,10, 13,16,19-docosahexaenic acid (DHA), 5,8,11-eicosatrienoic acid (mead acid), 9c 11t 13t eleostearinoic acid, 8t 10t 12c calendic acid, 9c 11t 13c catalpic acid, 4, 7, 9, 11, 13, 16, 19 docosaheptadecanoic acid (stellaheptaenoic acid), taxolic acid, pinolenic acid and sciadonic acid.

According to the invention a preferred subgroup of the unsaturated fatty acids to be separated are the trans-isomers of linoleic acid, γ-linoleic acid, EPA, and DPA.

Examples for acetylenic fatty acids are 6-octadecinoic acid (tariric acid), t11-octadecen-9-ynoic acid (santalbic or ximenic acid), 9-octadecynoic acid (stearolic acid), 6-octadecen-9-ynoic acid (6,9-octadecenynoic acid), t10-heptadecen-8-ynoic acid (pyrulic acid), 9-octadecen-12-ynoic acid (crepenic acid), t7,t11-octadecadiene-9-ynoic acid (heisteric acid), t8,t10-octadecadiene-12-ynoic acid, 5,8,11,14-eicosatetraynoic acid (ETYA).

It shall be noted that according to the invention also the bases, respectively salts of the aforementioned fatty acids shall be subsumed under the general terms fatty acids or free fatty acids.

Examples for suitable organic and inorganic bases for salt formation are bases derived from metal ions, e.g., aluminum, alkali metal ions, such as sodium of potassium, alkaline earth metal ions such as calcium or magnesium, or an amine salt ion or alkali- or alkaline-earth hydroxides, -carbonates or -bicarbonates. Examples include aqueous sodium hydroxide, lithium hydroxide, potassium carbonate, ammonia and sodium bicarbonate, ammonium salts, primary, secondary and tertiary amines, such as, e.g., lower alkylamines such as methylamine, t-butylamine, procaine, ethanolamine, arylalkylamines such as dibenzylamine and N,N-dibenzylethylenediamine, lower alkylpiperidines such as N-ethylpiperidine, cycloalkylamines such as cyclohexylamine or dicyclohexylamine, morpholine, glucamine, N-methyl- and N,N-dimethylglucamine, 1-adamantylamine, benzathine, or salts derived from amino acids like lysine, ornithine or amides of originally neutral or acidic amino acids or the like.

The following carboxylic acids are preferred examples of fatty acids:

octanoic acid (caprylic acid), decanoic acid (capric acid), dodecanoic acid (lauric acid), tetradecanoic acid (myristic acid), hexadecanoic acid (palmitic acid), heptadecanoic acid (margaric acid), octadecanoic acid (stearic acid), eicosanoic acid (arachidic acid), docosanoic acid (behenic acid), tetracosanoic acid (lignoceric acid), cis-9-tetradecenoic acid (myristoleic acid), cis-9-hexadecenoic acid (palmitoleic acid), cis-6-octadecenoic acid (petroselinic acid), cis-9-octadecenoic acid (oleic acid), cis-11-octadecenoic acid (vaccenic acid), cis-9-eicosenoic acid (gadoleic acid), cis-11-eicosenoic acid (gondoic acid), cis-13-docosenoic acid (erucic acid), cis-15-tetracosenoic acid (nervonic acid), t9-octadecenoic acid (elaidic acid), t11-octadecenoic acid (t-vaccenic acid), t3-hexadecenoic acid, 9,12-octadecadienoic acid (linoleic acid), 6,9,12-octadecatrienoic acid (γ-linoleic acid), 8,11,14-eicosatrienoic acid (dihomo-γ-linolenic acid), 5,8,11,14-eicosatetraenoic acid (arachidonic acid), 7,10,13,16-docosatetraenoic acid, 4,7,10,13,16-docosapentaenoic acid, 9,12,15-octadecatrienoic acid (α-linolenic acid), 6,9,12,15-octadecatetraenoic acid (stearidonic acid), 8,11, 14,17-eicosatetraenoic acid, 5,8,11,14,17-eicosapentaenoic acid (EPA), 7,10,13,16,19-docosapentaenoic acid (DPA), 4,7,10,13,16,19-docosahexaenoic acid (DHA), 5,8,11-eicosatrienoic acid (mead acid), 9c 11t 13t eleostearic acid, 8t 10t 12c calendic acid, 9c 11t 13c catalpic acid, 4, 7, 9, 11, 13, 16, 19 docosaheptadecanoic acid (stellaheptaenoic acid), taxoleic acid, pinolenic acid, sciadonic acid, 6-octadecynoic acid (tariric acid), t1'-octadecen-9-ynoic acid (santalbic or ximenynic acid), 9-octadecynoic acid (stearolic acid), 6-octadecen-9-ynoic acid (6,9-octadecenynoic acid), t10-heptadecen-8-ynoic acid (pyrulic acid), 9-octadecen-12-ynoic acid (crepenynic acid), t7,t11-octadecadiene-9-ynoic acid (heisteric acid), t8,t10-octadecadiene-12-ynoic acid, 5,8,11,14-eicosatetraynoic acid (ETYA), eleostearic acid, calendic acid, catalpic acid, stellaheptaenoic acid, taxoleic acid, retinoic acid, isopalmitic acid, pristanic acid, phytanic acid, 11,12-methyleneoctadecanoic acid, 9,10-methylenhexadecanoic acid, coronaric acid, (R,S)-lipoic acid, (S)-lipoic acid, (R)-lipoic acid, 6,8-bis(methylsulfanyl)-octanoic acid, 4,6-bis(methylsulfanyl)-hexanoic acid, 2,4-bis(methylsulfanyl)-butanoic acid, 1,2-dithiolane carboxylic acid, (R,S)-6,8-dithiane octanoic acid, (R)-6,8-dithiane octanoic acid, (S)-6, 8-dithiane octanoic acid, cerebronic acid, hydroxynervonic acid, ricinoleic acid, lesquerolic acid, brassylic acid and thapsic acid.

Fatty Acids in Blood

In mammals fatty acids serve as physiologically important energy substrates and play a critical role in energy metabolism. Moreover, they are important substrates for the synthesis of membrane phospholipids and biologically active agents like eicosanoids and leukotrienes. The mammalian body heavily relies on fatty acids as suppliers of chemically stored energy, building blocks of cellular membranes and signal transducers. The main source of fatty acids is dietary lipid, digested in the gastro-intestinal tract by the catalytic action of pancreatic hydrolytic enzymes. Part of fatty acids is produced by the liver taking carbohydrates as substrate. A large percentage of fatty acids, however, is stored in fat cells (adipocytes) composing adipose tissue in form of triacylglycerol.

The concentration of esterified and unesterified fatty acids in the blood depends on several factors such as food intake or release from adipose tissue. Fatty acids can be bound or attached to other molecules, such as in triglycerides or phospholipids, or to a smaller percentage fatty acids occur unbound. In any case, fatty acids are insoluble in water and must be bound to a water soluble component for transport in the organism. Fatty acids are transported in the body via the lymphatic and vascular system. Basically, two transport forms are at hand: Fatty acids can be transported as triacylglycerols, which is the main component of circulating lipoproteins such as chylomicrons and very-low density lipoproteins, or as non-esterified fatty acids that are bound to plasma proteins, in particular plasma albumin. Free fatty acids that are completely unbound have a very low solubility and only occur in very low concentrations.

The composition, distribution and concentration of fatty acids in human blood can vary a lot and is made up by the sum of the different fractions of plasma: Cholesterol ester, phospholipids, and triacylglycerols as well as albumin-bound fatty acids. The saturated fatty acids in human blood are mostly made up by myristic acid (14:0), palmitic acid (16:0) and stearic acid (18:0). The main type of monounsaturated fatty acids belong to the group of oleic acid (18:1) and palmitoleic acid (16:1). Polyunsaturated omega-3 fatty acids include linolenic acid (18:3), eicosapentaenoic acid (20:5), docosapentaenoic acid (22:5) and docosahexaenoic acid (22:6). Polyunsaturated omega-6 fatty acids are mostly linoleic acid (18: 2), eicosadienoic acid (20:2), dihomogammalinolenic acid (20:3), arachidonic acid (20:4), adrenic acid (22:4) and docosapentaenoic acid (22:5). The concentration of other fatty acids is usually very low in whole blood, but can vary depending on genetics, nutrition and life style.

Blood fatty acids concentrations are increased in obese patients and contribute to type 2 diabetes, hepatic steatosis and several cardiovascular disorders such as atherosclerosis. The pathogenetic role of fatty acids in the development of athrosclerosis and associated diseases such as cerebral, myocardal, renal, erectile dysfunction has been elucidated. Not intended to be comprehensive, some aspects should be outlined in the following. An elevation of fatty acids was found to be responsible for increase of reactive oxygen radical formation causing endothelial dysfunction which can be attenuated by an antioxidant (Pleiner et al, FFA-induced endothelial dysfunction can be corrected by vitamin C. J Clin Endocrinol Metab 2002, 87, 2913-7). This effect is increased by trans-fatty acids which are suspected to have additional deliterious effects (Lopez Garcia et al, Consumption of trans-fatty acids is related to plasma biomarkers of inflammation and endothelial dysfunction. J Nutr 2005, 135, 562-566; Mozaffarian et al, Health effects of trans-fatty acids: experimental and observational evidence. Eur J Clin Nutr 2009, 63 Suppl 2, S5-21). They are accused to increase blood pressure and found to be a pathogenetic factor in arterial hypertension (Zheng et al, Plasma fatty acid composition and 6-year incidence of hypertension in middle-aged adults: the Atherosclerosis Risk in Communities (ARIC) Study. Am J Epidemiol 1999, 150, 492-500). Trans-fatty acids were found to increase the risk of myocardial infarction and sudden heart death (Ascherio et al, Trans-fatty acids intake and risk of myocardial infarction. Circulation 1994, 89, 94-101; Baylin et al, High 18:2 trans-fatty acids in adipose tissue are associated with increased risk of nonfatal acute myocardial infarction in Costa Rican adults. J Nutr 2003, 133, 1186-1191). Together with a chronic elevation of fatty acid blood concentrations they are responsible for insulin resistance and development of diabetes mellitus (Krachler et al, Fatty acid profile of the erythrocyte membrane preceding development of Type 2 diabetes mellitus. Nutr Metab Cardiovasc Dis 2008, 18, 503-510; Lionetti et al, From chronic overnutrition to insulin resistance: the role of fat-storing capacity and inflammation. Nutr Metab Cardiovasc Dis 2009, 19, 146-152; Yu et al, Mechanism by which fatty acids inhibit insulin activation of insulin receptor substrate-1 (IRS-1)-associated phosphatidylinositol 3-kinase activity in muscle. J Biol Chem 2002, 277, 50230-50236). Altogether an increased turn-over of fatty acids as a result of chronic over-nutrition is now believed to be the most important patho-mechanism in the development of the most common diseases in industrialized countries (Bays, "Sick fat," metabolic disease, and atherosclerosis. Am J Med 2009, 122, S26-37). Medical treatment for effective reduction of overweight is lacking (Aronne et al, When prevention fails: obesity treatment strategies. Am J Med 2009, 122, S24-32). However, obese persons who succeed in reducing body weight and thus a significant reduction of fatty acid-induced disorders can be found (Lien et al, The STEDMAN project: biophysical, biochemical and metabolic effects of a behavioral weight loss intervention during weight loss, maintenance, and regain. Omics 2009, 13, 21-35; Schenk et al, Improved insulin sensitivity after weight loss and exercise training is mediated by a reduction in plasma fatty acid mobilization, not enhanced oxidative capacity. J Physiol 2009, 587, 4949-4961). Therefore a medical device to effectively reduce the total amount of fatty acids and preferably those with increased pathogenicity is desirable.

Surgical extraction of subcutaneous adipose tissue was found to be ineffective in reducing circulating fatty acid concentrations or their qualitative content. Removal of the lipoprotein fraction carrying high concentrations of cholesterol by direct adsorption from blood can be accomplished by adsorption or filtration of these particles. Those procedures for online blood purification are called LDL apheresis. While designed to reduce LDL cholesterol, they also adsorb triglycerides. However, the quantity of triglycerides extracted is not sufficient for an effective reduction of the body content of fatty acids.

The fatty acid content of blood is low in the fastening state at rest. However, significant rise is observed during lipolysis (see below). Due to the insolubility in an aqueous medium the transport of unesterified fatty acids is accomplished by proteins and cellular structures (Spector et al, Utilization of long-chain free fatty acids by human platelets. J Clin Invest 1970, 49, 1489-1496). The major transport protein in blood is albumin. The presence of at least 10 specific binding sites for fatty acids has been documented. However, the binding capacity might increase dramatically by formation of micellar structures with fatty acids in a condition of excess of fatty acids or other lipids (Schubiger et al, Mixed micelles: a new problem-free solution for omega-$^{123}$I-heptadecanoic acid in comparison. Nuklearmedizin 1984, 23, 27-28).

With a molarity of albumin of about 600 µmol/l a binding capacity of at least 0.006 mol/l for fatty acids would exist which equals about 0.0035 kg/l (Berk and Stump, Mechanisms of cellular uptake of long chain free fatty acids. Mol Cell Biochem 1999, 192, 17-31).

Furthermore, fatty acids are transported in esterified form as mono-, di- or triacyl glycerols. The fastening serum concentration varies considerably. However, normal values are set to be below 150 mg/dl (1.7 mmol/l). Postprandially or during exercising the concentration can rise several-fold and even exceed 1000 mg/dl (11.3 mmol/l).

Only spare reports exist which investigate the differences in the lipid content at various sites within the circulation. In these investigations significant higher values for fatty acids and triglycerides were found to be present in the central venous system (Vena cava) as compared to other measuring sites (Wiese et al, Lipid composition of the vascular system during infancy, childhood, and young adulthood, J. Lipid Res. 1967, 8, 312-320; Zauner et al, Pulmonary arterial-venous differences in lipids and lipid metabolites. Respiration 1985, 47, 214-219). No reports exist about the changes of the central venous lipid content during exercise and induced lipolysis.

It was found now, that during physical excercising the lipid content sharply increases in the central abdominal veins exhibiting an increasing difference in the lipid content between the central as compared to a peripheral assess site as described below.

Thus reducing the fatty acid content in blood using the methods and the devices and the solubilizing compounds disclosed herein is useful to treat the diseases mentioned above associated with an elevated level of fatty acids in the blood or in the organism.

Thus the present invention relates to the treatment and prophylaxis of fatty acid-induced disorders such as type 2 diabetes, hepatic steatosis, cardiovascular disorders such as arterial hypertension, myocardial infarction, stroke, sudden heart death, atherosclerosis, diseases associated with atherosclerosis such as cerebral, myocardial, renal and erectile dysfunction, as well as to weight reduction and cholesterol reduction and also to the prevention of insulin resistance and the prevention of the development of diabetes mellitus by using the solubilizing compounds disclosed herein in order to remove fatty acids from the blood.

Lipolysis

Plasma fatty acids are an important energy substrate. The availability of fatty acids is determined predominantly by their mobilization from adipose tissue triacylglycerol stores by the process of lipolysis. In man, lipolysis of adipose tissue is regulated by a number of hormonal, paracrine and/or autocrine signals. The main hormonal signals may be represented by catecholamines, insulin, growth hormone, natriuretic peptides, thyroxine, and some adipocytokines (Stich and Berlan, Physiological regulation of NEFA availability: lipolysis pathway. Proc Nutr Soc 2004, 63, 369-374). The absolute levels and relative importance and contribution of these signals vary in different physiological situations, with diet and physical exercise being the main physiological variables that affect hormonal signalling. A family of enzymes called lipases with distinct functions is responsible for the breakdown of triglycerides stored within fat cells for energy storage. Carbonhydrates and fatty acids are the major energy fuels for muscle contraction. During exercise training lipolysis liberates 7.1+/−1.2 micromol×min(−1)×kg(−1) body weight, which would result in a release of fatty acids of 4200 μmol per hour in a person with a weight of 100 kg which equals 0.15 kg fatty acids (Coggan et al, Fat metabolism during high-intensity exercise in endurance-trained and untrained men. Metabolism 2000, 49, 122-128). However, stimulation of lipolysis by pharmacological intervention and/or local physical measures may further increase lipolytic capacity. Lipolysis was increased up to 3-fold by systemic application of natural receptor agonists or drugs (Riis et al, Elevated regional lipolysis in hyperthyroidism. J Clin Endocrinol Metab 2002, 87, 4747-4753; Barbe et al, In situ assessment of the role of the beta 1-, beta 2- and beta 3-adrenoceptors in the control of lipolysis and nutritive blood flow in human subcutaneous adipose tissue. Br J Pharmacol 1996, 117, 907-913). Adrenoreceptor agonists exhibiting stimulating lipolysis are: Adrenaline, noradrenaline, isoprenaline, ephedrine, isoproteriol, salbutamol, theophylline, fenoterol, orciprenaline, a.o.

Lipolytic effects have also been described from physical alterations of fat tissue. Researchers found that ultrasound had a liquidifying effect on adipose tissue leading to a reduced content of fat tissue when performed during starvation (Faga et al, Ultrasound-assisted lipolysis of the omentum in dwarf pigs. Aesthetic Plast Surg 2002, 26, 193-196; Miwa et al, Effect of ultrasound application on fat mobilization. Pathophysiology 2002, 9, 13).

Though for all measures mentioned above increase in lipolysis has been documented the measurable effect on concentrations of unesterified fatty acids was small. In a pilot investigation it was found that after stimulation of lipolysis the content of fatty acids tremendously increased when measured by using the intentive method for solubilisation of fatty acids. Furthermore, it was found that the content of fatty acids was much higher within the abdominal venous system than in the peripheral circulation. This finding is surprising, since it has not been observed in animal studies when measuring various blood collections sites simultaneously.

Therefore, stimulation of lipolysis while performing blood purification from fatty acids by the intentive procedure and using an abdominal central vene as an access site is a preferred embodiment of the invention.

The extraction fraction could be increased if the content of esterified and unesterified fatty acids transported in blood could be elevated while performing the procedure.

Surprisingly, this task could be solved by increasing lipolysis through the inventive method.

Solvation and Adhesion Behavior of Fatty Acids in Aqueous Media

The solubility of carboxylic acids in water is minimal when the length of the carbon chain exceeds 4 carbon atoms and in absence of hydroxy (—OH) groups, carboxyl (—COOH) groups or other hydrophilic polar or charged groups and/or by introduction of alkyl substituents or other lipophilic groups.

Solubility can be increased by detergents which penetrate fatty acid micelles thereby reducing their stability and reducing their size, and increasing the number of free fatty acid molecules in the aqueous medium. Both free fatty acids and micelles tend to bind to lipotropic structures. Among those are carbon, metals, ceramics, natural and synthetic polymers. Furthermore, organic structures carry lipophilic regions, some of which are designated to specifically bind fatty acids, which form membrane or lipid transport proteins. The steric binding sites are mostly lined by hydrophobic amino acids.

In blood, lipids are electrostatically bound to specialized transport proteins. Fatty acids are mainly transported by albumin. The binding of fatty acids at the albumin molecule relies also on electrostatic forces which are localized in hydrophobic pockets. The binding energy of those pockets varies, however the $pK_a$ for all of them is substantially higher than the CMC of the fatty acids. Therefore, fatty acids remain in the surrounding medium even after complete removal of free fatty acids. Extraction of fatty acids from albumin was found to be almost complete when organic solvents were used for their liberation because of the better dissolution in organic solvents. However, those solvents alter the protein structure making them unsuitable for further processing or use in a living organism. To use albumin for medical or other purposes it is necessary to reduce their fatty acid content without altering the structure and functionality of albumin. This task can be solved by activated carbon particles which possess a higher binding affinity to fatty acids than albumin. However, this process needs further steps for purification of albumin. Therefore up to now there is no procedure that allows quick liberation and solubilization of the whole fatty acid content of an albumin molecule within an aqueous medium which does not alter the ultrastructure and function of the albumin molecules.

Carboxylic acids are also transported within phospholipid vesicles. Electrostatic interactions between the hydrocarbon chains of the carboxylic acids and those of the phospholipids retain carboxyl acids from diffusion to a surrounding aqueous medium. Mutatis mutandis, this applies also for other organic solutions, biomasses or organic waste waters. In organic solutions destinated for further refinement, purification or use where it is desirable not to use an organic solvent, an alternative biocompatible procedure is desirable. So far such a procedure is lacking.

Surprisingly, this aim can be reached by the use of at least one solubilizing compound as disclosed herein comprising at least one amidino and/or at least one guanidino moiety and especially solubilizing compounds of general formula (I), (II) and (III) and most especially arginine and derivatives thereof.

The carboxylic acids which shall be removed are normally contained in an aqueous medium or aqueous solution such as blood or blood plasma or in an aqueous emulsion such as milk or in an organic medium such as fuel, gas, bio-diesel, gasoline, petrol and the like or in oils such as vegetable oils like linseed oil, walnut oil, flax oil, evening primrose oil, sunflower oil, sunflower seed oil, soybean oil, rapeseed oil, olive oil, virgin olive oil, palm oil, palm kernel oil, peanut oil, cottonseed, coconut oil, corn oil, grape seed oil, hazelnut oil, rice bran oil, safflower oil, sesame oil as well as animal oils such as fish oil or contained in fats such as butter, oleo or margarine.

In case the carboxylic acid is contained in water, an aqueous medium, an aqueous emulsion or an aqueous suspension, the at least one solubilizing compound can be directly added to the aqueous medium, emulsion or suspension or the at least one solubilizing compound can be dissolved in water and this aqueous solution can be added to the aqueous medium, emulsion or suspension containing the carboxylic acids. After this addition the formation of a nanoemulsion and/or microemulsion is observed.

In case the carboxylic acids are contained in an organic medium or a lipophilic organic medium, the solubilizing compound is dissolved in water and the solution of the solubilizing compound in water is added to the organic medium. A two phase mixture is obtained and the carboxylic acids are transferred into the aqueous phase. It is assumed that a complex or aggregate of one molecule carboxylic acid with one molecule solubilizing compound or a dimer or trimer thereof is formed which makes the carboxylic acid soluable in water. Thus it is preferred to stir or shake the two phase mixture of the organic and aqueous layer in order to obtain an intensive mixing of the two layers. The carboxylic acids contained in the aqueous phase can be removed by phase separation. If desired, the extraction method can be repeated.

In case the carboxylic acids are contained in an oil or fat, the solubilizing compound is dissolved in water and the solution of the solubilizing compound in water is added to the oil or fat. If desired, an organic solvent could be added to the oil or fat in order to reduce viscosity of the oil or fat to make the oil or fat better stirrable. The mixture of the oil or fat and the aqueous solution of the solubilizing compound is stirred. The carboxylic acid is transferred into the aqueous phase and the aqueous phase can be removed by decantation or phase separation. The extraction process can be repeated for several times if desired.

Thus the invention also relates to an aqueous microemulsion and/or an aqueous nanoemulsion containing at least one solubilizing compound and at least one carboxylic acid in a microemulgated or in a nanoemulgated form.

If the solubilizing compound is used in an excess of 1.2 to 2.8, preferably 1.5 to 2.5 and more preferably in an excess of 1.7 to 2.3 mol equivalents, it is possible to remove more than 90% of the carboxylic acids in one extraction step. If the extraction step is repeated twice, up to 99% of the carboxylic acids can be removed.

The carboxylic acids which can be removed are especially carboxylic acids with more than 5 carbon atoms, more preferably with more than 7 carbon atoms and especially preferred with more than 9 carbon atoms. Preferably the carboxylic acids are fatty acids as disclosed herein while also other lipophilic compounds containing a carboxyl group or carboxylic acid group such as drugs or toxines can be removed by this method. One carboxylic acid which is explicitly disclaimed from the present invention is naproxen. Moreover it is not the intention of the present invention to provide methods and compounds or devices for the solubilization of pharmaceuticals in order to prepare galenic formulations. Especially preferred is the removal and solubilization of naphthenic acid from oil, petrol, gas and fuel. Moreover preferred carboxylic acids are such carboxylic acids which contain double and/or triple bonds such as unsaturated and polyunsaturated fatty acids. Still more preferred are physiologic carboxylic acids and especially these physiologic carboxylic acids which occur in human beings. For industrial purposes the unsaturated fatty acids are preferably removed and solubilized from the source material such as oils and fats while for medical purposes the saturated fatty acids are preferably removed from the blood of the patient. Moreover these carboxylic acids are preferred which occur in oil and fats of the above mentioned origin, especially from animals such as fishes, corn, olives, corn, crop, rice, soya and the like. In case the carboxylic acids which shall be removed from the organic medium such as fats, waxes, oil, fuel, petrol and the like are contained in esterified form (i.e. are bound in esters), a saponification step can be performed before the inventive removal and solubilization is carried out. Such a saponification is preferably performed in a solvent mixture of water and at least a second solvent miscible with water. Further preferred carboxylic acids are perfluoro carboxylic acids such perfluoropropionic acid, perfluorooctanoic acid (PFOA), perfluorodecanoic acid, perfluorododecanoic acid, perfluorohexadecanoic acid as well as other perfluoro carboxylic acids and prophyrinic acid.

The present invention also refers to the solubilization, respectively the removal of aromatic carboxylic acids belonging to the above-mentioned target groups, such as benzoic acid, 4-aminobenzoic acid, anthranilic acid, benzilic acid, cinnamic acid, salicylic acid, phenylacetic acid, 4-methoxyphenylacetic acid, gallic acid, phthalic acid, terephthalic acid, abietic acid, bicinchoninic acid, quinic acid, chorismic acid, clavulanic acid, fusaric acid, fusidic acid, uric acid, hippuric acid, ibotenic acid, indole-3-acetic acid, mandelic acid, styphnic acid, usnic acid, abscisic acid, tropic acid, benzoquinonetetracarboxylic acid, boswellic acid, caffeic acid, carminic acid, chenodeoxycholic acid, coumaric acid, cromoglicic acid, cynarine, meclofenamic acid, 2,4-dichlorophenoxyacetic acid, domoic acid, pipemidic acid, ferulic acid, 5-hydroxyferulic acid, isophthalic acid, mefenamic acid, meta-chloroperoxybenzoic acid, peroxybenzoic acid, protocatechuic acid, nalidixic acid, sinapic acid, sucrononic acid.

Especially preferred is the removal and solubilization of carboxylic acids from blood which lead to various diseases caused and/or associated by an increased and/or unhealthy level of such carboxylic acids and especially fatty acids.

The carboxylic acids are preferably lipophil and preferably have a partition coefficient between n-octanol and water (also known as log $K_{OW}$ or octanol-water-partition coefficient) of >2.0, preferably of >3.0 and more preferably of >4.0. (For example: log $K_{OW}$ of acetic acid is −0.17, of butyric acid is 0.79, of octanoic acid is 3.05 and of decanoic acid is 4.09).

It is also preferred if the carboxylic acids which shall be removed have an pKs value >4.85, preferably >4.87. (for instance: acetic acid has pKs of 4.76, butyric acid of 4.82, pentanoic acid of 4.84 and octanoic acid of 4.89).

Thus the present invention provides a method for separating carboxylic acids which are not at all or not good soluable in water and which can be solubilized in water by means of the solubilizing compounds disclosed herein preferably in form of nano- or microemulsions. Once transferred into the aqueous phase, the fatty acids can be removed by various technics disclosed herein.

Thus the present invention relates to the use of a solubilizing compound for solubilizing carboxylic acids in an aqueous or organic medium, wherein said solubilizing compound contains at least one amidino group and/or at least one guanidino group and wherein the compound has a partition coefficient between n-octanol and water of $K_{OW}$<6.30.

The term "solubilizing carboxylic acids in an aqueous or organic medium" should be understood as follows: the carboxylic acids which shall be solubilized are contained in an organic medium such as oils or fuel or in an aqueous medium such as blood or milk and are solubilized by the use of a solubilizing compound in the aqueous phase.

Thus it can also be stated that the present invention is directed to the use of a solubilizing compound for solubilizing carboxylic acids from an aqueous or organic medium in an aqueous phase, wherein said solubilizing compound contains at least one amidino group and/or at least one guanidino group and wherein the compound has a partition coefficient between n-octanol and water of $K_{OW}$<6.30.

Moreover the present invention relates to the use of a solubilizing compound for solubilizing lipophilic carboxylic acids in an aqueous medium, wherein said solubilizing compound contains at least one amidino group and/or at least one guanidino group and wherein the compound has a partition coefficient between n-octanol and water of $K_{OW}$<6.30.

In case where the carboxylic acids are contained in the aqueous phase such as blood, only very few amounts of free carboxylic acids are present in the blood, since these carboxylic acids and especially fatty acids are poorly water soluable. Most of the carboxylic acids which should be removed from the blood are bound to other compounds such as albumin and are no longer free carboxylic acids. However there is an equilibrium between the very small amount of free carboxylic acids in the blood and the otherwise bound or deposited carboxylic acids which are regarded as not free anymore. If now by means of the inventive method the free carboxylic acids are complexed by the solubilizing compound, these free carboxylic acids are removed from the equilibrium and albumin bound carboxylic acids are released into the blood which than can again be removed by the inventive method so that finally almost all carboxylic acids contained in the blood in a free or bound form can be removed. Especially dialysis is suitable for such a continuous process of removing the carboxylic acids and especially fatty acids from the blood.

The solubilizing compounds disclosed herein comprise at least one amidino group or at least one guanidino group or at least one amidino group and at least one guanidino group. If the amidino group is not substituted it can be represented by the following formula $H_2N-C(NH)-$. But it is also possible that all three hydrogen atoms are replaced by substituents R, R' and R" as represented by the following general formula $(R)(R')N-C(NR")-$. It is preferred if two of the three hydrogen atoms are replaced by a substituent as represented by the following formula: $(R')NH-C(NR")-$ or $(R)(R')N-C(NH)-$. Thus amidino groups with at least one hydrogen are preferred. If the guanidino group is not substituted it can be represented by the following formula $H_2N-C(NH)-NH-$. But it is also possible that all four hydrogen atoms are replaced by substituents R, R', R" and R'" as represented by the following formula $(R)(R')N-C(NR")-N(R''')-$. It is preferred if three of the four hydrogen atoms are replaced by a substituent as represented by the following formula: $(R')NH-C(NR")-N(R''')-$ or $(R)(R')N-C(NH)-N(R''')-$ or $(R)(R')N-C(NR")-NH-$. Thus guanidino groups with at least one hydrogen and preferably with two hydrogens are preferred.

The solubilizing compound comprises or contains at least one amidino group and/or at least one guanidino group, while guanidino groups are preferred. Moreover the solubilizing compound comprises or contains preferably not more than 15 carbon atoms, more preferably not more than 14, more preferably not more than 13, more preferably not more than 12, more preferably not more than 11, more preferably not more than 10, more preferably not more than 9, and more preferably not more than 8 carbon atoms and most preferably the solubilizing compound is an arginine derivative. In case of polymeric or oligomeric solubilizing compounds it is preferred that per amidino moiety or per guanidino moiety not more than 10 carbon atoms and more preferably not more than 8 carbon atoms are present.

Furthermore the solubilizing compound is hydrophil and may preferably contain one or more of the following substituents:
$-NH_2$, $-OH$, $-PO_3H_2$, $-PO_3H^-$, $-PO_3^{2-}$, $-OPO_3H_2$, $-OPO_3H$, $-OPO_3^{2-}$, $-COOH$, $-COO^-$, $-CO-NH_2$, $-NH_3^+$, $-NH-CO-NH_2$, $-N(CH_3)_3^+$, $-N(C_2H_5)_3^+$, $-N(C_3H_7)_3^+$, $-NH(CH_3)_2^+$, $-NH(C_2H_5)_2^+$, $-NH(C_3H_7)_2^+$, $-NHCH_3$, $-NHC_2H_5$, $-NHC_3H_7$, $-NH_2CH_3^+$, $-NH_2C_2H_5^+$, $-NH_2C_3H_7^+$, $-SO_3H$, $-SO_3$, $-SO_2NH_2$, $-CO-COOH$, $-O-CO-NH_2$, $-C(NH)-NH_2$, $-NH-C(NH)-NH_2$, $-NH-CS-NH_2$, $-NH-COOH$.

Also preferred are solubilizing compounds which are derivatives of arginine or which are dipeptides or tripeptides or polypeptides containing the amino acid arginine or a derivative of arginine.

It is also possible that the amidino group or the guanidino group is part of a heterocyclic ring system like in imidazole, histidine, clothianidin or 4-(4,5-dihydro-1H-imidazol-2-ylamino)-butyric acid.

The solubilizing compounds are hydrophil and have a partition coefficient between n-octanol and water (also known as $K_{OW}$ or octanol-water-partition coefficient) of $K_{OW}$<6.30 (log $K_{OW}$<0.80), preferably $K_{OW}$<1.80 (log $K_{OW}$<0.26), more preferably $K_{OW}$<0.63 (log $K_{OW}$<−0.20) and most preferably $K_{OW}$<0.40 (log $K_{OW}$<−0.40).

Preferred solubilizing compounds are:
L-2-amino-3-guanidinopropionic acid, L-arginine, L-NIL, H-homoarg-OH, histidine, Nω-nitro-L-arginine, N-ω-hydroxy-L-norarginine, D-arginine methyl ester, nomega-monomethyl-L-arginine, NG,NG-dimethylarginine, D-(+)-octopine, argininosuccinic acid, L-canavanine free base, creatine, guanidinoacetic acid, 3-guanidinopropionic acid, 4-guanidinobutyric acid, 4-(4,5-dihydro-1H-imidazol-2-ylamino)-butyricacid, (S)-(−)-2-guanidinoglutaric acid, 6-guanidinohexanoic acid, guanidino, sulfaguanidine, agmatinsulfate, 4-guanidinobenzoicacid, 1,3-di-o-tolyl-guanidine, clothianidine, L-ornitin, N-guanylurea, cimetidine, 1-(o-tolyl)biguanide, chlorhexidine, 1,1-dimethylbiguanide, proguanil, polyhexanide, poly-L-arginine (70.000-150.000 mw), diminazene, melanine, 4-(4,6-diamino-2,2-dimethyl-2H-[1,3,5]triazine-1-yl, imidazole, methylimidazole, Tyr-Arg (Kyotorphin), Arg-Gln, Gly-Arg, Arg-Phe, Arg-Glu, Lys-Arg acetate, His-Arg, Arg-Gly-Asp (RGD), Arg-Phe-Ala, Thr-Lys-Pro-Arg (Tuftsin), Gly-Gly-Tyr-Arg, Gly-His, argatroban, L-NMMA (L-NG-monomethyl-arginine), L-NAME (L-nitro-arginin-methylester), L-hydroxy-arginin-citrate, dimethylarginine (ADMA), D-homoarginine, noraginine, L-canavanin (2-amino-4-(guanidinooxy)-butyric acid), 4-guanidino-phenylalanine, 3-guanidino-phenylalanine, O-α-hippuryl-L-argininic acid, H-Arg-AMC (L-arginin-7-amido-4-methylcumarin), L-TAME (P-tosyl-L-arginin-methylester), diphenylacetyl-D-Arg-4-hydroxybenzylamid, agmatin (argamin; 1-amino-4-guanidinobutansulfate), L-arginin-ethylester, L-arginin-methylester, guanidine, guanidinacetate, guanidincarbonate, guanidinnitrate, guanidinthiocyanate, guanyl urea, guanyl urea phosphate, guanyl urea dinitramide, 2-guanidinoacetaldehyd-diethylacetale, dicyandiamide, 2-guanidinobenzimidazol, S-((2-guanidino-4-thiazolyl)methyl)-isothio urea, guanidinobutylaldehyde, 4-guanidinobenzoic acid, leonurin (4-guanidino-n-butylsyringate), ambazon ([4-(2-(diaminomethyliden)-hydrazinyl)phenyl]iminothio urea), amilorid (3,5-diamino-N-carbamimidoyl-6-chlorpyrazin-2-carbamide), aminoguanidine, amitrol (3-amino-1,2,4-triazole), nitroguanidine, argininosuccinate, barettin ((2S,5Z)-cyclo-[(6-brom-8-en-tryptophan)-arginine]), lysine, chlorhexidine (1,1'-hexamethylenbis[5-(4-chlorphenyl)-biguanide]), cimetidine (2-cyan-1-methyl-3-[2-(5-methylimidazol-4-ylmethylsulfanyl)-ethyl]-guanidine, clonidin (2-[(2,6-dichlorphenyl)imino] imidazolidine), clothianidin ((E)-1-(2-chlor-1,3-thiazol-5-ylmethyl)-3-methyl-2-nitroguanidine), 2,4-diaminopyridine, N,N'-di-o-tolylguanidine, guanethidine, kreatin, kreatinin, kyotorphin (L-tyrosyl-L-arginine), lugdunam, (N-(4-cyanophenyl)-N-(2,3-methylendioxybenzyl)guanidinacetic acid, metformin (1,1-dimethylbiguanid), octopin ($N^\alpha$-(1-carboxyethyl)arginine), polyhexanide (polyhexamethylenbiguanide (PHMB)), proguanil (1-(4-chlorphenyl)-5-isopropylbiguanide), sulfaguanidine (4-amino-N-(diaminomethylen) benzensulfonamide), tetrazene (4-amidino-1-(nitrosaminoamidino)-1-tetrazena), L-arginine-4-methoxy-β-naphthylamide, L-arginine-β-naphthylamide, L-argininhydroxamate, L-arginine-p-nitroanilid, N-α-benzoyl-DL-arginine, $N_\omega$-Nitro-L-arginine, robenidin, (1,3-bis[(4-chlorobenzyliden)amino]-guanidine, 1-(2,2-diethoxyethyl) guanidine, 1-(P-tolyl)-guanidine nitrate.

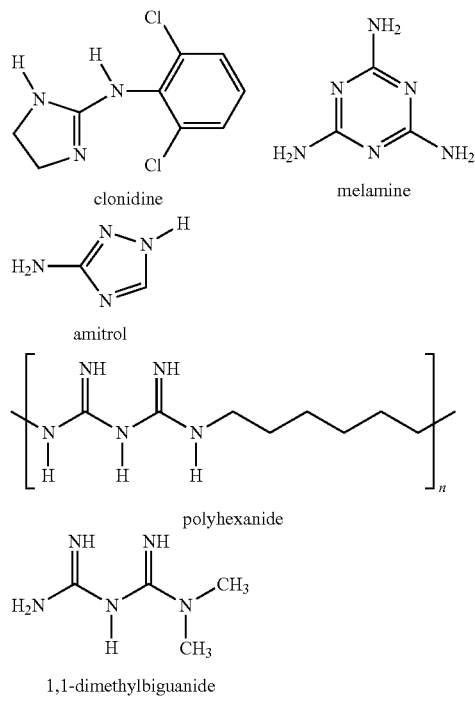

The invention can be effectively used over a broad range of concentration ratios of the solubilizing compound and the fatty acids to be solubilized. Often the fatty acid content of a solution is not exactly known. Therefore the ratio of the solubilizing compound to be added has to be estimated. Inventive solubilization of carboxylic acids and especially fatty acids can be reached when the molar ratio of solubilizing compound to fatty acids (free and bounded) is in the range of 1:1000 to 1000:1. Preferred is a range of 1:100 to 100:1. More preferred is a range of 1:10 to 10:1. Further preferred is a range of 1:2 to 2:1. Most preferred is a ratio of 1:1 to 2:1. It is preferred that the solubilizing compound is used in a molar excess of 3% or 5% or 7% or 8% or 10% or 12% or 15% or 20% or 25% or 30% or 35% or 40% or 45% or 50% or 55% or 60% or 70% or 80% or 90% or 100% or 120% or 140% or 160% or 180% or 200% Moreover a molar ratio of fatty acid to solubilizing compound of 1:1 to 1:200 is preferred. More preferred is a molar ratio of fatty acid to solubilizing compound in the range of 1:1 to 1:100, more preferred of 1:1 to 1:50, still more preferred of 1:1 to 1:30, still more preferred of 1:1 to 1:25, still more preferred of 1:1 to 1:20, still more preferred of 1:1 to 1:15, still more preferred of 1:1 to 1:10, still more preferred of 1:1 to 1:9, still more preferred of 1:1 to 1:8, still more preferred of 1:1 to 1:7, still more preferred of 1:1 to 1:6, still more preferred of 1:1 to 1:5, still more preferred of 1:1 to 1:4, still more preferred of 1:1 to 1:3, still more preferred of 1:1 to 1:2, still more preferred of 1:1 to 1:1.8, still more preferred of 1:1 to 1:1.6, still more preferred of 1:1 to 1:1.5, still more preferred of 1:1 to 1:1.4, also preferred of 1:1 to 1:1.3, also preferred of 1:1 to 1:1.2, also preferred of 1:1 to 1:1.1, also preferred of 1:1 to 1:1.05, also preferred of 1:1.2 to 1:2.8, also preferred of 1:1.4 to 1:2.6, also preferred of 1:1.6 to 1:2.4, also preferred of 1:1.8 to 1:2.2, more preferred of 1:1.9 to 1:2.1 and most preferred is a molar ratio of fatty acid to solubilizing compound in the range of 1.0:2.0. These molar ratios are preferably for solubilizing compounds with one amidino group or one guanidino group. If the solubilizing compound contains two amidino groups or two guanidino groups or one amidino group and one guanidino group only half of the amount of the solubilizing compound is preferably used. Thus in such a case a molar ratio of fatty acid to solubilizing compound of 1:0.5 to 1:25, preferably 1:0.6 to 1:1.4, also preferred of 1:0.7 to 1:1.3, also preferred of 1:0.8 to 1:1.2, also preferred of 1:0.9 to 1:1.1, more preferred of 1:0.95 to 1:1.05 and most preferred is a molar ratio of fatty acid to solubilizing compound in the range of 1.0:1.0.

The solubilization is preferably carried out at a pH value >7.0 and more preferably within a pH range of 7.0 to 9.0. However depending on the medium from which the carboxylic acids should be separated, pH values up to 14 can be used, while a pH range between 7.0 and 8.0 is preferably used if the carboxylic acids should be removed from blood. However, if not complete solubilization is obtained, more solubilizing compound might be added or the pH value might be increased or the aqueous layer might be separated and the extraction process is repeated or a combination of these three possibilities is used.

Some of the solubilizing compounds of the present invention can be represented by the following general formula (I) and formula (II):

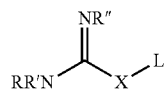
formula (I)

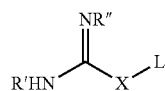
formula (II)

wherein

R', R'', R''' and R'''' represent independently of each other —H, —OH, —CH=CH$_2$, —CH$_2$—CH=CH$_2$, —C(CH$_3$)=CH$_2$, —CH=CH—CH$_3$, —C$_2$H$_4$—CH=CH$_2$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, cyclo-C$_3$H$_5$, cyclo-C$_4$H$_7$, cyclo-C$_5$H$_9$, cyclo-C$_6$H$_{11}$, —PO$_3$H$_2$, —PO$_3$H$^-$, —PO$_3^{2-}$, —NO$_2$, —C≡CH, —C≡C—

CH₃, —CH₂—C≡CH, —C₂H₄—C≡CH, —CH₂—C≡C—CH₃, or R' and R" form together the residue —CH₂—CH₂—, —CO—CH₂—, —CH₂—CO—, —CH—CH—, —CO—CH—CH—, —CH—CH—CO—, —CO—CH₂—CH₂—, —CH₂—CH₂—CO—, —CH₂—CO—CH₂— or —CH₂—CH₂—CH₂—

X represents —NH—, —NR""—, —O—, —S— or —CH₂— or a substituted carbon atom; and

L represents a hydrophilic substituent selected from the group comprising or consisting of —NH₂, —OH, —PO₃H₂, —PO₃, —PO, —OPO₃H₂, —OPO₃H⁻, —OPO₃²⁻, —COOH, -COO⁻, —CO—NH₂, —NH₃⁺, —NH—CO—NH₂, —N(CH₃)₃⁺, —N(C₂H₅)₃⁺, —N(C₃H₇)₃⁺, —NH(CH₃)₂⁺, —NH(C₂H₅)₂⁺, —NH(C₃H₇)₂⁺, —NHCH₃, —NHC₂H₅, —NHC₃H₇, —NH₂CH₃⁺, —NH₂C₂H₅⁺, —NH₂C₃H₇⁺, —SO₃H, —SO₃, —SO₂NH₂, —CO—COOH, —O—CO—NH₂, —C(NH)—NH₂, —NH—C(NH)—NH₂, —NH—CS—NH₂, —NH—COOH, or

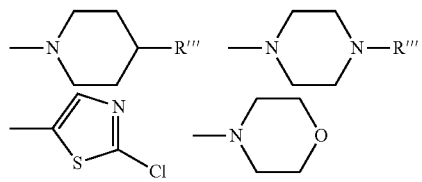

or

L represents a C₁ to C₈ linear or branched and saturated or unsaturated carbon chain with at least one substituent selected from the group comprising or consisting of —NH₂, —OH, —PO₃H₂, —PO₃H, —PO₃²⁻, —OPO₃H₂, —OPO₃H, —OPO₃², —COOH, —COO⁻, —CO—NH₂, —NH₃⁺, —NH—CO—NH₂, —N(CH₃)₃⁺, —N(C₂H₅)₃⁺, —N(C₃H₇)₃⁺, —NH(CH₃)₂⁺, —NH(C₂H₅)₂⁺, —NH(C₃H₇)₂⁺, —NHCH₃, —NHC₂H₅, —NHC₃H₇, —NH₂CH₃⁺, —NH₂C₂H₅⁺, —NH₂C₃H₇⁺, —SO₃H, —SO₃⁻, —SO₂NH₂, —CO—COOH, —O—CO—NH₂, —C(NH)—NH₂, —NH—C(NH)—NH₂, —NH—CS—NH₂, —NH—COOH, or

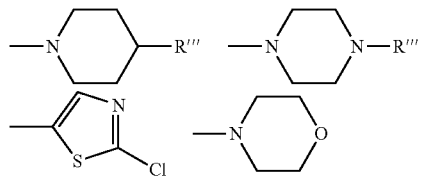

or

L represents a benzene ring and preferably a para substituted benzene ring with at least one substituent selected from the group comprising or consisting of —NH₂, —OH, —PO₃H₂, —PO₃H⁻, —PO₃²⁻, —OPO₃H₂, —OPO₃H, —OPO₃², —COOH, -COO⁻, —CO—NH₂, —NH₃⁺, —NH—CO—NH₂, —N(CH₃)₃⁺, —N(C₂H₅)₃⁺, —N(C₃H₇)₃⁺, —NH(CH₃)₂⁺, —NH(C₂H₅)₂⁺, —NH(C₃H₇)₂⁺, —NHCH₃, —NHC₂H₅, —NHC₃H₇, —NH₂CH₃⁺, —NH₂C₂H₅⁺, —NH₂C₃H₇⁺, —SO₃H, —SO₃, —SO₂NH₂, —CO—COOH, —O—CO—NH₂, —C(NH)—NH₂, —NH—C(NH)—NH₂, —NH—CS—NH₂, —NH—COOH, or

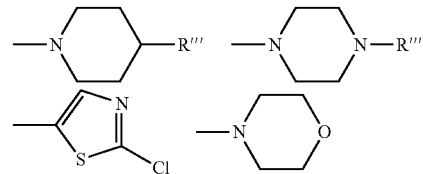

However, such compounds are not preferred and can be excluded from the present application wherein X represents —O— or —S— and L represents —NH₂, —OH, —OPO₃H₂, —OPO₃H, —OPO₃², —NH₃⁺, —NH—CO—NH₂, —N(CH₃)₃⁺, —N(C₂H₅)₃⁺, —N(C₃H₇)₃⁺, —NH(CH₃)₂⁺, —NH(C₂H₅)₂⁺, —NH(C₃H₇)₂⁺, —NHCH₃, —NHC₂H₅, —NHC₃H₇, —NH₂CH₃⁺, —NH₂C₂H₅⁺, —NH₂C₃H₇⁺, —SO₃H, —SO₃⁻, —SO₂NH₂, —CO—COOH, —O—CO—NH₂, —NH—C(NH)—NH₂, —NH—CS—NH₂, —NH—COOH,

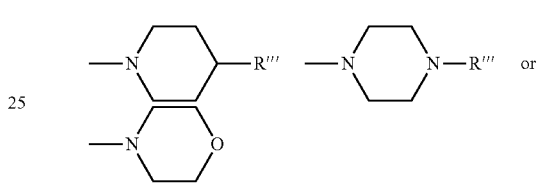

Also excluded are compounds wherein X represents —NH— or —NR""— and L represents —OPO₃H₂, —OPO₃H, —OPO₃², —NH—CO—NH₂, —CO—COOH, —O—CO—NH₂, —NH—C(NH)—NH₂, —NH—CS—NH₂ or —NH—COOH.

The residue L may be further substituted by substituents as defined as $R^1$ to $R^{13}$. The residue L consists preferably of 1 to 10 carbon atoms, more preferably of 1 to 6 carbon atoms and most preferably of 2 to 4 carbon atoms. Carbon atoms of any substituents such as —COOH present on the residue L are included in the aforementioned carbon atom number. Thus the residue L contains a linear or branched carbon atom chain or a phenyl ring which might be substituted with one or more saturated or unsaturated and linear or branched alkyl substituents and/or substituents defined as $R^1$ to $R^{13}$.

It is preferred that the carbon chain of L is in the range of C₁ to C₇, more preferred in the range of C₁ to C₅ and most preferred in the range of C₁ to C₅.

Compounds of general formula (I) or (II) which can be used for solubilizing fatty acids in an aqueous medium or in water are represented by the following formula (I) or (II):

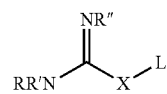

formula (I)

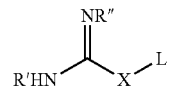

formula (II)

wherein

R', R", R'" and R"" represent independently of each other —H, —OH, —CH=CH₂, —CH₂—CH=CH₂, —C(CH₃)=CH₂, —CH=CH—CH₃, —C₂H₄—CH=CH₂, —CH₃, —C₂H₅, —C₃H₇, —CH(CH₃)₂, —C₄H₉, —CH₂—

CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, cyclo-C₃H₅, cyclo-C₄H₇, cyclo-C₅H₉, cyclo-C₆H₁₁, —PO₃H₂, —PO₃H⁻, —PO₃²⁻, —NO₂, —C≡CH, —C≡C—CH₃, —CH₂—C≡CH, —C₂H₄—C≡CH, —CH₂—C≡C—CH₃, or R' and R" form together the residue —CH₂—CH₂—, —CH=CH— or —CH₂—CH₂—CH₂—

X represents —NH—, —NR""—, O, S or —CH₂— or a substituted carbon atom; and

L represents —CR¹R²R³, —CR⁴R⁵—CR¹R²R³, —CR⁶R⁷—CR⁴R⁵—CR¹R²R³, —CR⁶R⁹—CR⁶R⁷—CR⁴R⁵—CR¹R²R³, —CR⁸R⁹—CR⁶R⁷—CR⁴R⁵—CR¹R²R³, —CR¹²R¹³—CR¹⁹R¹¹—CR⁸R⁹—CR⁶R⁷—CR⁴R⁵—CR¹R²R³;

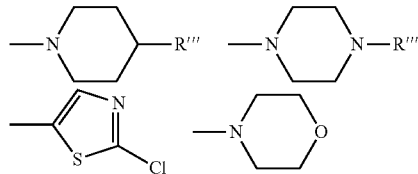

R*, R#, R¹, R², R³, R⁴, R⁵, R⁶, R⁷, R⁸, R⁹, R¹⁰, R¹¹, R¹², R¹³ represent independently of each other the following substituents:

—NH₂, —OH, —PO₃H₂, —PO₃H, —PO₃²⁻, —OPO₃H₂, —OPO₃H, —OPO₃²⁻, —COOH, —COO⁻, —CO—NH₂, —NH₃⁺, —NH—CO—NH₂, —N(CH₃)₃⁺, —N(C₂H₅)₃⁺, —N(C₃H₇)₃⁺, —NH(CH₃)₂⁺, —NH(C₂H₅)₂⁺, —NH(C₃H₇)₂⁺, —NHCH₃, —NHC₂H₅, —NHC₃H₇, —NH₂CH₃⁺, —NH₂C₂H₅⁺, —NH₂C₃H₇⁺, —SO₃H, —SO₂NH₂, —CO—COOH, —O—CO—NH₂, —C(NH)NH₂, —NH—C(NH)—NH₂, —NH—CS—NH₂, —NH—COOH, —H, —OCH₃, —OC₂H₅, —OC₃H₇, -β-cyclo-C₃H₅, —OCH(CH₃)₂, —P(O)(OCH₃)₂, —Si(CH₃)₂(C(CH₃)₃), —OC(CH₃)₃, —OC₄H₉, —OPh, —OCH₂-Ph, —OCPh₃, —SH, —SCH₃, —SC₂H₅, —SC₃H₇, —S-cyclo-C₃H₅, —SCH(CH₃)₂, —SC(CH₃)₃, —NO₂, —F, —Cl, —Br, —I, —P(O)(OC₂H₅)₂, —P(O)(OCH(CH₃)₂)₂, —C(OH)[P(O)(OH)₂]₂, —Si(C₂H₅)₃, —Si(CH₃)₃, —N₃, —CN, —OCN, —NCO, —SCN, —NCS, —CHO, —COCH₃, —COC₂H₅, —COC₃H₇, —CO-cyclo-C₃H₅, —COCH(CH₃)₂, —COC(CH₃)₃, —COCN, —COOCH₃, —COOC₂H₅, —COOC₃H₇, —COO-cyclo-C₃H₅, —COOCH(CH₃)₂, —COOC(CH₃)₃, —OOC—CH₃, —OOC—C₂H₅, —OOC—C₃H₇, —OOC-cyclo-C₃H₅, —OOC—CH(CH₃)₂, —OOC—C(CH₃)₃, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —NHCOCH₃, —NHCOC₂H₅, —NHCOC₃H₇, —NHCO-cyclo-C₃H₅, —NHCO—CH(CH₃)₂, —NHCO—C(CH₃)₃, —NHCO—OCH₃, —NHCO—OC₂H₅, —NHCO—OC₃H₇, —NHCO-β-cyclo-C₃H₅, —NHCO—OCH(CH₃)₂, —NHCO—OC(CH₃)₃, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —N[C(CH₃)₃]₂, —SOCH₃, —SOC₂H₅, —SOC₃H₇, —SO-Cyclo-C₃H₅, —SOCH(CH₃)₂, —SOC(CH₃)₃, —SO₂CH₃, —SO₂C₂H₅, —SO₂C₃H₇, —SO₂-cyclo-C₃H₅, —SO₂CH(CH₃)₂, —SO₂C(CH₃)₃, —SO₃CH₃, —SO₃C₂H₅, —SO₃C₃H₇, —SO₃-cyclo-C₃H₅, —SO₃CH(CH₃)₂, —SO₃C(CH₃)₃, —SO₂NH₂, —OCF₃, —OC₂H₅, —O—COOCH₃, —O—COOC₂H₅, —O—COOC₃H₇, —O—COO-cyclo-C₃H₅, —O—COOCH(CH₃)₂, —O—COOC(CH₃)₃, —NH—CO—NHCH₃, —NH—CO—NHC₂H₅, —NH—CS—N(C₃H₇)₂, —NH—CO—NHC₃H₇, —NH—CO—N(C₃H₇)₂, —NH—CO—NH[CH(CH₃)₂], —NH—CO—NH[C(CH₃)₃], —NH—CO—N(CH₃)₂, —NH—CO—N(C₂H₅)₂, —NH—CO—NH-cyclo-C₃H₅, —NH—CO—N(cyclo-C₃H₅)₂, —NH—CO—N[CH(CH₃)₂]₂, —NH—CS—N(C₂H₅)₂, —NH—CO—N[C(CH₃)₃]₂, —NH—CS—NH₂, —NH—CS—NHCH₃, —NH—CS—N(CH₃)₂, —NH—CS—NHC₂H₅, —NH—CS—NHC₃H₇, —NH—CS—NH-cyclo-C₃H₅, —NH—CS—NH[CH(CH₃)₂], —NH—CS—NH[C(CH₃)₃], —NH—CS—N(cyclo-C₃H₅)₂, —NH—CS—N[CH(CH₃)₂]₂, —NH—CS—N[C(CH₂)₂]₂, —NH—C(=NH)—NH₂, —NH—C(=NH)—NHCH₃, —NH—C(=NH)—NHC₂H₅, —NH—C(=NH)—NHC₃H₇, —O—CO—NH-cyclo-C₃H₅, —NH—C(=NH)—NH-cyclo-C₃H₅, —NH—C(=NH)—NH[CH(CH₃)₂], —O—CO—NH[CH(CH₃)₂], —NH—C(=NH)—NH[C(CH₃)₃], —NH—C(=NH)—N(CH₃)₂, —NH—C(=NH)—N(C₂H₅)₂, —NH—C(=NH)—N(C₃H₇)₂, —NH—C(=NH)—N(cyclo-C₃H₅)₂, —O—CO—NHC₃H₇, —NH—C(=NH)—N[CH(CH₃)₂]₂, —NH—C(=NH)—N[C(CH₃)₃]₂, —O—CO—NHCH₃, —O—CO—NHC₂H₅, —O—CO—NH[C(CH₃)₃], —O—CO—N(CH₃)₂, —O—CO—N(C₂H₅)₂, —O—CO—N(C₃H₇)₂, —O—CO—N(cyclo-C₃H₅)₂, —O—CO—N[CH(CH₃)₂]₂, —O—CO—N[C(CH₃)₃]₂, —O—CO—OCH₃, —O—CO—OC₂H₅, —O—CO—OC₃H₇, —O—OO—O-cyclo-C₃H₅, —O—CO—OCH(CH₃)₂, —O—CO—OC(CH₃)₃, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, cyclo-C₃H₅, cyclo-C₄H₇, cyclo-C₅H₉, cyclo-C₆H₁₁, cyclo-C₇H₁₃, cyclo-C₅H₁₅, -Ph, —CH₂-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₇, —C₃H₅—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH=CH₂, —CH=C(CH₃)—CH=CH—CH₃, —CH=CH—C(CH₃)=CH₂, —C₄H₅—CH=CH₂, —C₃H₆—CH=CH—CH₃, —C₂H₄—CH=CH—C₂H₅, —CH₂—CH=CH—C₃H₇, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—C(CH₃)₂, (CH₃)=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH₂, —CH=CH—C₂H₄—CH=CH₂, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH=CH—CH₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —C₃H₆—C≡C—CH₃, —CH₂—CH=CH—CH=CH—CH₃, —CH=CH—CH=CH—C₂H₅, —CH₂—CH=CH—C(CH₃)=CH₂, —CH₂—CH=C(CH₃)—CH=CH₂, —CH₂—C(CH₃)=CH—CH=CH₂, —CH(CH₃)—CH₂—C≡CH, —CH(CH₃)—CH=CH—CH=CH₂, —CH=CH—CH₂—C(CH₃)=CH₂, —CH(CH₃)—C≡C—CH₃, —CH=CH—CH(CH₃)—CH=CH₂, —CH=C(CH₃)—CH₂—CH=CH₂, —C₂H₄—CH(CH₃)—C≡CH, —C(CH₃)=CH—CH₂—CH=CH₂, —CH=CH—CH=C(CH₃)₂, —CH₂—CH(CH₃)—CH₂—C≡CH, —CH=CH—C(CH₃)=CH—CH₃, —CH=C(CH₃)—CH=CH—CH₃, —CH₂—CH(CH₃)—C≡CH, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₅—C≡CH, —C₂H₄—C≡C—C₂H₅, —CH₂—C≡C—C₃H₇, —C≡C—C₄H₃, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —CH₂—CH(C≡CH)₂, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C(C≡CH)₂—CH₃, —C≡C—CH(CH₃)—C≡CH, —CH(CH₃)—C≡C—C≡CH, —CH(C≡CH)—CH₂—C≡CH, —CH(C≡CH)—C≡C—CH₃, —CH=CH-Ph, —NH—CO—CH₂—COOH, —NH—CO—C₂H₄—COOH, —NH—CO—CH₂—NH₂, —NH—CO—C₂H₄—NH₂, —NH—CH(COOH)—CH₂—COOH, —NH—CH₂—COOH, —NH—C₂H₄—COOH, —NH—CH(COOH)—C₂H₄—COOH, —NH—CH(CH₃)—COOH;

wherein preferably at least one of the substituents R*, R#, R¹, R², R³, R⁴, R⁵, R⁶, R⁷, R⁸, R⁹, R¹⁰, R¹¹, R¹², R¹³ is selected from the following substituents:
—NH₂, —OH, —PO₃H₂, —PO₃H, —PO₃²⁻, —OPO₃H₂, —OPO₃H, —OPO₃²⁻, —COOH, —COO⁻, —CO—NH₂, —NH₃⁺, —NH—CO—NH₂, —N(CH₃)₃⁺, —N(C₂H₅)₃⁺, —N(C₃H₇)₃⁺, —NH(CH₃)₂⁺, —NH(C₂H₈)₂⁺, —NH(C₃H₇)₂⁺, —NHCH₃, —NHC₂H₅, —NHC₃H₇, —NH₂CH₃⁺, —NH₂C₂H₅⁺, —NH₂C₃H₇⁺, —SO₃H, —SO₂NH₂, —CO—COOH, —O—CO—NH₂, —C(NH)—NH₂, —NH—C(NH)—NH₂, —NH—CS—NH₂, —NH—COOH Preferred are also compounds of the general formula (III) as shown below:

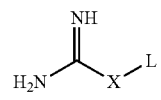

wherein the residues X and L have the meanings as disclosed herein.

Preferably the compounds of general formula (I), (II) and (III) have a partition coefficient between n-octanol and water (also known as $K_{OW}$ or octanol-water-partition coefficient) of $K_{OW}$<6.30 (log $K_{OW}$<0.80), preferably $K_{OW}$<1.80 (log $K_{OW}$<0.26), more preferably $K_{OW}$<0.63 (log $K_{OW}$<−0.20) and most preferably $K_{OW}$<0.40 (log $K_{OW}$<−0.40).

Moreover the compounds of general formula (I), (II) and (III) have the same preferred carbon atom number as disclosed above, the same preferred pH range for the solubilization reaction, the same preferred molar ratio of carboxylic acid to solubilization compound and the same preferred reaction conditions as disclosed above for the solubilization compounds in general.

The partition coefficient is a ratio of concentrations of the un-ionized compound between the two solutions. To measure the partition coefficient of ionizable solutes, the pH of the aqueous phase is adjusted such that the predominant form of the compound is un-ionized. The logarithm of the ratio of the concentrations of the un-ionized solute in the solvents is called log P:

$$\log P_{oct/wat} = \log\left(\frac{[solute]_{octanol}}{[solute]_{water}^{un-ionized}}\right)$$

The distribution coefficient is the ratio of the sum of the concentrations of all forms of the compound (ionized plus un-ionized) in each of the two phases. For measurements of the distribution coefficient, the pH of the aqueous phase is buffered to a specific value such that the pH is not significantly perturbed by the introduction of the compound. The logarithm of the ratio of the sum of concentrations of the various forms of the solute in one solvent, to the sum of the concentrations of its forms in the other solvent is called log D:

$$\log D_{oct/wat} = \log\left(\frac{[solute]_{octanol}}{[solute]_{water}^{ionized} + [solute]_{water}^{neutral}}\right)$$

In addition, log D is pH dependent, hence the pH must be specified at which log D was measured. Of particular interest is the log D at pH=7.4 (the physiological pH of blood serum). For un-ionizable compounds, log P=log D at any pH.

Arginine

Arginine (2-amino-5-guanidinopentanoic acid) is an α-amino acid. The amino acid side chain of arginine consists of a 3-carbon aliphatic straight chain, the distal end of which is capped by a complex guanidinium group. According to the invention, L-arginine, D-arginine as well as racemates thereof can be used.

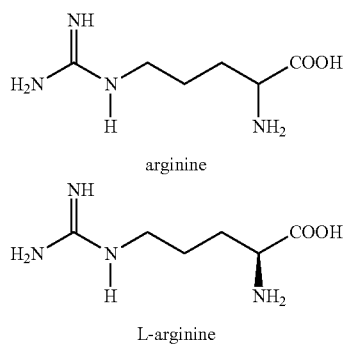

With a $pK_a$ of 12.48, the guanidinium group is positively charged in neutral, acidic and even most basic environments, and thus imparts basic chemical properties to arginine. Because of the conjugation between the double bond and the nitrogen lone pairs the positive charge is delocalized, enabling the formation of multiple H-bonds. Arginine can be protonated carrying three additional charges, located at the side chain ($pK_a$ 12.48), at the amino group ($pK_a$ 8.99), and at the carboxyl group ($pK_a$ 1.82)

The L-form is one of the 20 most common natural amino acids. In mammals, arginine is classified as a semiessential or conditionally essential amino acid, depending on the developmental stage and health status of the individual. Infants are unable to meet their requirements and thus arginine is nutritionally essential for infants.

Arginine is an amphiphilic molecule with a reactive carboxy group.

The literature value for the log $P_{ow}$ (see above) of arginine is −4.20. For arginine the distribution coefficient approximately equals the partition coefficient because at pH=7 arginine is nearly exclusively present in the ionic form. Libby et al. (Mol Pharmacol 1981, 20, 602-608) determined log $D_{ow}$=−4.08.

When investigating the solubilization capacity of fatty acids by aqueous amino acid systems it was found that arginine completely dissolves oleic acid by formation of micro- and nanoemulsions when exceeding a molar ratio of 1:1 (arginine:fatty acid). Interestingly, no co-solvent is necessary to solubilize the carboxylic acids. Spontaneous formation of a nanoemulsion was observed at ambient temperature. The pH value after self-assembly of a 1:1 microemulsion is about 9.8. In nanoemulsions the particle size was found to be about 2 nm in diameter and no aggregates larger than 25 nm were found. This self-assembly of nanoparticles is a central characteristic of a nanoemulsion. The nanoemulsion is completely transparent and stable over more than 6 months at temperatures between −20 and 100° C. Decrease of pH by addition of acid (HCl) reduces the solvation capacity which could be overcome by addition of arginine. However, the pH of the solution is critical for the nanoemulsification capacity of arginine which decreases below pH 8.

Surprisingly, it was found that arginine exhibits its solubilizing capability in organic solutions also. Albumin and oleic acid at various concentrations in an aqueous solution were investigated by adding arginine. Excess of fatty acids results in blurring of the solution. By addition of arginine this effect can be completely reversed. Equilibrium dialysis was performed without and with arginine. It could be shown that the transfer of fatty acids through a 5000 D cellulose membrane was up to 10 times higher when arginine was in the model solution. The same investigations performed with human plasma showed comparable results (Example 1). The capacity of arginine to liberate fatty acids bound to albumin was investigated by $^3$H-labeled oleic acid. Without arginine about 40% of the radiolabeled fatty acid resides in the organic phase after extraction with n-hexane. Addition of arginine liberated fatty acids. However, a higher molar concentration of arginine than that of the fatty acid was necessary to achieve the maximum effect. A reduction of residual fatty acids down to 2% could be achieved. The efficacy was enhanced when the temperature was increased to 38° C., as compared to room temperature. Other hydrophilic amino acids (lysine, asparagine, asparaginic acid, glutamine, glutaminic acid, histidine) as well as hydrophobic amino acids investigated by an identical procedure yielded also a reduction of residual fatty acids. However, this was significantly less, as compared to arginine.

Derivatives of Arginine as Solubilizing Compounds

The term "derivatives of arginine" refers to compounds having a carboxy group (—COOH) and a amidino group ($H_2N$—C(NH)—) or substituted amidino group separated by at least one carbon atom or having a carboxy group (—COOH) and a guanidino group ($H_2N$—C(NH)—NH—) or a substituted guanidino group separated by at least one carbon atom. The above mentioned compounds of general formula (I) are also derivatives of arginine.

Examples for derivatives of arginine are for instance amidinoacetic acid, amidinopropionic acid, amidinobutyric acid, guanidinopropionic acid, guanidinobutyric acid, oligoarginine, polyarginine, as well as

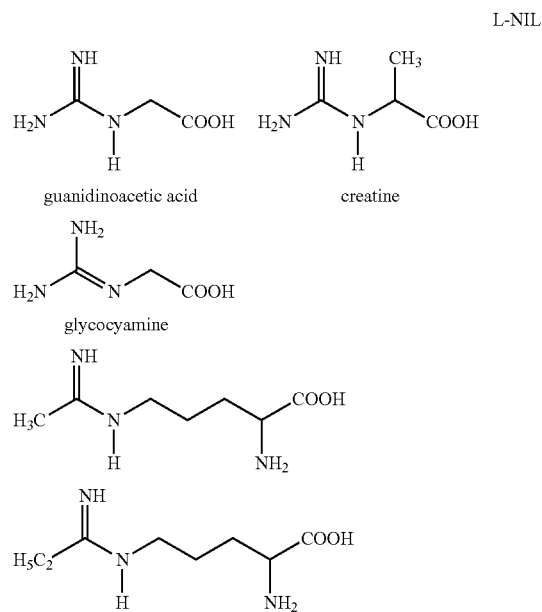

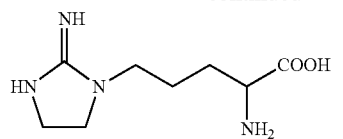
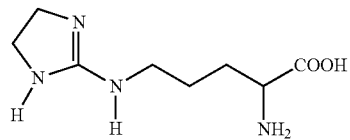
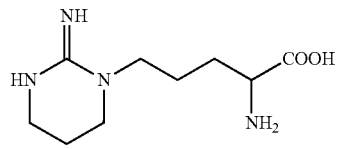
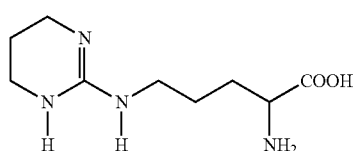
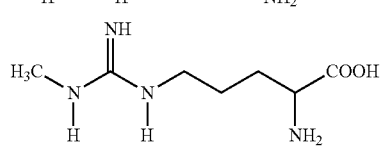
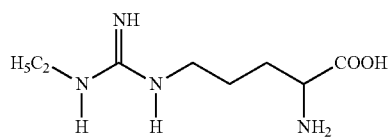
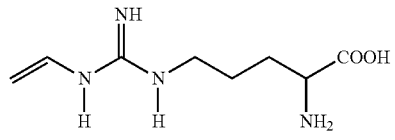
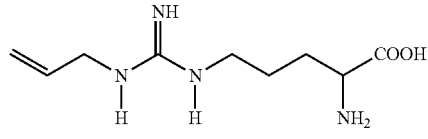
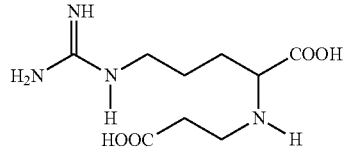
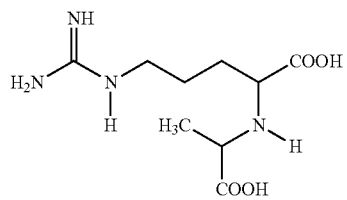
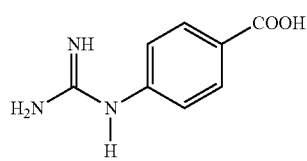

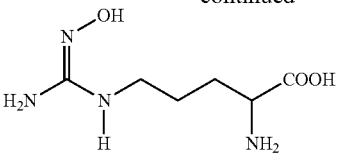
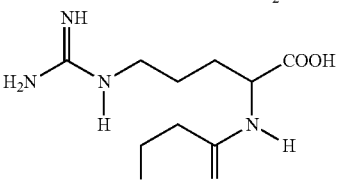
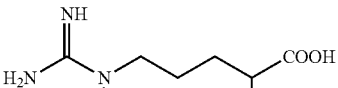
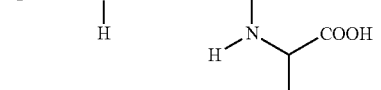
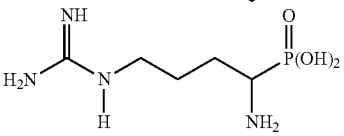
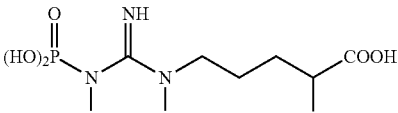
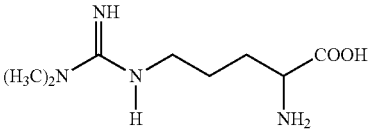
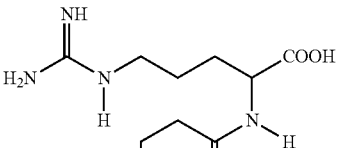
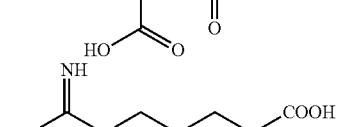
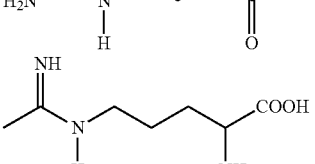

Interaction of Carboxylic Acids and the Solubilizing Compound

According to the invention a preferred method for removing carboxylic acids from aqueous or organic solutions comprises the following key steps:

a) Adding the solubilizing compound to a fatty acid-containing solution;

b) Passing the solution along a surface which carries immobilized lipases or catalysts capable to release fatty acids from their esterified forms and which is implemented in a micro- or nanofluidic capillary system to obtain complete interaction with the esterified fatty acids;

c) Passing the solution along an interphase consisting of a separation membrane, a gel, or a hollow capillaries assembly d) Applying a gradient across the phase separation interface by means of a concentration gradient, an osmotic gradient, a physico-chemical gradient, a pH gradient, a pneumatic gradient, a temperature gradient, an electric gradient or a combination thereof;

e) Separating the fatty acid fraction associated with the solubilizing compound;

f) Dissolving the fatty acids in an acceptor medium; and g) optionally removing the solubilizing compound from the solution.

Thus the capability of a solubilizing compound to build micro- and nanoemulsions from carboxylic acids in aqueous or organic media is basic for the present invention. This fundamental principle can be used to a variety of medical, pharmaceutical, biochemical, industrial and environmental applications which shall be described in the following.

Formulation of Solubilizing Compounds

The solubilizing compound can be used as pure solution, pH-adjusted solution or complexed solution. It can be bound electrostatically or covalently to a peptide or protein, as well as to a negatively charged organic or inorganic polymer or surface.

The solubilizing effect can be enhanced by reducing the ionic strength of the solution, emulsion or oil to be treated or analyzed e.g. by means of chelation, dialysis or electrodialysis in order to reduce the cation concentration. Furthermore, it can be useful to alter the binding energy of an electrostatic carboxylic acid—protein interaction of the carboxylic acid to be purified by changing the protein surface energy or by thiolysation of sulfide bonds, therewith alternating the steric conformation of the protein. As set forth in the examples it could be shown for a solubilizing compound such as arginine that there is a spontaneous and stoichometric formation of an adduct of arginine and ionized hydrophobic substances, in particular fatty acids under suitable circumstances. Mini-, micro- or nanoemulsions result.

According to the invention these mini-, micro- or nanoemulsified carboxylic acids can be separated, resp. extracted from aqueous or organic media by 1. an adsorption of the substance to be separated on surfaces such as aerolithes, spheres, microbeads or ceolites, particularly if they display surface characteristics enabling them to electrostatic or covalent bonds with the substance to be separated;
2. complexation i.e. formation of salts
3. a diffusion of the substance to be separated into an acceptor medium (in particular organogels);
4. a dialysis of the substance to be separated by means of a thermic, electric or physico-chemical gradient;
5. a filtration of the substance to be separated by means of a thermic, electric or physico-chemical gradient;
6. distillation techniques,
7. supercritical liquid extraction,
8. nanofluidic separation techniques.

Hemodialysis

Hemodialysis is a procedure to purify blood and is a method for treating patients suffering from kidney malfunction. The principle of dialysis is the diffusion of solutes across a semipermeable membrane (osmosis), whereby blood/plasma with water soluble toxins, electrolytes, urea and other substances is on one side of the membrane (permeate) and a dialysis solution consisting of water and a number of important electrolytes at physiological concentrations on the other side (dialysate). Small molecules such as water, electrolytes, urea and urates diffuse through small holes in the membrane along the concentration gradient, but not proteins and blood cells. In hemodialysis the blood is pumped from the patient, flows along the membrane in the dialyser, and the cleaned blood (retinate) is pumped back into the patient. The countercurrent flow of blood and dialysate maximizes the concentration gradient of solutes between blood and dialysate.

The dialysis solution is prepared by mixing a concentrate solution of electrolytes and a buffer system with sterile deionized water (dialysate). The dialysate is warmed, and freed from gas. There are basically two different mixing systems. In the volumetric mixing system two fix adjusted pumps mix the concentrate and the water so that the amount of flow and the concentration of the dialysis solution do not change. The conductivity is a measure for the concentration of electrolytes in the solution. After mixing the conductivity of the solution is measured and the pumps are adjusted by hand if necessary to change the amount of water or concentrate.

The dialysis machines usually provide the following functionalities:
  aspiration of the blood from the patient by means of roller pumps
  anticoagulation
  transport processes through the dialyser(s)
  control of flow velocity of the dialysate and the filtrate
  control of pressure gradients between dialysate and filtrate circulation
  control of conductivity
  adjustment of ionic strength and pH
  removal of entrapped air and particles
  tempering of the recirculating blood
  recirculation of blood to the patient by means of roller pumps Electrolytes, urea, kreatinine, phosphate, amino acids, pharmacological active substances and water are able to pass semipermeable membranes as used in hemodialysis.

B. DEFINITIONS

"Dialyser" means a device containing a phase separation interface allowing diffusion and permeation of carboxylic acids in a solution from one side of the separation interface to the other into another solution by means of a physical and/or chemical gradient.

"Extractor" means a device containing materials that allow physical and/or chemical interaction of carboxylic acids with an interface thereby adsorbing, and/or absorbing, and/or complexing and/or separating them.

"Capillary voids" are continuos, linear, tubular-shaped open spaces within a material.

"Porous" refers to the characteristics of a material having pores, openings or recesses that allows the passage of defined molecules from one compartment to another compartment along a gradient. These pores, openings or recesses can be uniform or diverse in size, shape and distribution throughout the material, preferably a membrane.

The term "blood" as mentioned herein refers to blood, whole blood, blood plasma and serum.

It is noted that the term "blood" may also refer to blood components and blood substitutes herein.

The term blood components as used herein are cellular and acellular components, comprising red and white blood cells, thrombocytes, proteins and peptides, as well as lipid fractions.

The term "blood substitutes" as used herein refers to blood substitutes which can at least partially carry oxygen and volume expanders used to increase the blood volume which supports the blood circulation but can not achieve the physiological function of the blood.

The term "subject" refers to any mammal including humans. Humans are preferred.

The term "first inlet", "second inlet", "third inlet", "fourth inlet" etc. have to be understood as the number of inlets of the device and not as the number of inlets of a part of the device such as one chamber of the device. Thus "fourth inlet of second chamber" does not mean that the second chamber has four inlets but that the second chamber has inlet No. 4 of the device.

The term microemulsion as used herein refers to the characteristics of an emulsion of the inventive solubilizing compound and a carboxylic acid that comprise at least two of the following:

Spontaneous self-assembly, optical translucency, turbidity <1.1 $cm^{-1}$, >80% of micelles being <200 nm at 25° C., stability of optical translucency in a temperature range between −40 and 99° C., stability of optical translucency for at least 12 months, surface tension <60 dyn/s.

The term nanoemulsion as used herein referred to the characteristics of an emulsion of the inventive solubilizing compound and a carboxylic acid that comprise at least two of the following:

Spontaneous self-assembly, optical transparency, turbidity <0.4 $cm^{-1}$, >80% of micelles being <100 nm at 25° C., stability of optical transparency in a temperature range between −40 and 99° C., stability of optical transparency for at least 12 months, surface tension <50 dyn/s

C. METHODS FOR THE SEPARATION AND REACTION OF FREE CARBOXYLIC ACIDS FROM AQUEOUS OR ORGANIC MEDIA

Separation of free carboxylic acids can be accomplished by physical or chemical methods as known in the art. This includes but is not restricted to one or a combination of the following methods: adsorption, complexation, filtration, dialysis, evaporation, segregation by gravity, electrophoresis, electrolytically, electroosmotically, electrokinetically, osmotically, thermally, by a concentration gradient, or by a chemical reaction.

It is preferred that the separation is carried out by adsorption, filtration, dialysis, electrolysis, as well as complexation and segregation by gravity.

Methods to Use the Nano-Emulsifying Effect

The nano-emulsifying effect of the solubilizing compound on carboxylic acids enables their solvation and purification in aqueous media, enables their use as an electrolyte, enables chemical reactions in aqueous media, enhances chemical reactivity, increases the dissolution capacity of carboxylic acids for hydropohbic and lipophilic substances. Nanoemulsification enables, respectively enhances the dissolution and penetration of carboxylic acids into molecular complexes, and organic or inorganic solids. Furthermore, it can be used to dissolve complexes of carboxylic acids with apolar or amphiphilic molecules in organic media or emulsions.

Nanoemulsification

The term nanoemulsification refers to the formation of nanoemulsions. They can be used in a wide variety of applications. The optimal solubility of the two phases in aqueous media, the large surface area between both phases, as well as the dimensions and geometrical structures of these phases in the nanometer range make them a versatile vehicle to dissolve reactants, chemicals or pharmaceuticals. Solubilizing compounds such as arginine or arginine derivatives have been shown to be a valuable additive in several communications reporting about nanoemulsions. However, the sole use of such solubilizing compounds for preparing a nanoemulsion has not been documented so far.

Methods for Complexation and Adsorption

Carboxylic acids that have been solubilized in an aqueous medium can be further processed by separating them by means of complexation or adsorption. In aqueous media, materials for complexation should be proton donors with a capacity to build salts with carboxylic acids. A preferred embodiment is the use of calcium salts.

Adsorbers can be used in hydrophilic or hydrophobic media, they may have hydrophilic or hydrophobic properties, be present in a solved form or immobilized on a support material. Materials to be used are listed below (5. Acceptor-/adsorbent-molecules/materials). In a preferred embodiment carbon, immobilized arginine or calcium is used. For adsorption or complexation of fatty acids it can be necessary to protonize them in an organic aqueous medium or to deprotonize them in an organic solvent. By doing so, they can be easily adsorbed in an organic aqueous medium or solvent. A preferred embodiment is the use of n-hexan, triglycerides or cholesterol.

Methods to Use Fluid-Fluid Separation Procedures

The inventive solubilisation effect can further be used to separate carboxylic acids from organic media by means of a fluid-fluid extraction as known in the art. The principle of this method is the spontaneous or driven separation of the aqueous and organic phases. To separate or remove carboxylic acids solved within the organic phase an aqueous solution containing the solubilizing compound is mixed with the organic phase. This mixing can be performed using various physical means like shaking, stirring, vibrating, sonificating, heating, bubbling, steaming, as well as by means of laminar or turbulent fluid dynamics. Solubilized carboxylic acids are carried away with the aqueous medium, thereby separated and concentrated in the aqueous solution. Phase separation can be accomplished by gravity which can be forced by physical means like centrifugation or sonification. For the extraction of thus separated carboxylic acids the aqueous or organic solution is removed by standard methods. The dissolved carboxylic acids can be separated by acidification of the solution and extraction with an organic solvent. Conversely, carboxylic acids dissolved in an organic solvent can be transferred or released to an aqueous medium by extraction with the inventive solubilizing compound(s). This method can be used for preparation and analytics or applied to large-scale industrial plants.

Electrokinetic and Electrophoretic Methods

A preferred embodiment is the electrophoretic separation of carboxylic acids. Carboxylic acids are weak electrolytes. Their ionic strength corresponds to their CMC in an aqueous system because of their low partition. Ionic and anionic detergents have shown to increase partition by reducing the CMC. However, a higher ionic strength is reached by ionic surfactants or the presence of counter ions only. Theoretically, a counter ion that hinders micellation would lead at the same time to an optimal partition and an even better partition when the dissociation constant of the ion pair binding is high. Detailed analyses of the partition of carboxylic acids in nanoemulsions are lacking. Surprisingly, it was found that the solubilizing compounds exhibit these properties. Moreover, they solubilized carboxylic acids and allow an unexpectedly high electrophoretic mobility of the carboxylic acids. It is likely that the lower adherence between the carbon chains of the carboxylic acids during the interaction with such a molecule is responsible for the observed mobility. Thus, nanoemulgation of solubilizing compounds and carboxylic acids enable their electrophoresis in aqueous media or organic media. Furthermore, these obubilizing compounds make carboxylic acids suitable for electrophoretic analytics and separation procedures as known in the art. A preferred embodiment is the use in gel electrophoresis. Hydro- or organogels are suitable. Detection of the electrophoretically separated carboxylic acids can be done by the use of an inorganic chromophore, i.e. chromate (254 nm), molybdate (230 nm), or aromatic acids with strong UV chromophores, i.e. phtalic, trimellitic, pyromellitic, benzoic, pyridinedicarboxylic acid, cupric-accetat-pyridine and 4-aminobenzoate, by techniques known in the art.

Another preferred embodiment is the use in electro-osmosis, -dialysis, and -filtration. Carboxylic acids exhibit the tendency to form micelles in aqueous media, as said before. In organic solvents they move freely. However, since they are protonated in organic solvents electrokinetic movement is not possible. When present as a salt in an aqueous medium the electrophoretic motility is poor. Furthermore, although carboxylic acids are usually small molecules due to micelle formation they pass filtration media only to a small extent. This finding is aggravated due to the fact that available filter materials are either hydrophilic or hydrophobic. These properties, however, are not ideal for the partition of carboxylic acids. Therefore, electro-osmosis, -dialysis, and -filtration is ineffective for this purpose.

Surprisingly, the use of an inventive solubilizing compound leads to micro- or nanoemulgation of carboxylic acids and allows their separation by means of osmosis, dialysis, filtration, distillation or supercritical fluid extraction using a concentration gradient, a thermic gradient, an electrical gradient, a physico-chemical gradient or a combination thereof. In a preferred embodiment an organophilic separation membrane is used. Said membranes should have a high proportion of organic molecules when used for osmosis or dialysis, or the surface of filter channels should exhibit a high content of lipophilic molecules.

However, separation media exhibiting such properties are lacking. Surprisingly, the inventor found that transport capacity and selectivity for the carboxylic acids can be increased by selection of molecules at the surface of the separation media while reducing the pore/channel dimensions.

The mechanism of the inventive procedure is believed to be the combination of said effects: I.e., the high partition of carboxylic acids and the high dissociation rate of arginine or the other solubilizings compounds enable a fast movement in the electrical field. Eletrokinetic flow occurring within nanochannels can further increase the electrophoretic transport capacity.

Nanofiltration Methods

Carboxylic acids have a low molecular weight and small dimensions. Therefore they are principally suitable for nanofiltration. However, the low concentration of free carboxylic acids in an aqueous medium makes nanofiltration ineffective. Furthermore, membranes selective for hydrophobic or lipopholic substances are unsuitable or lacking. The inventive solubilization of fatty acids increases the fraction of free carboxylic acids and enables their nanofiltration. In recent years, nanofiltration membranes have become commercially available. However, their surfaces are hydrophilic making them unsuitable for carboxylic acids. Hydrophobisation of channel surfaces had only little effect on their filtration rates. Since nanofiltration would offer decisive advantages over the use of micro- or ultrafiltration membranes like higher substrate specifity or increased flux, efforts have been made to improve partition of carboxylic acids in the nanochannels. Therefore surface functionalization of the nanochannels was intented in order to render them lipophilic. This objective could be achieved by several molecular classes: Amino acids, polypeptides and carboxylic acids (see Chapter E, 4. Materials for surface functionalization).

Therefore, a preferred embodiment is the use of a nanofiltration membrane having a functionalized surface exhibiting low hydrophilic (contact angle for water >100° at 25° C.) and a high liphphilic (contact angle for oleic acid <10° at 25° C.) properties. Mean channel width should be in the range of 5 to 100 nm, more preferently between 10 and 50 nm. Channel length should be in the range of 0.1 to 10 µm, more preferably between 2 and 5 µm. Materials that can be used are listed below (Chapter E, 3.3 Separation membranes materials).

Preferred materials are aluminium oxide, titanium oxide, carbon, polycarbonate, polyethylene, silicates.

In a preferred embodiment surface functionalization should be preceded by monolayer coating of the channel surface with a polymer suitable to react with the molecules used for functionalization called connecting layer and molecules to be attached to this layer determining the surface properties, called functionalization layer.

1. Connecting Layer

This layer acts as an interface between the given support material and the functionalization layer. It can be necessary to introduce or activate molecular structures at the support material first. The connecting layer should completely cover the surface, which should be smooth after processing. There should be a dense count of reactive groups appropriate for reaction with molecules of the functionalization layer. However, a defined multilayer coating can be advisable in order to shape the channel structures. This can be accomplished by polymers, as given below (Chapter E, 3.3 Separation membranes materials).

A preferred embodiment is the use of polymers such as APTS, pentafluorophenyl acrylate (PFA), pentafluorophenyl methacrylate (PFMA), poly-N-trimethyl-aminoethyl methacrylate (PTMAEMA) and poly(2-dimethylamino)ethyl methacrylate (PDMAEMA).

2. Functionalization Layer

This layer aims to accomplish defined surface conditions. The preferred surface condition resulting from the sum of intermolecular forces of Coulomb, van der Weals, hydrogen bonds and hydrophobic interaction of the inventive surface functionalization has a net lipophillic effect allowing partition of carboxylic acids. Interposition of charged groups creating a surface charge, which could be positive or negative, is used in a preferred embodiment. A further preferred embodiment is the institution of a lipophillic or hydrophobic surface force ranging 2-20 nm while having a neutral or positive surface charge. Suitable molecules can be carboxylic acids, amino acids, peptides, proteins, ternary or quaternary amides, aromatic hydrocarbons or cyclodextrins. (see Chapter E, 4. Materials for surface functionalisation).

In a preferred embodiment fatty acids, alanine, phenylalanine, arginine, lysine, amidine or guanidine are used as a central functional group within a molecular structure.

Thus the present invention also refers to an ultra- or nanofiltration separation panel for dialysing, filtrating or nanofiltrating carboxylic acids that is functionalized with one or more of the substances general formula (I) or (II) comprising at least a functionalization layer and optionally a connection layer.

D. APPLICATIONS OF THE INVENTIVE SOLUBILISATION PROCEDURE

Dialysis of Blood Fatty Acids

Dialysis is a standard procedure in medicine, analytics and in the chemical or pharmaceutical industry. The procedure is used to reduce or eliminate substances from a feed solution by a gradient driven passage through an interface. The interface mostly consists of a porous membrane which allows the passage of molecules up to a defined size. Available membranes vary in their hydrophilic and hydrophobic properties. However, the passage of free carboxylic acids is only possible in neglectable amounts. One reason for that is that the amount of free fatty acids is small even in the presence of high concentrations of detergents, since micelles are still present resulting in a particle size that does not allow their passage through membrane pores. This problem can be overcome by the inventory formation of a micro- or nanoemulsion. The inventive method can be carried out by a modification of a conventional blood dialysis, e.g. a subject's blood system is coupled to the dialyser via tubings. Alternatively, a certain amount of blood is taken as a sample, processed in a modified dialyser according to the inventive method, and afterwards reinfunded into the patient. In the latter case the volume of the taken blood sample is in the range of 10 ml to 0.5 l, preferred between 100 and 500 ml, more preferred between 300 and 500 ml.

It has to be stressed that all methods disclosed in the present invention can be performed in-vivo, i.e. on the human and animal body and in-vitro, i.e. not on the human and animal body.

In a preferred embodiment the inventive method is used for removing free fatty acids from the blood of a subject in need thereof. Therefore there are medical and scientific applications of this method. According to the invention a dialyzer, respectively extractor is provided which applies the above described inventive principle to the blood of the subject. For this aim the inventive device is coupled to the venous or arterial circulation of a mammal, preferably a human by means of canules, catheters and tubes. In some embodiments a commercially available dialysis machine can be used herein, e.g. Plasmat Futura® (BBraun Melsungen, Germany). The blood aspirated by this machine via a venous or arterial tubing or provided by a blood sample can be pumped into the dialysis unit (see schematic drawings in FIG. 2: 213), by means of a roller pump (212), either after or without hemoseparation. The dialysis unit consists of two subunits that are interconnected by appropriate tubings (e.g. Fresenius, Lifeline® Beta SN Set SRBL-R, Germany). The first subunit consists of a diayser as described below (for detailed description see section Dialyses/Extraction procedures). The blood aspirated by the dialysis machine may be pretreated by means of dialysis and or citrate anticoagulation (202) as known in the art, or undergo a hemoseparation procedure or a sequence of these procedural steps. The prepared blood (plasma) is pumped by the dialysis machine into the inlet of the dialyzer (203) along with a constant infusion of the arginine solution or any other solution of a solubilizing compound by means of an infusion pump (214) from a storage sack (215) containing a sterile solution of the solubilizing compound such as arginine. The final concentration of the solubilizing compound in the dialysate can be calculated from the current blood (plasma) flow and the concentration of this compound in the infusion solution. In the case of arginine, a final concentration of 100 to 300 mmol/l is aimed at. When it is dissolved in the distribution chamber of the dialyzer (for detailed descriptions see section Dialyses/Extraction procedures) the mixture, of the solubilizing compound-blood (plasma) solution passes the hollow fiber membranes allowing micro- or nanofluidic conditions. In a preferred embodiment an arrangement of hollow chamber capillaries is used with a typical diameter of 200 µm and a length of 30 cm. The blood (plasma) volume within the separation medium is 40-80 ml, preferably 50-60 ml. The material thereof can be organic, inorganic or combinations of both. Materials that can be used are summarized in the interface material list (see Chapter E, 3.4 Hollow porous capillaries). The membranous interface has micro- or nanopores being molecularly functionalized. Surface, pore and channel functionalization and properties are described below (see Chapter E, 4. Materials for surface functionalization). The duration of the passage of the feed solution should be preferably between 20 to 60 s, more preferably between 30 and 40 s. The resulting contact duration between the feed solution and the interface should grant for a complete removal of solubilized fatty acids. The assembly of such filter cartridges is known in the art. The dialysis liquid is perfused through the dialysate inlet. It fills the space between the exterior of the hollow fibers and the interior wall of the cartridge. The perfusion direction is opposite to that of the feed flow and is called cross-flow in the art. The typical perfusion rate of the dialysing liquid is in the same range as that of the feed liquid. However, it might be necessary to vary the flow rate ratios, that could be typically between 1:2, 1:1, 2:1 or 3:1, in dependence of the lipid concentration in the feed solution. The dialysis liquid leaves the cartridge through the outlet conus and is transferred to a secondary circulation unit which is described below.

The blood (plasma) exits the dialyser by collection in the collection chamber and is transferred via adequate tubing into the second unit. The second unit consists of a standard dialyser used for hemodialysis (201). The blood (plasma) is led through the hollow chamber capillaries within the dialyser permitting concentration equilibration of low molecular hydrophilic molecules and electrolytes against the dialysis solution (210) which is pumped by means of a roller pump (216) and permeates the space between the exterior surface of the fibers and the interior surface of the cartridge. The dialysate exits the standard dialyser by an outlet and is collected in a waste tank (211). The concentration, respectively the ionic strength of the dialysate and the pH is regulated by the dialysis machine. The purified plasma is merged with the blood cells that have been separated (not depicted in FIG. 2). The purified blood is pumped by means of a roller pump (212) back to the patient through the aforesaid catheter system.

Secondary Circulation Unit

As said before the solution within the secondary circulation, herein called acceptor solution, should have a high capacity to bind fatty acids that have passed through the interface of the dialyser (203) and convect them to a further, secondary extraction device (204), herein called fatty acid exchange module. The acceptor solution (see Chapter E, 7. Acceptor solutions) within the secondary circuit can be an aqueous solution with an organic or inorganic acceptor (see Chapter E, 5. Acceptor-/Adsorbent-Molecules/Materials). The acceptor molecules can be dissolved in free form or are immobilized to ceolites or adsorptive surfaces (see Chapter E, 4. Materials for surface functionalization). Preferably, a solution of purified fatty acid binding proteins originating from human source or from synthetic production should be used as an acceptor for fatty acids in the secondary circulation. The acceptor solution of the secondary circulation is moved by a pump (205), preferentially a roller pump. The acceptor solution loaded with fatty acids exits the dialyser via the filtrate outlet by aspiration of a roller pump (205) and is forwarded into the inlet of the fatty acid exchange module (204) through an adequate tubing and perfused through the common exchange chamber filled with the extraction granulate. The acceptor solution is being purified while passing through the extraction granulate, then exits the exchange module by the outlet port and enters a tubing which is connected with the dialyser at the inlet of the filtration chamber.

The carboxylic acid exchange module (see FIG. 3) consists of a cartridge that exhibits two inlets and two outlets located at the opposite sides of the cylindrical cartridge. Inlet (301) and outlet (303) of the secondary circulation are covered by a filter funnel (305) having a pore size below the lower range of the extraction granulate of the exchange circulation. The inlet (302) and outlet (304) for the tertiary circulation are large enough to allow a low pressure in- and out-flow of the granulous extraction material. Within the exchange module the exchange solution of the secondary circulation is in immediate contact with the extraction granulate of the tertiary circulation. Perfusion of the exchange module with the solution of the secondary circulation and with the granulate from the tertiary circulation is directed in opposite direction to one another. The refreshed acceptor solution of the secondary circuit exits through the outlet (303) of the exchange module and is conducted to the filtrate inlet connection of the dialyser via a tubing.

Tertiary Circulation

The tertiary extraction circulation is moved by a pump (see FIG. 2: 205) suitable for the use of the granulous extraction material. Preferentially, a double cylinder pump (207) can be used. Introduction of air into the circulation is reduced by simultaneous filling of the system with small amounts of purified acceptor solution by means of a communication via a tubing that connects the pump with the outlet of the exchange module. A bypass-port of the pump allows simultaneous filling of the system. The extraction material dissolved in the acceptor solution is pushed forward through a tubing which is connected with the inlet of the fatty acid exchange module. Residual air transported within this segment is removed by an air trap (208) mounted on top of an air escape port (217). The port is sealed with a filter plate that does not allow passage of the extraction material. After passaging the exchange module the extraction material exits the cartridge through the outlet of the tertiary circulation. This outlet is connected with a tubing that can be fixed in a vertical position located above the exchange module and the storage vessel for the acceptor solution (209). This tubing is interconnected with the storage vessel which is sealed with a filter plate that does not allow passage of the extraction material (218). However, the acceptor solution is allowed to flow back within this tubing to the approximate hydrostatic level of the filling plane of the storage vessel. The extraction material is pushed forward through the tubing to a container (206). The container is part of a cleaning system for the purification of the extraction material. The purification can be operated by physical or chemical means. The purification process is followed by a final cleaning step using sterile water. The purified extraction material is then collected in a second container being connected with the pump of the tertiary circulation.

Alternatively to purify the extraction material in a tertiary circulation, fresh extraction material can be fed in from a reservoir and discharged into another reservoir after passage of the exchange module using the same tubings as described before.

According to the invention the aforesaid procedure or parts of it can be combined with standard techniques in hemotherapy like dialysis, hemoperfusion, hemofiltration, hemodiafiltration, centrifuge-plasma-separation, plasma-apheresis, cascade-filtration and thermo-filtration.

Herein the separation efficacy is increased by additional hydrolysis of esterified fatty acids, enhancement of lipolysis and/or the use of a central venous blood aspiration site for blood purification Thus one especially preferred embodiment of the present invention is to remove carboxylic acids and especially fatty acids from blood by using the solubilization compounds disclosed herein and preferably arginine and arginine derivatives. The most common method for the purification of blood is dialysis which can also be used to remove fatty acids and also albumin-bound fatty acids from blood.

Formulations of Solubilizing Fluids for Human Use

In a preferred embodiment the solubilization of fatty acids is achieved by the use of an inventive solubilizing compound. It can be applicated in its pure form, or in a solution adjusted for pH with HCl or other acids acceptable for use in humans. The preferred pH range is 7.5-10.0, more preferred between 8.0 and 9.0. It can be advantageous to use an additive as a co-solvent or buffer, as listed below (see Chapter E, 8. Additives for preparations of arginine or its analogues). A preferred additive is ascorbinic acid.

Clinical Use

The inventive method for solvation and extraction of fatty acids from human blood can be applied by standard techniques as know by a person skilled in the art and can be part of a hemodialysis procedure performed in a patient in need thereof due to kidney or liver failure. The use of this procedure can be indicated in other indications too. Medical indications include but are not restricted to diagnoses or conditions such as diabetes mellitus, metabolic syndrome, overweight, obesity, arterial hypertension, hypertriglyceridemia, hypercholesterinemia, hyperuricemia, cellulitis, atherosclerosis, fatty liver, lipomatosis, ventricular premature beats, ventricular tachycardia, supraventricular fibrillation. A preferred embodiment is a venous access site for aspiration and recirculation of blood. The site of aspiration should be within the central venous system, most preferentially within the Vena cava inferior. The purified blood could be returned to the patient via the same access site having the orifice distally to the openings of the aspiration site. This is realized in commercially available catheter systems like BioCath (Bionic Medizintechnik, Friedrichsdorf, Germany). The access system should have a French-size between 8 and 14, more preferentially between 10 and 12. The most preferred venous access site is the Vena femoralis.

Connections and filling of the tubings should be performed as done in hemodialysis and known to persons skilled in the art. Therapeutical anticoagulation is mandatory while performing the procedure. This can be done by co-infusion of heparin or low molecular weight heparins using a dosage as to achieve therapeutical blockade of the extrinsic blood coagulation pathway, measured by the activated Partial Thromboblastin Time or by testing the anti-factor-Xa activity, respectively, as known by persons skilled in the art. Alternatively, administration of citrate in order to complex calcium ions can be used for anticouagulation of the blood within the hemodialysis system. This procedure is provided by dialysis machines like Multifiltrate (Fresenius, Medical Care, Germany). The complexed calcium is dialysed by an initial hemodialysis step. During further processing the blood cannot coagulate. Before devolving the purified blood to the patient a predefined dosage of an infusion containing calcium ions is co-administered to the blood stream, reestablishing coagulation.

According to the inventive finding that the extraction fraction of the procedure can be increased by stimulation of lipolysis in a person thus treated it is preferred to apply drugs inducing lipolysis such as β1-, β2-, β3-adrenoreceptor agonists, phosphodiesterase-III inhibitors, α-1 and -2 adrenoreceptor agonists, nitroxide or nitroxide donors, hormone sensitive lipase, leptin, natriuretic peptide, vasopressin, heparin and analoga, thyrosine, yohimbine.

Furthermore, the inventive stimulation of lipolysis relates to regional enhancement of the lipolytic activity by means of local subcutaneous infiltration of the aforesaid lipolytic drugs, as well as anesthetics, liposomes including phospholipids, vasodilators including histamine. Further increase of lipolysis can be achieved by electrical field stimulation or applying ultrasound or pulse wave energy.

Solubilizing compounds such as arginine, like other small water soluble molecules, readily pass hydrophilic dialysis membranes. Although being not toxic, removal of unphysiological high concentration of arginine from blood/plasma by a final dialysis using a standard dialyser (high- or low-flux) is preferred. A final dialysis ensures reestablishment of a physiological electrolyte concentration, osmolarity and pH.

It can be useful to increase the concentration of blood albumin, phospholipids or cyclodextrines in order to increase the transport capacity of unesterified fatty acids during the procedure.

During such a combined treatment a close monitoring of hemodynamic parameters (blood pressure, heart frequency, temperature, hemoglobin oxygenation) as well as metabolic parameters (blood glucose, pH, sodium and potassium) is mandatory. The duration of one treatment episode depends on clinical parameters. Typically, a procedure takes between 3 and 12 hrs., more preferably the duration is between 4 and 6 hrs. The amount of extracted fatty acids depends on the selectivity of the filtration membrane used towards pathogenic fatty acids. The preferred amount of extracted fatty acids is between 100 and 2000 ml, more preferably between 500 and 1500 ml.

The purification procedure for clinical use can be performed as a method of dialysis, filtration, adsorption, precipitation or combinations thereof.

Large-Scale Extraction of Free Fatty Acids in Industry

Free carboxylic acids are frequently found in solutions or emulsions produced or used in large-scale plants. For example, fatty acids are present in raw vegetable oils, in the shell and hull of corn fruits and vegetables; in biomass or waste waters; in crude mineral oil or arise during processing as well as in oil containing soils; in waste oil and grease disposal. In most instances physical procedures are used to remove these carboxylic acids which require a high energy demand. In some instances the separation procedure has undesired consequences to the purified product. For example, for refinement oils are exposed to steam in order to distill volatile fatty acids. During such a procedure heat exposure can lead to transisomerisation of the esterified carboxylic acids. This is a potential hazard for the consumer. Therefore avoidance of such procedures is desirable.

It was found that this task can be solved by the inventive procedure.

According to the invention these aqueous or organic solutions to be purified arise from plants, organisms, fossil materials, natural or synthetic reaction mixtures.

One preferred embodiment is the purification of oils from free carboxylic acids by addition of aqueous solutions of at least one solubilizing compound as disclosed herein such as compounds of general formula (I) or arginine or arginine analogues and mixtures of such compounds (FIG. 4). Oil to be purified is poured from a storage tank (402) into a reaction tank (401). A predefined amount of a concentrated solution of the solubilizing compound from a storage tank (403) is added to the reaction tank. Preferably, the solution is mixed by means of a mixing system (411). Then the mixture is pumped (pump 412) to a collecting tank (405) where the aqueous and the oily phase spontaneously separate through gravity. The lower aqueous phase contains the carboxylic acids which dissipate in the micro- or nanoemulsion which is continuously removed through the outlet at the lower site of the tank. Alternatively, the mixture is transferred to a centrifuge or a membrane separator. This procedure can be repeated if a higher grade of purification is demanded. It has shown to be advantageous to slightly warm the solutions while mixing them in order to attain completeness of the solubilization process. The mixing process is accelerated by application of sonar waves. When the mixture is transferred through a membrane separator it turned out to be advantageous to use primarily anion-selective membranes. The purified oil (triglyceride phase) usually does not contain any solubilizing compound after removal of water. However, for highly purified oils it can be useful to repeat washing with water or to use cation adsorbers. The purified triglyceride phase from the upper phase of the collecting tank is continuously removed through an outlet located at the upper site of the tank and transferred to a triglyceride storage tank (404). The aqueous solution is pumped from the lower part of the collection tank (405) into a second reaction tank (406). A predefined amount of acid is added from an acid storage tank (407). The solution in the reaction tank is mixed by means of a mixing system (411). Thereafter the mixed solution is pumped (412) into a second separation tank (408). Fatty acids and solubilization compounds solubilized in water are allowed to separate by gravity. However, other means of separation as known in the art can be used instead. The purified fatty acids that concentrate in the upper part of the second separation tank are constantly transferred into a fatty acid storage tank (409). The aqueous solution of the solubilizing compound that concentrates in the lower part of the second separation tank is continuously pumped into an electrodialysis unit (410). Electrodialysis can by applied in order to remove cations and/or anions by techniques and devices as known in the art and by means of ion-selective membranes (413). The purified solution of the solubilizing compound is pumped into the solubilization compound storage tank (403). A preferred solubilization compound for this purpose is an arginine derivative and especially arginine.

Alternatively to separation by gravity, solubilised carboxylic acids within the aqueous phase may be separated by processes utilizing electrophoresis, pneumatic or nano-filtration, immobilization, aggregation, distillation or phase transfer by means of an organic solvent. In a preferred embodiment adsorption of the volatile carboxylic acids by carbon, complexation with calcium, phase transfer by use of organic solvents, electrodialysis and organo-nanofiltration is used. A preferred embodiment is the use of esterases when using the inventive solubilisation procedure in the processing of sewages or biodiesel production (see Chapter E, 2. Hydrolases). Their combined use enhances the effectivity and completeness of the removal of organic, respectively oily components or the chemical reactivity.

For realizing the inventive methods the carboxylic acids can be present in a solution and at least one solubilizing compound of general formula (I) or (II) is added.

Alternatively, the carboxylic acids are added to a macro-, micro- or nanoemulsion containing at least one solubilizing compound of general formula (I) or (II) in order to use said emulsion to liberate, decomplex, detach, react, aggregate, complex, coagulate, flocculate, sediment or separate the carboxylic acid-containing complexes.

These inventive methods can be used for initializing, enhancing, maintaining or diminishing a physico-chemical or chemical reaction, enabling, enhancing the up-take and transport of reaction products or components in a biological or chemical reaction processes, detaching, solubilizing, liberating, convecting, transporting substances by vesicle up-take, or enabling or enhancing the penetration of the emulsified carboxylic acids through hydrophilic or amphiphilic media or solids.

Preferred Industrial Applications Include
- the removal of fatty acids from fatty acid-containing solutions arising in crude oil or fuel processing. Particularly in the production and processing of mineral oils and fuels, respectively in biofuels the inventive method can be applied.
- the removal of fatty acids from fatty acid-containing solutions arising in industrial food processing. Particularly in the production of edible oils, processing of corn, rice and whey bran, vegetables as well as milk and fish products, low fat foods and fat-free products, and oil containing or producing organisms, respectively, this method shall be useful.
- the removal of fatty acids from fatty acid-containing aqueous solutions arising in the processing of sewage containing bioorganic compounds, or in industrial sewage. For example, for processing the sewage from bioreactors this method can be applied.
- the removal of fatty acids from fatty acid-containing organic or aqueous solutions arising from cleaning of industrial products like wool, cotton or other textiles; in the processing of sewage from industrial cleanings like tank plants, tankers, car washes, slaughterhouses, a.o.
- the removal of fatty acids in chemical or pharmaceutical processings, like preparation of adhesives or paints.
- the removal of non-carboxylic acid substances that aggregate or adhere to solubilized carboxylic acids thereby co-solubilizing and being separated or removed along with the inventive solubilizing substance and carboxylic acids as to be used in purification of crude fats and oils of mineralic or organic origin, in order to remove complexing phospholipids, glycolipids, sterols, pesticides being solubilized already or immobilized to organic or inorganic matter.
- the removal of adhesive, bound or complexed substances by macro-, micro, or nanoemulsions of the inventive solubilizing substances and carboxylic acids for extraction of organic oil seeds, oily sands or rocks, and oily deposits.

Application for the Analysis of Fatty Acids in Aqueous Solutions

Qualitative and quantitative analysis of carboxylic acids is a cumbersome task. Carboxylic acids with a carbon chain length exceeding 6-10 depending on the presence of hydrophilic or hydrophobic substituents can't be measured in aqueous media, prohibiting their measurement by electrophoresis or conductometry. Furthermore, analytics can be hampered by incomplete dissolution of carboxylic acids from organic compounds, even when organic solvents have been used. Standard analysis is performed with gas chromatography (GC). However, carboxylic acids have to be methylated to be suitable for GC, thus making this method time consuming and susceptible to methodological faults. These difficulties can be overcome by the inventive solvation procedure.

According to the invention this method can also be used for qualitative and quantitative analysis of the content of fatty acids in aqueous solutions. It is also suitable for the differentiation of the relative content of esterified and non-esterified fatty acids.

A preferred embodiment of the inventive solvation procedure is their use for analysis of carboxylic acids by electrophoresis, conductometry and spectrometry.

Preparation of Analytical Samples

Mixtures of oil and fatty acid as well as mixtures with water as oil-in-water (o/w) and water-in-oil (w/o) emulsions are transferred to a reaction chamber. A solution with an inventive solubilizing compound is added. For determining the esterified fatty acids esterases can be added before, together with or after addition of the solubilized compound in order to liberate them. The solutions should be incubated. It showed to be helpful to moderately heat the sample volume, reduce the ionic strength or reduce the pH before adding the solubilizing compound. The ensuing analyses can be done
- with the solution in its present state,
- by means of precipitation of free carboxylic acids,
- by means of extraction with an organic solvent.

The use of the resulting analytes with standard analytical methods is described in the following.

Gel Electrophoresis Procedure

For analysis of carboxylic acids by gel electrophoresis the aqueous analyte can be taken in its present form or as filtrate of electro-nanofiltration or dialysis being dissolved by the solubilizing compound as a micro- or nanoemulsion. A standard device for gel electrophoresis can be used (for example, BIOTEC-FISCHER GmbH, PHERO-vert 1010-E) and an SDS-polyacrylamide gel. It can be useful to add protic solvents like ethanol to the analyte. In a preferred embodiment an organogel is used (see 6. Organogels). Calibration and reading can be done as known in the art.

Distillation

A solution containing non-esterified fatty acids solubilized in an aqueous solution of the solubilizing compound can be purified by a one- or two-step distillation. This can be done by heating and steaming of the solution at ambient air pressure or under vacuum conditions in order to reduce the evaporization temperature of the fatty acids to be distillized. A preferred embodiment is the use of a thin film evaporator (Normag, Roatafil apparatus).

Precipitation/Complexation Procedure

Precipitation or complexation of solubilized carboxylic acids can be performed as described before and known in the art. Namely methods such as complexation with metal ions or cyclodextrins are preferred. The precipitate has to be extracted and washed with water as known in the art. The purified precipitate is then dissolved in a strong acid (HCl, acetic acid, carbonic acid) until complete dissolution and protonation of the carboxylic acids. Carboxylic acids are then extracted with an organic solvent (n-hexan, diethylether, chloroform, a.o.) The organic phase is carefully removed and processed for further analyses.

A preferred analytical method is liquid chromatography.

Solvent Extraction Procedure

Extraction of carboxylic acids from media not sensitive to acidification or exposure to organic solvents can be performed directly from an aqueous medium. The inventive use of the solubilizing compound has the decisive advantage that the extraction condition doesn't have to be as drastic as compared to sole solvent extraction procedures. This is accomplished by the carboxylic acids to be extracted being already dissolved in the aqueous phase by the inventive solvation procedure. Careful acidification in the presence of an organic solvent phase drives protonated carboxylic acids to pass to the solvent phase without the need of rigorous mixing of solvent and medium. Then solvent extraction is performed as known in the art. The solvent solution can be used for NIR-, or IR, or far IR-spectrometry or liquid chromatography directly.

Electro-Nano-Filtration/Diffusion Procedure

A further preferred analytical method is electrophoretically- or electrostatically-driven filtration or diffusion for separation to be used with the inventive solubilization (FIG. 5). Organic or inorganic material, solution/emulsion is prepared by the aforesaid solubilization. The pH value should be adjusted to values >6.0, preferably to values between 8 and 11. In the following a defined sample volume is transferred to the donor chamber/reaction batch of the analytical device. This donor chamber (503) is disposed between a chamber filled with catholytes (502) and a separation chamber (505). The donor chamber/reaction batch and the catholyte chamber are separated by a membrane (504). Preferably, this membrane is ion-selective. The separation chamber is filled with a chromatophore (e.g. a gel, preferably an organogel). Alternatively, it can consist of a microfluidic system or a functionalized nano-filtration or diffusion membrane as described below (see Chapter E, 3. Membranes, and 4. Materials for surface functionalization) (510). On the other side of the membrane separator an acceptor chamber/container (508) is disposed which is filled with an arginine solution or a solution of any other solubilizing compound. This acceptor chamber/container is adjacent to a further chamber/container (507) which serves for receiving the anolyte. These chambers/containers are separated by a membrane (506). Alternatively, the separation pannel is an organogel filled in a capillary. Preferably, the membrane is ion-selective. When applying voltage between the cathode (501) and anode (509) the ionized carboxylic acid compounds present in the donor chamber/container, particularly the fatty acids, as anions are conducted through the separation chamber/membrane and thus transferred to the acceptor chamber/container. The solution in the acceptor chamber/container can be analyzed immediately. Preferably, the analysis is carried out by conductometry, spectroscopy or mass detection methods. Alternatively, a further agent (e.g. an indicator, a derivating agent) is added and analysis ensues. Suitable anolytes and catholytes are arginine solution, solutions of arginine derivatives, HCl, a.o. Adding, mixing and transferring the agents is preferably carried out in a microfluidic system. This is particularly suitable for the development of a "lab-on-the-chip" analysis system.

Practical applications are medical—biochemical analyses of fatty acid contents of body fluids taken as a sample from a subject. Such an analysis can serve as a diagnostic criterium. Medical diagnoses include but are not restricted to atherosclerosis, hypertension, diabetes mellitus, obesity, hyperlipoproteinemia, myocardial infarction, stroke, renal failure. Scientific applications include the use in chemistry, biochemistry, pharmacy, pharmacology, materials science, biology, industrial food processing. This analytical method can also be used in industrial applications as lined out in the previous paragraph on large-scale extraction of free fatty acids.

Dialyses/Extraction Devices and Procedures

A subject of the invention is an integrated dialyser/extractor. For performing the inventive solubilization and separation of carboxylic acids in an aqueous or organic medium with a solubilizing compound of general formula (I) or (II) such an integrated dialyser/extractor should comprise the following essential key components which are essential to most embodiments, irrespective of their application:

i) A first chamber for reacting the carboxylic acid-containing aqueous or organic medium with the solubilizing compound of general formula (I) or (II);
ii) A second chamber for receiving the solubilized carboxylic acids;
iii) A separation panel between said first chamber and said second chamber comprising a separation membrane or a hollow capillaries assembly; and
iv) Means for conducting said reactive solution from said first chamber to said second chamber through said separation panel by applying a concentration gradient, a thermic gradient, a physico-chemical gradient, a pneumatic gradient, an electric gradient or a combination thereof.

This device can be used for medical therapy, medical analytics, food analytics, food processing, oil processing, oil analytics, fuel processing, chemical and pharmacological or pharmaceutical processings, analytics in pharmaceutical or chemical industy or science, removal of carboxylic acids from sewage from private, commercial or industrial cleanings, removal of carboxylic acids from bioreactor processes, cleanings of oily solid matters, organogelation or nanoemulsification of carboxylic acids.

For using such a device a method with the following key steps is applied:
i) Providing the solution or emulsion or suspension containing the carboxylic acids;
ii) Addition of at least equimolar amounts of at least one solubilizing compound;
iii) separating the solubilized carboxylic acids from the solution or emulsion or suspension by phase separation, filtration, nanofiltration, dialysis, absorption, complexation, destillation and/or extraction.

More specifically, step iii) is preferably achieved by means of one of the following separation methods or a combination thereof:

passing the carboxylic acids separately or together with the at least one solubilizing compound through a separation membrane or a tube or a hollow capillary assembly by applying a concentration gradient, a thermic gradient, a physico-chemical gradient, a pneumatic gradient, an electric gradient or a combination thereof; or performing phase separation by combining two or more media building phase separations; or passing the carboxylic acids together with the at least one solubilizing compound through a phase separation interface that allows the passage of said carboxylic acids and said at least one solubilizing compound by applying a concentration gradient, a thermic gradient, a physico-chemical gradient, a pneumatic gradient, an electric gradient or a combination thereof, wherein the phase separation interface consists of a gel, an organogel or a solid material or a combination thereof; or filtrating the carboxylic acids by using at least one solubilizing compound; or nanofiltrating the carboxylic acids by using at least one solubilizing compound; or dialyzing the carboxylic acids by using at least one solubilizing compound; or adsorbing the carboxylic acids by using at least one solubilizing compound; or complexing the carboxylic acids by using at least one solubilizing compound; or distilling the carboxylic acids by using at least one solubilizing compound; or separating the carboxylic acids by using at least one solubilizing compound by supercritical fluid extraction.

In the separation step the gel and/or the solid materials can be of organic or inorganic origin and they can be either porous or non-porous.

According to the invention, aforesaid device and method shall be used in the following fields: Medical therapy, medical analytics, food analytics, food processing, oil processing, oil analytics, fuel processing, modulation of chemical or physico-chemical reactions, solubilization of poorly solvable molecules, chemical and pharmacological or pharmaceutical processings, analytics in pharmaceutical or chemical industy or science, removal of carboxylic acids from sewage from private, commercial or industrial cleanings, removal of carboxylic acids from bioreactor processes or soils or plants, cleanings of oily solid matters, organogelation or nanoemulsification of carboxylic acids. Said analytic methods can be quantitative or qualitative.

In a more specific form preferred embodiments comprise the following parts:

a) A first chamber for reacting the carboxylic acid-containing aqueous medium with the solubilizing compound, having a first inlet for said carboxylic acid-containing aqueous medium;

b) A container for said solubilizing compound, having a second inlet for filling said container with said solubilizing compound and being connected to said first chamber via a third inlet;

c) A second chamber for receiving the dialysed/filtrated carboxylic acid containing solution;

d) A separation panel between said first chamber and said second chamber comprising a separation membrane or a hollow capillaries assembly; and e) Means for conducting said reactive solution from said first chamber to said second chamber through said separation panel by applying a concentration gradient, a thermic gradient, an electrical gradient, a physico-chemical gradient, or combinations thereof.

Optionally, it may also comprise the following components:

f) Means for removing the associates of carboxylic acid and solubilizing compound from said filtrated solution by means of removing said filtrated solution through convection of an acceptor solution being fed through a fourth inlet into said second chamber and allowed to flow off through a first outlet out of said second chamber; and g) Means for removing the purified solution from said second chamber through a second outlet.

Such an integrated dialyser/extractor is suitable for performing the inventive solubilization and separation of carboxylic acids in an aqueous or organic medium in a broad range of medicinic and industrial applications. These key components build the centerpiece of the devices designed for specific applications. Specific embodiments for particular applications are described in detail further below.

It should be noted that according to the invention all inlets, outlets and transport means may have adjustment devices for controlling the respective flow or transfer rates. These adjustment devices will not be expressly named for each embodiment. All adjustment devices known in the art will be suitable according to the invention.

Subject of the invention is also a method which applies the key steps for solubilizing and separating carboxylic acids in an aqueous or organic medium by using the aforementioned integrated dialyser/extractor. The core of the inventive methods is represented by the following steps:

a) Preparing said solution by reducing ionic strength by means of complexation, adsorbtion, separation or dialysis of bound and unbound cations;

b) Adjusting the pH of the solution by means of adding an acid or a base;

c1) Adjusting the molarity of the solubilizing compound to be in the range of 1:10 to 20:1 compared to the estimated concentration of the carboxylic acids to be solubilized; and d) Adding said solubilizing compound in a solid form or in a solution to said carboxylic acid-containing aqueous or organic solution for generating a micro- or nanoemulsion.

Optionally, the method may also comprise any of the following steps:

a1) liberation of carboxylic acids bound by complexation or covalent binding c2) If the solubilizing compound is administered in a solution, adjusting the pH of said solution in order to optimize compatibility and reaction conditions with the carboxylic acids to be solubilized by means of acidification or alkanisation;

e) Adding esterases, hydrolases or a complex builder;

f) Adding water and/or a cosolvent to the solution; and/or g) Optimizing reaction conditions by means of heating and/or mixing the solution, thereby generating an improved micro- or nano-emulsion.

In the aforegoing description of the inventive devices and methods as well as in the following modifications and embodiments not all features have to be included, respectively not all steps have to be performed, some of them are optional. Further, in some embodiments some features or steps are modified, respectively displaced by corresponding features or steps. Therefore the sequence of the respective method steps has to be read in an alphabetic order first. In second place the numeric affix is decisive. For example, if a step c and a step c1 is present, step c1 will be carried out after step c. In other words, step c1 will be intercalated between step c and step d. In an analogous manner, if a step c1 and a step c2 are present in a method this means that step c1 has to be carried out before step c2. In other words, step c1 is intercalated between steps b and c2. If in an embodiment a step is modified, respectively replaced in comparison to the aforegoing embodiment it may occur that for example in each embodiment a different step g is listed. The sequence of these alternative steps has to be read in the correct alphabetic order. So if a modified step g is present in the step listing this means of course that a step g from another embodiment is not included in the present embodiment. In case optional steps are included the steps may be presented in a non-alphabetic order. This does not change the line to understand the sequence of the steps in an alphabetic order. The same applies for modifications in the respective inventive devices.

In embodiments in which at least two chambers are provided the listing of the steps of the inventive method can be complemented in the following way:

g2) Conducting the reactive solution from a first chamber to a second chamber through a separation panel using nanofiltration technique by applying a concentration gradient, a chemical gradient, a pneumatic gradient, an electric gradient or a combination thereof.

Optionally, the following steps may be comprised in these embodiments:

h) Removing the associates of carboxylic acid and solubilizing compound from the filtrated solution through convection of an acceptor solution being led through an inlet into said second chamber and allowed to flow off through an outlet of said second chamber; and i) Removing the purified solution from said second chamber through a further outlet The steps g2), h) and i) can be performed after step f) as described above. A very important application of the inventive method is the purification of the blood of a patient from volatile fatty acids.

Therefore the respective embodiment of an inventive integrated dialyser/extractor has the following modifications, respectively additional features (FIG. 6):

f) Means for conducting blood or plasma from said subject to said first chamber (610) of a dialyser (603) through said first inlet;

g) A pumping system and mixing system (602) that allows feeding in the solubilizing compound from said container (601) and mixing the solution;

h) Optionally said first chamber contains support materials (604) at which hydrolases are immobilized in order to liberate esterified fatty acids;

i) A first separation panel between said first chamber of a second dialyser and second chamber of a first dialyser, comprising a separation membrane (605) or a hollow capillaries assembly;

j) Means for conducting the carboxylic acid-containing solution from said first chamber of the first dialyser to a second chamber of the first dialyser by applying a concentration gradient, a chemical gradient, a pneumatic gradient, an electric gradient or a combination thereof;

k) Means of pumping (606) said filtrated solution from said second chamber to a first chamber of a second dialyser (607);

l) Means for removing the associates of carboxylic acid and solubilizing compound passing through said second separation panel of the second dialyser (607) by means of a tertiary circulation;

m) An acceptor solution storage container;

n) Means for pumping (612) the carboxylic acid acceptor solution from said acceptor solution storage container (609) into said second chamber of the second dialyser;

o) Means for removing the loaden carboxylic acid acceptor solution into a waste container (608);

p) Means for reconducting the purified solution containing the solubilizing compound exiting said first chamber of the second dialyser to the inlet of said second chamber of the first dialyser; and q) Means for reconducting the reunited blood fractions exiting the first chamber of the first dialyser into the circulation of the subject (611).

In further preferred embodiments a standard blood dialysis preceeds and/or succeeds the steps of the inventive method. The advantage is to combine a conventional blood dialysis as often performed in patients with kidney failure with a special purification of the blood from volatile fatty acids in one procedure.

The respective method for applying such a dialyser/extractor for purifying an ex vivo blood sample from volatile fatty acids includes the additional steps, respectively modifications:

g1) Liberating esterified fatty acids in the blood of a subject by hydrolases immobilized on support materials inside said first chamber thus generating a micro- or nanoemulsion;

h) Pumping the filtrated solution from said second chamber to a first chamber of a second dialyser;

i) Conducting the carboxylic acid-containing solution from said first chamber of the second dialyser to a second chamber of the second dialyser through a second separation panel by applying a concentration gradient, a chemical gradient, a pneumatic gradient, an electric gradient or a combination thereof;

j) Removing the associates of carboxylic acid and solubilizing compound passing through said second separation panel by means of a tertiary circulation;

k) Pumping the carboxylic acid acceptor solution from an acceptor solution storage container into said second chamber of the second dialyser;

l) Removing the loaders carboxylic acid acceptor solution into a waste container; and m) Reconducting the purified solution containing the solubilizing compound exiting said first chamber of the second dialyser to the inlet of said second chamber of the first dialyser.

A phase separation interface consists of porous membranes, gels with or without voids or tubes with porous walls. The membrane configuration can be flat, or round, processed in batches, queues or modules. Tubes can be singular or have multiple channels. In a preferred embodiment hollow chamber capillaries are used. They have diameters between 100 and 300 µm, and a length between 200 and 400 mm. The number of hollow chamber capillaries ordered in parallel depends of the blood (plasma) flow rate that is intended. Typically, the number of capillaries within a dialyser is between 10.000 and 40.000. The contact duration of blood (plasma) with the capillary wall should be between 2 and 50 seconds.

Interface material can consist of anorganic or organic materials, or a combination of both. Materials are listed below (see Chapter E, 3. Membranes). A preferred embodiment is the use of a ceramic, polymeric, metallic or carbon support material. Most preferred is aluminium oxide and polycarbonate. The architecture of the material can be symmetrical or asymmetrical, as known in the art. The intersecting channels/spaces/voids can have a geometric or a random configuration. The channel diameters may vary considerably, however, they should be in a range that allows ultra-, micro- or nanofiltration. In a preferred embodiment is the use of a nanofiltration membrane as described before (see chapter nanofiltration methods).

In principle, the same membranes can be used for filtration, dialysis or osmosis. However, membranes for dialysis or osmosis need to be more selective, respectively sealed. The use of a gel nested in said support structures is used in another preferred embodiment. Such gels can consist of hydrophilic or organophilic components or both. Gels exhibiting self-assembly and displaying nanostructured voids or channel structures after formation, respectively solvent extraction are used in a preferred embodiment.

An extractor used for biological materials, foods, waste solution, or industrial use may have different dimensions of the aforesaid components, however the basic assembly is the same.

The concentration of carboxylic acids in solutions considered for analytics processing or purification may vary by a great extent. For optimal solubilization a ratio of (solubilizing compound:carboxylic acid) 1:1 to 4:1 depending on the pH and the ionic strength should be adjusted. A lower ratio will lead to an incomplete solubilization, a higher ratio might interfere with further processing. However, the content of carboxylic acids can be completely unknown. This problem can be overcome by monitoring turbidity of the aqueous solution, respectively emulsion. Emulsions are turbid and miniemulsions exhibit turbidity when irradiated with UV light. Micro- and nanoemulsions are optically transparent. However, by means of nephelometric turbidity using multibeam unit particles from 1 up to 1000 nm can be detected. Therefore solubilization progress can be monitored by measurement of turbidity. For an individual application it will be possible to calculate the amount of the solubilizing compound that has to be added if a defined transparency is reached to achieve the intended ratio between the solubilizing compound and the carboxylic acids to be solved. In case that particles not being micelles of a carboxylic acid are present in the solution to be solubilized it can be advantageous to filter those particles off or centrifuge them off.

On the other hand, a less sophisticated use of the solubilization process can be used also. Most of the solubilizing compounds such as arginine display a neglectible toxicity. Furthermore, since they are highly soluble unphysiologic concentrations thereof can be removed by a dialysing step as know in the art. Therefore a fix adjustment of the concentration achieved during the mixing process can be chosen. This concentration should be in the range from 100 to 1000 mmol/l, the adjustment of an infusion pump supplying the mixing segment with the solution of the solubilizing compound can be calculated from the blood (plasma) flow rate and the intended concentration.

A typical scheme of an integrated dialyser/extractor is shown in FIG. 7. The module consists of a cylindrical cartridge (701). A reaction chamber (702) located at the side of the inflow is separated from the separation chamber (703) be the sealing plane A (704). The reaction chamber can harbour various systems for mixing of fluids. The example shows ondulated lamellae (705). The reaction chamber has a separate inflow for the solubilising compound (712).

A capillary bundle (706) comprising hollow membrane capillaries is embedded at both extremities in a sealing compound so as to seal them off. Membrane capillaries are embedded in a sealing compound of the sealing plane A and B (704, 707), open with their ends towards the reaction chamber (702) and the collection chamber (708), respectively. The sealing planes are sealed so that the separation chamber (703) is separated. Both ends of the cylindrical housing are locked up by a cap carrying an in-/outlet with a connection plug (709). The housing has a further in-/outlet (710, 711) intersecting the housing wall in the proximity of both sealing planes which communicate with the separation chamber. In-/outlet tubes close up in a connection plug (not shown). Housing and sealing material can consist of a polymer like PU, PA, PE.

Another method for the purification of blood is hemofiltration. Therefore, the blood to be purified is pressurized by means of a roller pumping system and a valve/flow limiter downstream to the extractor. Depending on the desired filtrate fraction a transmembrane pressure of up to 500 mm Hg can be adjusted, which is calculated by the formula $$P_{inflow}+P_{outflow}/2 \text{ at the blood side}-P_{inflow}+P_{outflow}/2 \text{ at the filtrate side.}$$

However, for industrial applications higher pressures may be required.

Esterases can be immobilized for example on a composite membrane consisting of a polymeric binder such as polysulfone, poly(tetrafluoroethylene and poly(vinylidene fluoride) and metal oxides such as $TiO_2$, $SrO_2$, $HfO_2$ and $ThO_2$ (WO 1990/15137). Alternatively, esterases can be covalently bound to bi- or polyfunctional composites with a phosphate group between the composite and the above-mentioned metal oxides (WO 1999/32549).

Esterified carboxylic acids cannot be solubilized directly by the inventive procedure. In many instances it can be indicated to hydrolyze the carboxylic acids in order to make them suitable for solubilization. This can be accomplished by hydrolases, more specifically by esterases, respectively lipases. There is a wide variety of this class of enzymes found in living organisms and plants. For the use in blood or plasma esterases that hydrolyse alkyl residues from glycerin are of interest. It can be of interest to hydrolyse only carboxylic acids from mono-, di- or triglycerides using triacylglycerol hydrolases (EC 3.1.1.3) and to spare phospholipids. However, in some situation removal of all classes of esterified carboxylic acids could be indicated which can be accomplished by respective esterases (EC 3.1). In some indication hydrolysis of certain fatty acids is desirable e.g. trans-fatty acids, long-chain saturated fatty acids. In general, hydrolysis of long-chain fatty acids (>12 C atoms) is a preferred embodiment of the inventive procedure when used for purification of blood or plasma. Esterases should be immobilized to a support material so that they can not leave the reaction chamber. Materials suitable to carry the immobilized enzymes can be lamellae, meshes, membranes, tubes, spheres, ceolites, or gels. The immobilization technique of the enzymes depends on the support material used and is not a matter of the invention. In a preferred embodiment for the use in an extractor for medical use aluminium oxide or titan oxide is used as a support material, configured as blocks containing tubular spaces with a width between 100 and 500 μm, more preferably between 200 and 400 μm. Their surface is functionalized with an enzyme. Another preferred embodiment is the use of microspheres made of PMMA, PEEK, silicon, silicone or other materials. The preferred mean diameter is between 100 and 500 μm, most preferred 200 to 400 μm. Their surface is functionalized with an enzyme. In a further preferred embodiment carboxylic acids and/or triglycerides are released from phospholipid vesicles which carry those molecules within the blood. A preferred application form for an extractor is the use of enzyme containing materials as a separate unit which can be stored separately from the extractor. The advantage of this modular technique is that in case of necessity to store enzyme containing materials at a defined temperature the required space for storage is reduced. Furthermore, in case of loss of enzymatic activity during the treatment procedure this component could be renewed without the necessity to renew the other components.

Dialyses/Extraction Procedures—Variant II

In a further preferred embodiment the solubilizing compound is immobilized to the separation membrane or the hollow capillaries. Thus the dialyser can be simplified and comprises the following parts:
a) means for conducting blood from the subject to a first cavity chamber;
b) a first cavity chamber
c) optionally immobilizing lipases used for hydrolyzing fatty acids and liberating fatty acids adsorbed or bonded to proteins, lipids or cell membranes;
d) a separation panel between the first cavity chamber and a second cavity chamber comprising a separation membrane or a hollow capillary assembly characterized in that the solubilizing compound is immbolized at the separation membrane or inside the hollow capillaries;
e) means for conducting the reactive solution from the first cavity chamber to a second cavity chamber by applying a pneumatic gradient, an electric gradient or a combination thereof;
f) a second cavity chamber for receiving the filtrate/dialysate;
g) a tank for reuniting the purified filtrate/dialysate from the second cavity chamber with the residual blood fraction from the first cavity chamber; and
h) means for reconducting the reunited blood fractions into the circulation of the subject.

Applications for Industrial Use: Two-Chamber Separators

According to the invention also a device is provided for removing fatty acids from aqueous solutions arising in crude oil processing, industrial food processing, in the processing of sewage containing bioorganic compounds or in any another industrial production or environmental technique. For these applications preferably a two-chamber system is provided which comprises (FIG. 8)

a) a first container (801) for receiving the fatty acid-containing aqueous solution containing carboxylic acids being continuously poured into the container from a feed stream (803);
b) means for adding a solubilising compound solution to the first container (804) and mixing said solution with the fatty acid-containing aqueous solution by means of an appropriate mixing system (805);
c) a separation membrane between the first container and a second container comprising a separation membrane (807) or a hollow tube or capillaries assembly;
d) means for conducting the reactive solution from the first container to a second container by applying a pneumatic gradient, an electric gradient by means of an electrical field between the cathode (806) and the anode (808) or a concentration gradient, a chemical gradient, or combinations thereof;
e) a second container (802);
f) means for removing the fatty acid-solubilizing compound associates from the filtrate solution by means of removing the filtrate through convection of an appropriate acceptor solution being fed through an inlet (809) and allowed to flow off through an outlet (810); and
g) means of removing the purified solution of the first container through an outlet (811).

In another embodiment of this device for removing fatty acids from aqueous solutions arising in the above-mentioned industrial processes the solubilising compound is immobilized to the separation membrane or the hollow tube or capillaries assembly. Thus the device can be simplified and comprises the following parts (FIG. 9):

a) a first container (905) for receiving the fatty acid-containing aqueous solution (901) and an aqueous solubilising compound solution (902) after mixing both liquids by means of an appropriate mixing system (903, 904)
b) a separation membrane between the first container and a second container comprising a separation membrane or a hollow capillaries assembly (906) optionally having the solubilising compound immobilized at the separation membrane or inside the hollow tubes or the inner side of a spiral wound module;
c) means for conducting the reactive solution from the first container to a second container by applying a concentration gradient, a chemical gradient, a pneumatic gradient, an electric gradient or a combinations thereof; and
d) a second container (908) receiving the reactive solution that is allowed to exit the chamber through an outlet (909);
e) a collection chamber (907) which is sealed towards the first and the second container by a sealing plane (912, 913), being traversed by the hollow tubes or the outer side of spiral wound modules; and
f) an inflow (911) and an outflow (910) of the collection chamber allowing perfusion of solutes through the collection chamber.

Another embodiment of the intentive solubilisation effect is the solubilization and separation of carboxylic acids from oils during pharmaceutical, chemical or industrial processing by means of fluid-fluid separation. The carboxylic acids can be present as an oil, an emulsion (O/W, W/O) or as a fluid/fluid system. Thus, this embodiment can comprise additionally the following parts:

h) Means for mixing the carboxylic acid-containing solution and the solubilizing compound by means of heating, sonification, laminar or turbulent flow conditions in said first chamber;
i) Means for transferring the mixed emulsion to said second chamber and separating the mixed emulsion by means of gravity or centrifugation;
j) A third chamber for receiving the purified oil from the second outlet of the second chamber;
k) A fourth chamber for receiving the associates of carboxylic acid and solubilizing compound from the first outlet of the second chamber;
l) A reservoir for a water-soluble acid;
m) Means for suspending said water-soluble acid from said reservoir into said fourth chamber,
n) Means for mixing the solution in said fourth chamber;
o) A fifth chamber suitable for phase separation by gravity for receiving the mixed solution from said fourth chamber;
p) Means for conducting the mixed solution from said fourth chamber to said fifth chamber;
q) A sixth chamber for receiving the purified carboxylic acids from said fifth chamber;
r) Means for conducting the purified carboxylic acids from said fifth chamber to said sixth chamber;
s) A seventh chamber for receiving the solution containing the solubilizing compound and the water-soluble acid gathering on the bottom of said fifth chamber;
t) Means for conducting the solution containing the solubilizing compound and the water-soluble acid to a seventh chamber;
u) Means for conducting the solution from the seventh chamber through an electrodialysis device or an ion exchanger for separating the solubilizing compound to a catholyte chamber and the added water-soluble acid to an anolyte chamber;
v) Means for conducting the solution from the catholyte chamber to said container for the solubilizing compound;
w) Means for conducting the solution from the anolyte chamber to the reservoir for the water-soluble acid;
x) Means for conducting the purified retinate solution after electrodialysis to a hydrophilic filter membrane; and
y) Means for re-using the aqueous filtrate; and
optionally comprising
z) Means for suspending and mixing an organic solvent to the solution of the seventh chamber.

The corresponding method for applying such a modified integrated dialyser/extractor comprises the following additional, respectively modificatory steps:

f) Mixing the carboxylic acid-containing solution and the solubilizing compound by means of sonification, laminar or turbulent flow conditions in said first chamber;
g) Transferring the mixed emulsion to a second chamber;
h) Separating said mixed emulsion in said second chamber by means of gravity and centrifugation;
i) Conducting the purified oil through the second outlet of the second chamber into a third chamber;
j) Suspending a water-soluble acid from a reservoir into a fourth chamber;
k) Mixing the solution in the fourth chamber;
l) Conducting the mixed solution from said fourth chamber to a fifth chamber;
m) Performing phase separation by gravity in said fifth chamber with the solution received from the fourth chamber;

n) Conducting the purified carboxylic acids from said fifth chamber to a sixth chamber;
o) Conducting the solution containing the solubilizing compound and the water-soluble acid gathering on the bottom of said fifth chamber to a seventh chamber;
p) Suspending and mixing an organic solvent to the solution in the seventh chamber;
q) Conducting the solution from the seventh chamber through an electrodialysis device for separating the solubilizing compound to a catholyte chamber and the added water-soluble acid to an anolyte chamber;
r) Performing electrodialysis on the solution from the seventh chamber;
s) Conducting the solution from the catholyte chamber to said container for the solubilized compound;
t) Conducting the solution from the anolyte chamber to the reservoir for the water-soluble acid;
u) Conducting the purified retinate solution after electrodialysis to a hydrophilic filter membrane; and
v) Storing the aqueous filtrate for re-use.

It is further preferred that the device for removing fatty acids from aqueous solutions according to the two previous embodiments additionally comprises means for immobilizing esterases used for liberalizing fatty acids adsorbed or bonded to other compounds present in aqueous or non-aqueous solution.

Another embodiment of the intentive solubilisation effect is the solubilisation and separation of carboxylic acids from organic solutions consisting of proteins, amino acids and other water-soluble molecules during pharmaceutical, chemical, biological or industrial processing by means of fluid-fluid separation. Such a device can be simplified and comprises the following parts (FIG. 10):

a) a first container (1001) for receiving the organic matter/carboxylic acid-containing solution (1009);
b) by means of suspending the solubilising compound solution from a storage container (1010) to said solution and mixing the solution of the first container with the solubilising compound solution using a mixing system (1011);
c) means for conducting the mixed solution to a second container (1002)
d) means for mixing the solution coming from the first container with a solution of $CaCl_2$ or another complexing material coming from a storage container (1003) while suspending to the second container by means of a pump (1005) that ensures complete mixing of the two solutions, thereby precipitating the carboxylic acids solubilized by the solubilising compound;
e) means for filtering the upstreaming purified organic solution in order to retain precipitated particles (1006);
d) means for continuous mechanical removal of the precipitate (1007);
e) means for transferring the precipitate to a third container and washing the transferred precipitate (1004);
f) means for acidifying the precipitate in the third container;
g) means for phase separation in the third container by organic solvents;
h) means for removing the upper phase of the third container containing the separated carboxylic acids;
i) means for transferring the purified organic solution from the second container (1002) to another container (1008); and
j) means for separating the solubilising compound by electrodialysis, dialysis, use of a cation-exchange resins or chelation of cations;

Optionally, the following steps can be intercalated, independently one from another:
d1) means for adding one or more complexation enhancers, adjusting the pH, and/or for adding organic solvents selected from methanol, chloroform and diethyl ether;
i1) means for performing one or more purification steps in order to remove organic and/or inorganic matter still present in the purified aqueous organic medium.

E. MATERIALS FOR THE USE OF THE INVENTIVE PROCEDURE

1. Phase Separation Interfaces and Materials Thereof.

In general, all kinds of separation materials can be used for the separation of solubilised carboxylic acids according to the inventive procedure. Since there is a broad field of applications the phase separation interface has to be adapted to the respective condition. In case of a process where the size of the solubilized carboxylic acids is smaller than the material, respectively the compounds that should be purified, classical filtration by size exclusion can be performed. The smaller the difference in size between the molecules in the solution to be purified and the carboxylic acids the more micro- and nanofluidic separation techniques have to be employed. For their use surface properties of the interface determine the efficacy of the separation. Since the carboxylic acids to be separated may vary according to the various applications the surface properties needed for a high effectivity may differ. In general, micro- or nanofluidic conditions exhibit the best conditions for being separated with a phase separation interface. Therefore interface materials can be composite materials consisting of a support material, a linker/filling material, and functionalization material, being composed in various combinations. Support materials can be of organic or inorganic origin. Examples are listed in the section "Separation Membrane Materials". Linker or filling materials can be organic or inorganic and selected from the list in the section "Separation Membrane Materials". Preferred compounds to be functionalized to the surface of the interface are listed in the section "Materials for Surface Functionalization".

Surfaces, being in close contact with the bulk solution to be purified, may have different demands to surface properties than the phase separation interface. This may hold true for applications being used for blood purification. In order to ensure hemocompatibility the surface being in contact with blood or plasma should be covered with materials of known compatibility.

Furthermore, it can be advisable to immobilize the solubilizing compounds onto materials of a reaction area or phase separation interface in order to avoid the mixing of the solubilizing compounds with the solution to be purified or to reduce the amount of the solubilizing compound needed. The same holds true for the use of hydrolases when their use is necessary in combination with the inventive procedure.

2. Hydrolases

Hydrolases are a major group of enzymes (EC 3). They are able to cleave esters, ethers, peptides, glycosides, acid anhydrides and C—C bonds in a hydrolytic manner. A major subgroup of hydrolases are esterases (EC 3.1). Esterases are enzymes that break down an ester bond into an alcohol and an organic acid (saponification). Among esterases lipases (EC 3.1.1) build an important subgroup. Lipases are enzymes which catalyze the hydrolysis of ester bonds of water-insoluble lipid substrates, most of all triglycerides, into digylcerides, monoglycerides, fatty acids and glycerol. Therefore lipases are a subclass of the esterases. They play important physiological roles in the digestion of dietary lipids, making energy stored in these compounds available.

Industrial applications of lipases involve lipases from fungi and bacteria which play important roles in human practices as ancient as yoghurt and cheese fermentation. In more modern applications, lipases are used in baking, laundry detergents and even as biocatalysts in the converting of vegetable oil into fuel.

Immobilisation of lipases offers the advantage of facilitating the enzyme recovery for reutilisation. Compared to immobilization by methods as adsorption or inclusion, the covalent immobilization of lipophilic enzymes has the advantage that the lipolytic activity cannot be removed by surfactants. It has been demonstrated that lipases can be covalently immobilized on carbon nanotubes, so they can be used as solid phase catalysts. Another application of lipase immobilization has been shown on cellulose-based organogels. Other examples of covalent immobilization of lipase include those on micron-size magnetic beads, on sepabeads and on polyphenylsulfone.

According to the invention hydrolases can be used for liberating fatty acids from mono-, di-, or triglycerides in blood, body tissues, food or fuel processing and oils. In a preferred embodiment esterases are used. More preferred are lipases. Most preferred are triacylglycerol lipase (E.C. 3.1.1.3), phospholipase $A_2$ (E.C. 3.1.1.4), cholinesterase (E.C. 3.1.1.8) and lipoprotein lipase (E.C. 3.1.1.34).

3. Membranes a) Properties of Membranes to be Used in Dialysis

In principle, for membranes classified as micromembranes ultra-nanofilters can be used. The architecture can be symmetrically or asymmetrically, porous or compact. They may consist of materials listed in the section "Support Materials or of Polymers" in the section "Separation Membrane Materials". The membranes can be flat or have a hollow tube or fiber configuration. The surface of the traversing pores or channels and/or the interface with the feed stream the can be functionalized with substances listed in the section "Materials for Surface Functionalization".

In a preferred embodiment the transmembrane openings consist of cylindrical or flattened channels or tubes with small variation in channel or tube diameter (<20%) highly ordered intersecting the membrane at right angles to the surface. A preferred embodiment is the use of membranes consisting of perpendicular nanotubes or filter membranes having a tethered lipid (double-) layers or plasma membrane-like structures sealing the surface of the membrane.

The mass transport of carboxylic acids can be accomplished by a concentration gradient, a chemical gradient, a pneumatic gradient, an electric gradient or combinations thereof. Diffusion methods utilizing a concentration gradient are used most commonly. The diffusion capacity can be increased by using acceptor media exhibiting a higher partition coefficient for the substance to be purified than in the donor solution. In principle, materials with a high affinity to accept organic anions are used in a preferred embodiment. A preferred class are molecules exhibiting amino groups (primary, secondary, tertiary, quaternary), a phosphate group or calcium. The molecules, respectively their structures should exhibit a minimum size that is larger than the lower range of openings (channels) of the dialysis membrane or medium. If the molecular size is smaller these molecules can be irreversibly immobilized on a matrix instead. In a preferred embodiment cross-linked polysterol bearing amid functionality, i.e. poly(acrylamido-N-propyl trimethylammonium chloride, poly[(3-(methacryloylamino)-propyl]trimethylammonium chloride), is used. Another preferred embodiment is the use of macromolecules like cyclodextrines and proteins, i.e. albumin or fatty acid binding proteins. These proteins could be freely solubilized or immobilized onto a matrix. The selection of matrix materials depends on the field of application. Materials can consist of solids, fibers, meshes, granules and ceolites. The use of micro beads and ceolites is preferred. The materials can consist of silicon, metals, ceramics or polymers. In preferred embodiments aluminium, titanium, silicone, polyacrylates, polylactates, polycarbonate, cellulose and its esters, cellulose acetate, polysulfone (PS), polyethersulfon (PES), polyamide (PA), polyvinylidene fluoride (PVDF), polyacrylnitrile (PAN), polyetherimide (PEI) and/or polyetherketone (PEEK) are used.

3.1 Membranes with an Immobilized Solubilizing Compound

According to the invention also a separation membrane is provided where a solubilizing compound is immobilized at the membrane surface on the afflux side.

Afflux side herein means the side of the membrane from which the solution is conducted across the membrane. In the inventive dialyzers this side refers to the first cavity chamber. In the inventive two-chamber separators this side refers to the first container.

The solubilizing compound can be either immobilized directly to the membrane-forming polymer, or it can be attached by means of a linker molecule. Such a linker molecule can be an oligopeptides of 1 to 10 amino acids, or polypeptides of up to several hundred amino acids. These peptides are covalently bound to arginine and/or other solubilising compounds. In case the solubilizing compound is arginine or a derivative thereof the immobilized arginine must offer free access to its guanidine group for ensuring that the inventive interaction with a fatty acid can take place.

In a particularly preferred embodiment arginine is immobilized inside the membrane pores. Thus it is ensured that the free fatty acids must pass close to an arginine when being conducted across the membrane. This immobilization enhances the efficacy of the purification process. Therefore less arginine has to be used. Alternatively, the physical parameters of the dialysis process can be adjusted accordingly. This may be particularly advantageous in blood dialysis in order to conserve sensitive blood components.

According to the invention also membranes are provided in which the solubilizing compound is immobilized at the membrane surface on the afflux side as well as on the inside of the membrane pores.

According to the invention also a hollow capillary is provided where the solubilizing compound is immobilized inside the capillary. Depending on the polymer from which the capillary is formed the solubilizing compound can be immobilized in a similar manner as in the inside of a membrane pore, as described above. The advantages of this embodiment have already been discussed in the previous paragraph.

Thus the present invention also refers to a hollow capillary characterized in that the solubilizing compound is immbolized inside the capillary.

3.2 Membranes with Immobilized Hydrolases

In a particularly preferred embodiment additionally lipases are immobilized on the afflux side of the separation membrane. Herein the arginine and/or other solubilising compounds can be immobilized either on the afflux side of the membrane too, or inside the membrane pores, or in a combination of both. The advantage of this embodiment is that no further means are required to which the lipases are immobilized. Furthermore, the close proximity between the lipase-based liberation of fatty acids to the immobilized arginine (or solubilising compound) increases the probability that a free fatty acid interacts with an arginine and/or other solubilising compounds. With increasing distance the probability is enhanced that the liberated fatty acid readsorbs to a hydrophobic structure before interacting with an arginine or a solubilising compound.

3.3 Separation Membrane Materials

The following polymers showed to be suitable for the use in separation membranes: polyolefins, polyethylene (HDPE, LDPE, LLPE), fluorinated ethylene, copolymers of ethylene with butene-1, pentene-1, hexene-1, copolymers of ethylene and propylene, EPR-caoutchouc or EPT-caoutchouc (third component with diene structure a.o.), dicyclopentadiene, ethylidene norbornene, methylene-domethylene-hexahydronaphthaline, cis-cis-cyclooctadiene-1,5-hexadiene-1,4, hexyl-(1-hexene-methyl hexadiene), ethylene-vinylacetate copolymer, ethylene-methacrylic acid copolymer, ethylene-N-vinylcarbazole, methacrylamide-N,N'-methylene-bis (meth)acrylamide-allylglycidyl ether, glycidyl(meth)acrylate, polymethacrylate, polyhydroxymethacrylate, styrene-glycidyl methacrylate copolymers, polymethyl pentene, poly (methyl methacrylate-methacryloylamido glutaminic acid), poly(glycidyl methacrylate-co-ethylene dimethacrylate), styrene-polyvinylpyrrolidone-glycidyl methacrylate copolymer, styrene-polyvinylpyrrolidone blends with crospovidone, ethylene-trifluoroethylene, polypropylene, poly-butene-1, poly-4-(methylpentene-1), polymethylpentane, polyisobutylene copolymer, isobutylene-styrene copolymer, butyl caoutchouc, polystyrene and modified styrene, chloromethylated styrene, sulfonated styrene, poly-(4-aminostyrene), styrene-acrylnitrile copolymer, styrene-acrylnitrile-butadiene copolymer, acrylnitrile-styrene-acrylester copolymer, styrene-butadiene copolymer, styrene-divinylbenzol copolymer, styrene-maleic acid anhydride copolymer, polydienes in cis-trans, in 1-2 and in 3-4 configuration, butadiene, isoprene, purified natural caoutchouc, styrene-butadiene copolymer (SBR), triblock polymers (SBS), NBR acrylnitrile-butadiene copolymer, poly-(2,3-dimethylbutadiene), a triblock copolymer of polybutadiene terminated with cycloaliphatic secondary amines, or -benzal-L-glutamate or polypeptides, or N-carbobenzoxy-L-lysine, poly-(alkenamere)-polypentenamere, poly-(1-hexenmethyl-hexadiene), poly-phenylenes, poly-(p-xylylene), polyvinyl acetate, vinyl acetate-vinyl stearate copolymer, vinyl acetate-vinyl pivalate copolymer, vinyl acetate-vinyl chloride copolymer, polyvinylic alcohol, polyvinyl formal, polyvinyl butyral, polyvinyl ether, poly-(N-vinyl carbazole), poly-N-vinyl pyrrolidone, poly-(4-vinyl pyridine), poly-(2-vinyl pyridinium oxide), poly-(2-methyl-5-vinyl pyridine), butadiene-(2-methyl-5-vinyl pyridine)-copolymer, polytetrafluoroethylene, tetrafluoroethylene-hexafluoropropylene copolymer, tetrafluoroethylene-perfluoropropylvinyl ether copolymer, tetrafluoroethylene-ethylene copolymer, tetrafluoroethylene-trifluoronitrosomethane copolymer, tetrafluoroethylene-perfluoromethylvinyl ether copolymer, tetrafluoroethylene-(perfluoro-4-cyanobutylvinyl ether) copolymer, poly-(trifluorochloromethylene), trifluorochloroethylene-ethylene copolymer, polyvinylidene fluoride, hexafluoroisobutylene-vinylidene fluoride copolymer, polyvinyl fluoride, polyvinyl chloride, impact-resistant PVC by admixing ABS, MBS, NBR, chlorinated PE, FVAC or polyacrylates, soft PVC, postchlorinated PVC, polyvinyl chloride-vinyl acetate copolymer, vinylchloride propylene copolymer, polyvinylidene chloride-vinyl chloride-vinyl chloride-vinylidene chloride copolymer, vinylidene chloride-acrylnitrile copolymer, polyacrylic acid, acrylic acid-itaconic acid copolymer, acrylic acid-methacrylic acid copolymer, acrylic acid ester-acrylnitrile copolymer, acrylic acid ester-2-chloroethylenevinyl ether copolymer, poly-(1,1-dihydroperfluoro-butylacrylate), poly-(3-perfluoromethoxy-1,1-dihydroperfluoropropyl acrylate), polysulfone, polyacroleins, polyacrylamide, acrylic acid-acrylamide copolymer, acrylamide-maleic acid copolymer, acrylamide-hydroxymethylmethacrylate copolymer, acrylamide-methylmethacrylate copolymer, acrylamide-methylacrylate copolymer, acrylamide-maleic acid anhydride copolymer, acrylamide-methacrylic acid anhydride copolymer, acrylamide-anilino-acrylamide copolymer, acryl amide-(N-acrylol-4-carboxymethyl-2,2-dimethylthiazoline) copolymer, polymethacrylamide, methacrylic acid-methacrylnitrile copolymer, methacrylic acid-3-fluorostyrene copolymer, methacrylic acid-4-fluorostyrene copolymer, methacrylic acid-3-fluoroanilide copolymer, nitrated copolymers of methacrylic acid with methacrylic acid-3-fluoroanilide or fluorostyrene or copolymers of methacrylic acid with 3,4-isothiocyanatostyrene, or N-vinyl pyrrolidone with maleic acid anhydride, or polyvinylic alcohol and polyallylic alcohol, polyacrylnitrile, acrylnitrile-2-vinyl pyridine copolymer, acrylnitrile-methallylsulfonate copolymer, acrylnitrile-N-vinyl pyrrolidone copolymer, PAN containing hydroxy groups, acrylnitrile-vinyl acetate copolymer, acrylnitrile-acrylic ester copolymer, polyallyl compounds, polydiallyl phthalates, polytriallyl cyanurate, poly-α-cyanoacrylate, polydimethylaminoethyl methacrylate and copolymers of acrylnitrile, methylmethacrylate-laurylmethacrylate copolymer, P-acetaminophenylethoxymethacrylate-methylmethacrylate copolymer, glycoldimethylmethacrylate-methacrylate copolymer, poly-2-hydroxyethylmethacrylate, 2-hydroxymethylmethacrylate-methylmethacrylate copolymer, glycoldimethacrylate-methacrylate copolymer, poly-2-hydroxymethylmethacrylate, 2-hydroxymethylmethacrylate-methyl methacrylate copolymer, glycolmethacrylate-glycoldimethylmethacrylate copolymer, HEMA-styrene block and graft copolymers, poly-N,N—P,P-oxydiphenylenemellitimide, polydiethyleneglycol bisallylcarbonate, aliphatic polyethers, polyoxymethylenes, polyoxyethylenes, polyfluoral, polychloral, polyethylene oxides, polytetrahydrofuran, polypropylene oxide, ethylene oxide propylene oxide copolymer, propylene oxide-allylglycidyl ether copolymer, polyepichlorohydrine, ethylene oxide-epichlorohydrine copolymer, poly-1,2-dichloromethyl-ethylene oxide, poly-2,2-bis-chloromethyl oxacyclobutane, epoxy resins, bis-phenol-A-diglycidyl ether, epoxidated phenol-formaldehyde, cresol-formaldehyde, resins, cross-linkage with carboxylic acid anhydrides, amines such as diethyleneamine, isophorondiamines, 4,4-diaminodiphenyl-methane, aromatic polyethers, polyphenylene oxides, polyphenol, phenoxy resins, aliphatic polyesters, polylactide, polyglycolide, poly-β-propionic acid, poly-β-D-hydroxybutyrate, polypivolactone, poly-ε-caprolactone, polyethylene glycol adipate, polyethylene glycol sebacate, unsaturated polyesters of maleic acid anhydride, phthalic acid anhydride, isophthalic acid, terephthalic acid or HET acid with ethylene glycol, 1,2-propylene glycol, neopentyl glycol, oxethylated bisphenols or cyclododecan diole, unsaturated polyester resins or vinyl ester resins by copolymerization of unsaturated polyesters with styrene, methacrylate, vinyl monomers, vinyl acetate, methylmethacrylate, polycarbonate, polycarbonate of bisphenol A and its derivatives and polyethers, polyester, segmented polycarbonates of bisphenol A and its derivatives and aliphatic polyethers, as well as aliphatic polyesters (see above), polyethylene glycol terephthalate (PET) surface-modified, grafted with acrylic acid or by partial hydrolysis of the surface of PET, polyethylene glycol terephthalate, polyethylene glycol terephthalate-adipate, polyethylene glycol terephthalate, segmented with polyether blocks and aliphatic polyester blocks and polytetrahydrofuran blocks, poly-p-hydroxybenzoate, hydroxybenzoic acid-hydroquinone copolymer, hydroxybenzoic acid-terephthalic acid copolymer, hydroxybenzoic acid-p,p-diphenylether copolymer, polyvinyl pyrrolidone, polyvinyl pyrrolidone-maleic acid anhydide copolymer, alkyd resins of glycerol, trimethylpropane, pentaerythrite, sorbitol with phthalic acid, succinic acid, maleic acid, fumaric acid, adipinic acid and fatty acids of linseed oil, castor oil, soybean oil, coconut oil, aliphatic polysulfides-(R-Sx-)=sulphur content, aromatic polysulfides, polythio-1,4-phenylene, aromatic polysulfid ether of phenol and thiophene, polyether sulfones, polysulfo-1,4-phenylene, poly-p-phenylene sulfone, polyimines, polyethyleneimine, branched polyethyleneimine, polyalkyleneamine, polyamide, polyhexamethylene adipamide, polyhexamethylene sebacic amide, polyhexamethylene dodecane diamide, polytridecan brassylic amide, versamides from vegetable oils with diamines and triamines, polyamide of w-aminocarboxylic acids with $\alpha,\beta,\gamma,\delta$-aminocarboxylic acids or lactams, terephthalic acid-m-aminobenzamide copolymer, polyamide hydrazide, e.g. of isophthalic acid and m-aminobenzohydrazide, polypiperazine amide, e.g. of fumaric acid and dimethylpiperazine, polybenzimidazoles of terephthalic acid and tetramino benzene (substituted), or of diamino phenyl ethers and dichlorophenyl sulfone (substituted and cyclizated), or of m-phenylene isophthalamide and terephthalamide, polyimides, e.g. of pyromellitic dianhydride, methoxy-m-phenylene diamine, pyrrones, e.g. of pyromellitic dianhydride and diamino benzidine, aromatic polyamides, poly-m-phenylene isophthalamide, poly-p-benzamide, poly-p-phenylene terephthalamide, m-amino benzoic acid-p-phenylene diamine-isophthalic acid copolymer, poly-4,4'-diphenyl sulfone terephthalamide from terephthalic acid and hexamethylenetetramine, terephthalic acid and trimethyl hexamethylenediamine and 2,4,4-trimethyl hexamethylenediamine, from terephthalic acid, diaminomethylene norbonene and $\epsilon$-caprolactam, from isophthalic acid and laurinlactam, from isophthalic acid and di-4-(cyclohexyl amino-3-methyl)-methane, from 1,12-decane diacide and 4,4'-diamine dicyclohexyl methane, aromatic polyamides with heterocycles, e.g. dicarboxylic acid dichloride, terephthalic acid and isophthalic acid, diaminic heterocycles with oxidazole, triazole, bithiazole and benzimidazole structures, 3-(p-aminophenyl)-7-amino-2,4-(1H,3H)-chinazolindion and isophthalic acid, polyamino acids, poly-methyl-L-glutamate, poly-L-glutamic acid etc., copolypeptides, e.g. from glutamic acid and leucine, glutamic acid and phenylalanine, glutamic acid and valine, glutamic acid and alanine, lysine and leucine, p-nitro-D,L-phenylalanine and leucine etc., polyureas from diisocyanates with diamines and ureas, polyurethanes from aliphatic and aromatic diisocyanates and bifunctional and trifunctional hydroxy containing polyesters (s. above) and aliphatic polyethers (s. above) and optionally modification with bifunctional amino group containing, hydroxyl group containing and carboxy group containing materials, e.g. hexamethylene diisocyanate, diphenyl methane diisocyanate, toluoylene diisocyanate 2,4 and 2,6, tolidine diisocyanate, xylylene diisocyanate, glycerin, ethylene glycol, pentaerythrite, 3-dimethylamino-1,2-propanediol and carbohydrates, aliphatic and aromatic dicarboxylic acids and their derivatives, o,m,p-phenylenediamine, benzidine, methylene-bis-o-chloroaniline, p,p'-diamino diphenylmethane, 1,2-diaminopropane, ethylene diamine, amino resins from urea and cyclic urea, melamine, thiourea, guanidine, urethane, cyanamide, acid amides and formaldehyde as well as longer aldehydes and ketones, silicones, polydialkylsiloxane, diaryl siloxane and alkyl-aryl siloxanes as dimethyl-, diethyl-, dipropyl-, diphenyl-, phenylmethyl siloxane, silicones containing functional groups, e.g. allyl groups, γ-substituted fluorosilicones containing amino groups and vinyl groups, e.g. aminopropyl triethoxysiloxane, 2-carboxyl propyl methyl siloxane, block polymer with dimethylsiloxane units and polystyrene or polycarbonate blocks, triblock copolymers of styrene, butyl acrylate with $\alpha,\omega$-dihydroxypolymethylsiloxane, 3,3,3-trifluoro propyl methylsiloxane, avocan (90% silicone and polycarbonate), block copolymers of silicone and polycarbonate, hydrophobic polymers with an additive of hydrophilic polymers, e.g. polysulfone polyvinyl pyrrolidone, cellulose and cellulose derivatives, e.g. acetylcellulose, perfluorobutyryl ethylcellulose, perfluoroacetylcellulose, polyaromatic polyamide polymers, cellulose nitrate, carboxy-methyl cellulose, regenerated cellulose, regenerated cellulose from viscose and similar cellulose derivatives, agarose, polysaccharides as carrageenan, dextran, mannane, fructosane, chitin, chitosan (ethylene glycol diglycidyl ether, chitoson-EDGE), pectine, glycosamino glycanes, starch, glycogen, alginic acids, and all deoxypolysaccharides and halogeno-deoxypolysaccharides and their derivatives, amino-deoxypolysaccharides or sulfhydryl-deoxypolysaccharides and their derivatives, mureine, proteins, e.g. albumin, gelatin, collagene I-XII, keratin, fibrin and fibrinogen, casein, plasmaproteins, milk proteins, crospovidone, structure proteins from animal and plant tissue, soy proteins, proteins of the food industry.

Preferred are the following polymers for separation membranes:

silica, silicones, polyolefins, polytetrafluoroethylene, polyester urethane, polyether urethane, polyurethanes, polyethylene terephthalates, polymethylpentane, polymethylpentene, polysaccharides, polypeptides, polyethylene, polyester, polystyrene, polysulfonates, polypropylene, polyethersulfones, polypyrroles, polyvinyl pyrrolidones, polylactic acid, polyglycolic acid, polyorthoesters, polyaromatic polyamides, sepharose, carbohydrates, polycarbonate, copolymers of acrylates or methacrylates and polyamides, acrylic acid ester, methacrylic acid ester, acrylic acid amide, methacrylic acid amide, polyacrylnitrile, copolymers of ethylene glycol diacrylate or ethylene glycol dimethacrylate and glycidyl acrylate or glycidyl methacrylate and/or allylglycide ether, regenerated cellulose, acetylcellulose, hydrophobic polymers by adding hydrophilic polymers, e.g. polysulfone polyvinyl pyrrolidone, derivatives and copolymers of aforesaid polymers.

Poly(isohexyl cyanoacrylate) (PIHCA), poly(isobutyl cyanoacrylate) (PIBCA), poly(hexyl cyanoacrylate) (PHCA), poly(butyl cyanoacrylate) (PBCA), poly(2-dimethylamino)ethylmethacrylate (PDMAEMA), polymonomethylamino-ethylmethacrylate (PMMAEMA), poly-N-trimethyl-aminoethylmethacrylate (PTMAEMC), polyaminoethyl-methacrylate (PAEMC), Polyaminoethyl-methacrylamide (PAHMAC), Polyaminohexyl-methacrylate (PAHMC), Polystyrol (PS), Polyvinylpyrrolidon (PVP), Polyvinylalkohol (PVA), Poly(lactic-co-glycolic acid) (PLGA), Polyethylenimin (PEI).

Inorganic materials include but are not restricted to metals like aluminium, iron, magnesium, copper, gold, zirconium, iridium, titanium, zinc, tin, as well as their oxides, silicon and it oxides, as well as silicon complexes as silicon carbide (SiC), to be used alone or combined with substances such as silicon nitride, aluminium nitride, molybdenum disilicide and tungsten carbide, alternatively carbon and its oxides, as well as boron nitride (BN), boron carbide ($B_4C$).

3.4 Hollow Porous Capillaries or Tubes

In general, all polymeric or ceramic materials as well as carbon tubes are suitable for separable membranes as listed above are likewise suitable for hollow capillaries.

Materials and dimensions vary for the various applications.

For Medical Use

The length of the hollow fibers is between 30-500 mm, preferred between 50 and 300 mm. The outer diameter of such a hollow fiber became 0.1-1.5 mm, the inner diameter is 0.01-1 mm and the wall thickness of the hollow capillary should be 5-200 µm, preferred 15-50 µm.

For Industrial Use

The hollow fibers or tubes can have a length between 150 mm to 2000 mm, preferred between 500 mm and 1000 mm. The outer diameter of such a hollow fiber or tube can be between 1.5 mm and 10 mm, the inner diameter between 1 mm and 4 mm and the wall thickness of the hollow capillary should be 200 µm to 500 µm, preferred 300 µm to 400 µm.

The walls of the hollow capillaries or tubes can contain pores. The porosity of the inner and outer surface of the hollow capillaries or tubes made from membrane permeable for gas is in the range of 10 to 90%. The average diameter of the pores is in the range of 0-5 µm and preferred 0-1.5 µm. Virtually all polymeric materials are suitable to build hollow capillaries or tubes. Especially preferred is polyacrylonitril. Also composite materials made from organogels and polymers are suitable, likewise ceramics, cellulose and combinations of these materials.

4. Materials for Surface Functionalization

The compounds being most appropriate largely depend on the carboxylic acids that should be separated. One or more compounds can be used. In principle, the net zeta-potential of the interface should have a positive or neutral charge and the surface should have organophilic/lipophilic and hydrophobic properties. Compounds can be organic or inorganic as well as combinations thereof. They include but are not resctrictied to aliphatic or cyclic hydrocarbons as well as complex compounds thereof like cholesterin, cholic acid and its derivates like chenodeoxycholic acid and ursodesoxycholic acid, tetraether lipids and its conjugates.

Most preferred are molecules having a cationic charge like cycloheptatrienyl cation, or have an electrophilic substituent like iodine or bromine.

Further preffered are molecules exhibiting amino groups (primary, secondary, tertiary, quaternary) like cholin, ethanolamine, dimethylamine, triethylamine, betaine and analoges.

Further preferred are aromatic carbon molecules having 2 or more nitrogen atoms like diazine like imidazole, imidazol, purine, pyrazol, pyrimidine, pyridazine, and triazine like atrazin, simazin, melamin, more specifically 2,4,6-triphenylpyrylium tetrafluoroborate (2,4,6-TPPT) and 1,3-benzodithiolylium tetrafluoroborate (1,3-BDYT), bromobenzenediazonium-, nitronium-, benzodithiolylium-, and triphenylpyrylium tetrafluoroborate.

Further preferred compounds are arginine and its derivatives like: 5-(diaminomethylideneazaniumyl)-2-oxopentanoate known as oxoarginine, (2S)-2-amino-5-[(N'-methyl-carbamimidoyl)amino]pentanoic acid, known as omega-methyl-arginine; 2-amino-5-(diaminomethylideneamino)-N-(4-nitrophenyl)pentanamide, known as arginine-4-nitroanilide; 2-benzamido-5-(diaminomethylideneannino)pentanoic acid, known as benzoyl-L-arginine; (2S)-2-[[(2S)-2-amino-5-(diaminomethylideneamino)pentanoyl]amino]-5-(diaminomethylideneamino)pentanoic acid, known as arinylarginine, 2S)-2-[[(2S)-2-amino-3-phenylpropanoyl]amino]-5-(diaminomethylideneamino)pentanoic acid, known as phenylalanylarginine; (2S)-2-amino-4-(diaminomethylideneamino)butanoic acid, known as L-norarginine; [1-amino-4-(diaminomethylideneamino)butyl]-hydroxy-oxophosphanium; (2S)-5-(diamino-methylideneamino)-2-[(4-hydroxy-4-oxobutanoyl)amino]pentanoic acid, known as succinyl-L-arginine; (2S)-2-amino-5-[[amino(dimethylamino)methylidene]amino]pentanoic acid, known as N,N-dimethyl-L-arginine; (2S)-2-(3-aminopropanoylamino)-5-(diaminomethylideneamino)pentanoic acid, known as beta-alanyl-L-arginine, 2-amino-5-[[amino-(phosphonoamino)methylidene]amino]pentanoic acid, known as phosphoarginine; 2-[[(2R)-5-(diaminomethylideneazaniumyl)-1-oxido-1-oxopentan-2-yl]azaniumyl]pentanedioate, known as nopaline; 5-(diaminomethylideneamino)-2-[(1-hydroxy-1-oxopropan-2-yl)amino]pentanoic acid, known as octopine; (2S)-2-amino-5-[[amino-(hydroxyamino)methylidene]amino]pentanoic acid, known as hydroxyarginine; (2S)-2-(2-carboxyethylamino)-5-(diaminomethylideneamino)pentanoic acid, known as L-N2-(2-carboxyethyl)arginine; [(48)-4-azaniumyl-5-hydroxy-5-oxopentyl]-(diaminomethylidene)azanium, known as arginedium; 4-(diaminomethylideneamino)butanamide, known as augmentin;

and compounds containing arginine and arginine-related molecules like: arginyl-phenylalanine anilide, 2-(4-aminobutyl)guanidine, known as agmantine and its structural analogs; 2-(1-aminobutyl)guanidine; 2-(4-aminobutyl)guanidine hydrochloride; 2-(4-aminobutyl)-1-bromoguanidine; 2-(4-aminobutyl)-1-chloroguanidine; 2-(1-aminopropyl)guanidine; 2-(1-aminopropyl)-1-(diamino-methylidene)guanidine; 2-(3-aminopropyl)-1-(diaminomethylidene)guanidine; 2-(3-aminopropyl)guanidine; 4-aminobutyl(diaminomethylidene)azanium; diaminomethylidene-[3-(diaminomethylideneamino)propyl]azanium; 2-[3-(diaminomethylideneamino)propyl]guanidine; 4-(diaminomethylideneamino)butanamide; 2-(4-aminobutyl)-1-(difluoromethyl)guanidine; [1-(diaminomethylidene) piperidin-1-ium-4-yl]methylazanium; [4-(aminomethyl)piperidin-1-ium-1-ylidene]methanediamine; 3-(2-aminoethyl)-2,5-dihydropyrrole-1-carboximidamide; 3-(2-aminoethylsulfanyl)-1H-1,2,4-triazol-5-amine; 2-[3-(dimethylamino) propyl]guanidine; 3-(2-aminoethyl)azetidine-1-carboximidamide; 2-(3-aminopropyl) guanidine; 4-(aminomethyl)cyclohexane-1-carboxinnidamide; 2-[2,2-bis(sulfanyl)ethyl]guanidine; 5-(aminomethyl)thiophene-3-carboximidamide; diaminomethylidene-[4-(diaminomethylideneazaniumyl)butyl]azanium; [amino-(diaminomethylideneamino)methylidene]-butylazanium, [amino(butylazaniumylidene)methyl]-(diamino-methylidene)azanium; butyl(diaminomethylidene)azanium;

Furthermore phenylalanine and its derivates like:
4-guanidinophenylalanine; N-guanyl-dl-phenylalanine; (2S)-2-[[(2S)-2-amino-5-(diaminomethylideneannino)pentanoyl]amino]-3-phenylpropanoic acid, known as arginylphenylalanine; (2S)-2-amino-3-[4-[(diaminomethylideneamino)methyl]phenyl]propanoic acid; 2-amino-3-phenylpropanehydrazide; (2S)-2-[[(2S)-2-amino-3-phenylpropanoyl]amino]-5-(diaminomethylideneamino)-N-naphthalen-2-ylpentanamide; and polyphemusin I or II.

Furthermore guanidine and its derivatives like
Urea; 2-methylguanidine; 2-[4-[4-(diaminomethylideneamino)phenyl]phenyl]guanidine; 3-(diaminomethylideneamino)-5-[(diaminomethylideneamino)methyl]benzoic acid; (2S)-2-amino-3-[4-(diaminomethylideneamino)phenyl]propanoic acid; 2-[2-(azocan-1-yl)ethyl]guanidine known as sanotensin; N-(diamino-methylidene)-2-(2,6-dichlorophenyl)acetamide known as guanfacin; 2-[(3-iodophenyl)methyl]guanidine; 2-methylguanidine; 2-butyl-1-

(diaminomethylidene) guanidine; 2-[(E)-[(1E)-1-(diaminomethylidenehydrazinylidene)propan-2-ylidene]amino]guanidine; 2-[3-(1H-imidazol-5-yl)propyl]-1-[2-[(5-methyl-1H-imidazol-4-yl)methylsulfanyl]ethyl]guanidine; 2-[(3-iodanylphenyl)methyl]guanidine; 2-[iodo(phenyl)methyl]guanidine; 2-benzylguanidine; [(E)-N'—(N'-benzylcarbamimidoyl)carbamimidoyl]azanium; benzyl(diaminomethylidene)azanium; 2-[[4-[(diaminomethylideneamino)methyl]phenyl]methyl]guanidine; 4-phenyl-1,4-dihydro-1,3,5-triazine-2,6-diamine; 2-[[4-[[[amino-(diaminomethyleneamino)methylidene]amino]methyl]phenyl]methyl]-1-(diaminomethylidene)guanidine; 2-(2H-tetrazol-5-yl)guanidine; 4-[5-(4-carbamimidoylphenoxy)pentoxy]benzenecarboximidamide; 2-[carbamimidoyl(methyl)amino]acetic acid known as creatinine; 4-[2-(4-carbamimidoylphenyl)iminohydrazinyl]benzenecarboximidamide; 1-cyano-2-methyl-3-[2-[(5-methyl-1H-imidazol-4-yl)methylsulfanyl]ethyl]guanidine hydrochloride; 2-[(Z)-[(1Z)-1-(diaminomethylidenehydrazinylidene)propan-2-ylidene]amino]guanidine; 1-N-[amino-(4-chloroanilino)methylidene]-1-N'-[N'-(4-chlorophenyl)carbamimidoyl]piperazine-1,4-dicarboximidamide, methylglyoxal bis(guanylhydrazone) (known as mitoguazone); and biguanidines like 3-(diaminomethylidene)-1,1-dimethylguanidine known as metformin; (1E)-2-[6-[[amino-[(E)-[amino-(4-chloroanilino)methylidene]amino]methylidene]amino]hexyl]-1-[amino-(4-chloroanilino)methylidene]guanidine, known as chlorhexidine; dimethyloctadecyl[3-(trimethoxysilyl)propyl]ammonium chloride; octadecyl-guanidinium chloride; 1,10-bis(4-chlorophenyl)-1,3,5,10,12,14-hexazadispiro[5.2.5ˆ9.2ˆ(6)]hexadeca-2,4,11,13-tetraene-2,4,11,13-tetramine; 3,5-dimethyl-4-phenyldiazenylpyrazole-1-carboximidamide hydrochloride; N,N'-dioctadecyl-guanidinium chloride; 2,2,8,8-tetraalkyl-3,4,6,7,8,9-hexahydro-2H-pyrimido-[1,2-a]-pyrimidine; 3-(diaminomethylideneamino)propanoic acid; 2-[5-(diaminomethylene-amino)pentyl]guanidine; 2-[4-(3-aminopropylamino)butyl]guanidine: 2-(diamino-methyleneamino)acetic acid; 3-(diaminomethylideneamino)benzoic acid.

Furthermore aminines such as

Butanimidamide; decanimidamide hydrochloride; 4-[4-(4-carbamimidoylphenyl)phenyl]benzenecarboximidamide; N,N-dimethyl-N'-(4-phenylmethoxyphenyl)methanimidamide.

Furthermore amino acids, most preferred phenylalanine, isoleucine, leucine, valine, arginine, lysine, histidine, tryptophan, tyrosine, proline.

Furthermore peptides consisting of one or more of these amino acids. Most preferred is the "RDG"-peptide sequence (Arg-Asp-Glyc); and proteins and macro molecules with known lipophilic properties like albumine, fatty acid binding proteins, or having fatty acid binding properties like apolipoproteins, lactoglobulins, caseine. Furthermore cyclodextrins or porphyrins and the like, and substances like chlorin and corpin.

Amines and polyamines such as choline(2-hydroxyethyl(trimethyl)azanium); phosphocholine, betaine (2-(trimethylazaniumyl)acetate); neostigmine; 2-[2,3-bis[2-(triethylazaniumyl)ethoxy]phenoxy]ethyl-triethylazanium triiodide; [(2R)-2,4-dihydroxy-4-oxobutyl]-dimethyl-(trideuteriomethyl)azanium known as carnitine; 3-hydroxy-4-(trimethylazaniumyl)butanoate; 4-azaniumylbutyl(3-azaniumylpropyl)azanium, known as spermidine; 3-azaniumylpropyl-[4-(3-azaniumylpropylazaniumyl)butyl]azanium, known as gerontine.

Furthermore peptide-carboxylate conjugates such as (2S)-2,5-bis(3-aminopropylamino)-N-[2-(dioctadecylamino)acetyl]pentanamide, known as transfectam; 6-amino-2-[[(2S)-2,5-bis(3-aminopropylamino)pentanoyl]amino]-N,N-dioctadecylhexanamide; 2-amino-6-[[2-[3-[4-(3-aminopropylamino)butyl-amino]propylamino]acetyl]amino]-N,N-dioctadecylhexanamide; and peptides such as (2S)-2-[[2-[[(2S)-2-amino-5-(diaminomethylideneamino)pentanoyl]amino]acetyl]amino]butanedioic acid, known as RGD-peptide; (2S)-2-[[(2S)-2-amino-5-(diaminomethylideneamino)pentanoyl]amino]butanedioic acid, arinine-asparagine-dipeptides, and polypeptides like 2-[[2-[[2-[[2-amino-5-(diaminomethylideneamino)pentanoyl]amino]-5-(diaminomethylideneamino)pentanoyl]amino]-5-(diaminomethylideneamino)pentanoyl]amino]butanedioic acid; 2-[[2-(2,6-diaminohexanoylamino)-5-(diaminomethylideneamino)pentanoyl]amino]butanedioic acid; 4-amino-2-[[2-amino-5-(diaminomethylideneamino)pentanoyl]amino]-4-oxobutanoic acid; 2-[[6-amino-2-[[2-amino-5-(diaminomethylideneamino)pentanoyl]amino]hexanoyl]amino]butanedioic acid, known as thymotrinan; 2-[2-[[2-[[2-amino-5-(diaminomethylideneamino)pentanoyl]amino]-5-(diaminomethylideneamino)pentanoyl]amino]propanoylamino]butanedioic acid; 3-[[2-amino-5-(diaminomethylideneamino)pentanoyl]amino]-4-[(1-hydroxy-1-oxopropan-2-yl)amino]-4-oxobutanoic acid; (2R)-2-[[(2S)-2-azaniumyl-5-(diaminomethylideneazaniumyl)pentanoyl]amino]butanedioate.

Furthermore proteins like: albumine, protamine, gelatine, natriuretic peptides.

5. Acceptor-/Adsorbent-Molecules/Materials

The process of adsorption is defined as adhesion of molecules to a surface. Based on the bonding nature between the molecule and the surface adsorption phenomena can be divided into two categories: Physisorption and chemisorption. In physisorption, no chemical bonds are formed and the attraction between the adsorbent and the adsorbate is based solely on intermolecular electrostatic forces, such as Van der Waals forces. In chemisorption, the adsorbate adheres to the solid under formation of chemical bonds with the surface.

If the associates of carboxylic acid and solubilizing compound are adsorbed in a second cavity chamber or a second container an adsorbent must be provided which is suitable for adsorbing these associates.

The compounds and/or materials can be of natural or synthetic origin. Examples for groups of adsorbent materials which can be used in this invention include, but are not limited to zeolites, clays, activated carbon, activated alumina, natural and synthetic polymers, alkanes, proteins, and silica gels. The absorbent materials can be used in different forms such as beads, membranes, fibers or coatings. The combination of different absorbent materials is also possible.

Zeolites are microporous aluminosilicate minerals with a porous structure that can accommodate wide variety of cations. The shape-selective properties of zeolites are also the basis for their use in molecular adsorption. They have the ability to preferentially adsorb certain molecules, while excluding others. Examples for zeolites include, but are not limited to, amicite, analcime, barrerite, bellbergite, bikitaite, boggsite, brewsterite, chabazite, clinoptilolite, cowlesite, dachiardite, edingtonite, epistilbite, erionite, faujasite, ferrierite, garronite, gismondine, gmelinite, gobbinsite, gonnardite, goosecreekite, harmotome, herschelite, heulandite, laumontite, maricopaite, mazzite, merlinoite, mesolite, montesommaite, mordenite, natrolite, offretite, paranatrolite, paulingite, pentasil, perlialite, phillipsite, pollucite, scolecite, sodalite, sodium dachiardite, stellerite, stiolbite, tetranatrolite, thomsonite, tschernichite, wairakite, wellsite, willhendersonite, and yugawaralite.

Clays are a mineral substance made up of small crystals of silica and alumina. Clay minerals are divided into four major groups: the kaolinite group, the montmorillonite/smectite group, the illite group and the chlorite group. Examples for clays include, but are not limited to, kaolinite, dickite, nacrite, pyrophyllite, talc, vermiculite, sauconite, saponite, nontronite, montmorillonite, illite, amesite, baileychlore, bentonite, chamosite, kaemmererite, cookeite, corundophilite, daphnite, delessite, gonyerite, nimite, odinite, orthochamosite, penninite, pannantite, rhipidolite, sudoite and thuringite.

Activated carbon, also called activated charcoal or activated coal, is a form of carbon that has been processed to make it extremely porous and thus to have a very large surface area available for adsorption or chemical reactions. Based on their physical characteristics there can be distinguished powdered-, granular-, extruded-, impregnated- and polymer coated-carbon.

Silica gel, an oxide of the element silicon, is an amorphous, highly porous, partially hydrated form of silica. Silica occurs naturally but can also be prepared synthetically. Crystalline silica is the anhydride of silicic acid and thus silica gel is a polymeric form of silicic acid. Also pyrogenic silica like Aerosil® or phyllosilicates such as talc, hectorite and montmorillonite can be used as well as polymeric coatings thereof.

Also useful are synthetic polymers that are composed of large numbers of highly crosslinked microspheres. This macroreticular structure gives it a high surface area and uniform pore size. Examples for synthetic polymers include, but are not limited to, polyacrylate, polyamide, polyester, polycarbonate, polyimide, polystyrene, acrylonitrile butadiene styrene, polyacrylonitrile, polybutadiene, poly(butylene terephthalate), poly(ether sulfone), poly(ether ether ketone), polyethylene, poly(ethylene glycol), poly(ethylene terephthalate), polypropylene, poly(methyl methacrylate), polyetheretherketone, polytetrafluoroethylene, styrene-acrylonitrile resin, poly(trimethylene terephthalate), polyurethane, polyvinyl butyral, polyvinylchloride, polyvinylidenedifluoride, poly(vinyl pyrrolidone).

Preferred are poly(methyl methacrylate) and polyetheretherketone.

The binding capacity can be increased by functionalization of the surface of the aforesaid materials. This can be accomplished by molecules exhibiting organophilic properties. This property is shared with the molecules mentioned in the section Materials for surface functionalization. They can be used in preferred embodiments.

A preferred class are molecules exhibiting amino groups (primary, secondary, tertiary, quaternary), calcium or magnesium.

6. Organogels

The most common definition of a gel is that of a macroscopic solid, a fluid which has no steady state flow. In other words, a gel is a solid, jelly-like material that can have properties ranging from soft and weak to hard and tough. A three-dimensional structural network of crosslinks lends a structure to the gel.

Organogels are non-crystallin, non-glassy thermoreversible solid materials composed of a liquid organic phase which gelled in a three-dimensional cross-linked network. The properties of an organogel such as elasticity and firmness are determined by its solubility and particle dimensions. The liquid organic phase is gelled by low-molecular weight gelling agents, the so called gelators. Organogels are often based on the self-assembly of the organic molecules. Based on their characterization organogels can be divided into solid matrix and fluid matrix organogels. Solid gels are strong systems, which form a persistent rigid network at a specific temperature, while fluid gels are formed by transient networks. Whether the gels are solid-like, characterized by persistent rigid networks, such as vulcanized rubber, or liquid-like, characterized by transient networks, such as non-vulcanized natural rubber, can also be used to classify gels.

Almost all organic solvents can be successfully gelled, as comprised by the definition of aliphatic and aromatic hydrocarbons, such as heptanes, octane, nonane, decane, benzene, toluene, ethyl benzene, gasoline, kerosene, lubricating oil and the like petroleum fractions, and halogenated hydrocarbons such as methylene chloride, chloroform, carbon, tetrachloride, methylchloroform, perchloroethylene, propylene dichloride, methylene bromide, ethylene dibromide, butyl bromide, allyl chloride, and propargyl bromide or chloride. Other types of organic liquids have been gelled, such as mineral and vegetable oil, lecithine, polysiloxanes, paraffins, nematic and smectic liquid-crystalline materials, electrolytes, polymerizable liquids and others.

The organic fluids are gelled by low molecular weight organogelators or polymeric gelators. The organogelators create a three-dimensional network by entanglement of nanofibers or nanoribbons formed by self-organization through noncovalent interactions such as hydrogen bonding, van der Waals, π-stacking, and coordination. Due to the nature of the intermolecular interaction the gel formation is a thermoreversible process.

A certain gelator can gel certain solvents. A requirement for the gelation process is a poor solubility of the gelator, because a compound with poor solubility and disinclined to crystallize will most probably form a gel. The solvent is then trapped in the network pores and microcrystals of the gelator by capillary forces.

Molecules which can act as LMWG (low molecular weight gelator) comprise fatty acid derivatives, steroid derivatives, anthryl derivatives, gelators containing steroidal and condensed aromatic rings, amino-acid type organogelators, miscellaneous types of gelators and two-component systems.

As LMWG are used for example hydrocarbons, haloalkanes, alcohols, acetone, alkanes, cycloalkanes, hexadecanes, cyclohexanes, toluene, p-xylene, cyclohexanone, dichloroethane, DMSO, ethanol, propanol, mineral oil, kerosene, chlorobenzene, rapeseed oil, ethyl acetate, dialkylphtahalates, DMF, DMA, dioxin, silicon oil, $CHCl_3$, $CH_2Cl_2$, $CCl_4$, aromatic hydrocarbons, pyridine, acetonitrile, ketones, diethylether, halogenated alkanes, aliphatic hydrocarbons, aliphatic alcohols, aliphatic amines, methanol, oils, tetralin, dedecane, long chain apliphatic hydrocarbons, cycloalkanles, alkyl laureates, trialkylamines, methacylates, and further metal soaps, fatty acids, perfluoroalkylalkanes, steroids, waxes, urea derivatives, cyclic bis urea compounds, terephthalamates, cholamides, carbohydrates, Gemini tensides, bolaform amino acid amides, camphoryl thiosemicarbazide, cyclopeptides, amino acid amides, proteins such as albumin or fatty acid binding protein, anthranyl, antryl derivatives, phenazines, trimesamides thiophenes, helicenes, lecithines, hydroxypropylmethyl cellulose, nitrocellulose or gelatin, macrocyclic gelators, cyclohexyl am ides, cyclohexanols, cholesterol derivatives, bola amphiphiles, alkali urates, guanylic acids, nucleosides, bromophenol blue, congo red deoxycholates, cholates and others.

Organogels are prepared by giving the gelator to the solvent which has to be gelled. This can either happen by adding the gelator to the solvent, mixing the solution and heating it if necessary until solution occurs. When cooling down, gelation occurs (hot gelation). The gelator can also be added to a small amount of solvent and heated until dissolved, which is then added to the solvent, mixed and set (cold gelation).

Organogels are used and have potential for use in a number of applications, such as pharmacy, drug delivery, cosmetics, art conservation and research.

The ability of the organogels to build self-organized structures provides a great potential in nanotechnology. Scientists have created organic gel materials that have nanoscale voids interconnected throughout mass formation. They allow mass transfer that is ruled by capillary forces.

Organogels can also be used as an enzyme immobilization matrix. Lipase have been described as being encapsulated in lecithin and microemulsion-based organogels formulated with hydroxypropylmethyl cellulose or gelatin. The entrapped lipase retained its ability to catalyse esterification reactions.

It is preferred to use organogels exhibiting nanovoids with lipophilic properties. A further preferred form of an organogel is the preparation of a xerogel.

7. Acceptor Solutions

Acceptor solutions can be aqueous, organic, or emulsions. Aqueous solutions should contain soluble or immobilized acceptor molecules as listed in 4. Materials for surface functionalization or acceptor material as listed in 5. Acceptor-/Adsorbent-molecules/materials.

Organic solutions can comprise alkanes, alkenes, alkines, carboxylic acids, esters, aldehyds, ketones, aromatic hydrocarbons, mono-, di- or triacylglycerols, silicone oils, organic solvents like n-hexane, esters, tetrahydrofuran, ketones, lactones, acetone, acetonitrile, nitromethan, nitroarane, dimethylformamide, alcohol, methylsilanes, octamethylcyclotetrasiloxane, amides like formamide, triethylamine.

8. Additives for Preparations of Solubilizing Compounds

A number of the solubilizing compounds such as arginine protonize in water which results from its characteristic as a base. The resulting pH depends on the respective concentration. Therefore this solubilizing compound can induce protein denaturation or cytolysis when used in a high concentration. Since these solubilizing compounds mostly are amphiphilic molecules they tend to aggregate by electrostatic interactions between the negatively charged carboxy group and the positively charged α-amino group at pH values >8, thus forming polymers. Therefore it can be advisable to protonize the inventive solution with the solubilizing compound to a certain extent in order to adjust the pH of the solution. Preferred protonating agents are short-chain carboxylic acids, hydrochloric acid (HCl), hydrobromic acid (HBr), sulfuric acid, phosphoric acid, formic acid, acetic acid, propionic acid, butyric acid, pentanoic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphersulfonic acid, china acid, mandelic acid, o-methylmandelic acid, hydrogen-benzenesulfonic acid, picric acid, adipic acid, D-o-tolyltartaric acid, tartronic acid, α-toluic acid, (o,m,p)-toluic acid, naphthylamine sulfonic acid, and other mineral acids and in particular acetic acid, citric acid, lactic acid, acetylsalicylic acid and salicylic acid, benzoic acid, ascorbinic acid, folic acid, or amino acids such as aspartic acid or glutamic acid.

A preferred pH for solubilisation of fatty acids in media is between 7.4 and 10.

9. Micro- or Nanoemulsion

The present invention also relates to microemulsions and nanoemulsions in a hydrophilic solvent and especially in water of a carboxylic acid including carboxylic diacids, triacids as well as tetraacids and especially fatty acids, fatty diacids, fatty triacids as well as fatty tetraacids and at least one solubilizing compound, wherein said solubilizing compound contains at least one amidino group and/or at least one guanidino group and wherein the compound has a partition coefficient between n-octanol and water of $K_{OW}$<6.30. Thus the inventive microemulsion and the inventive nanoemulsion contain at least one carboxylic acid and especially fatty acid and at least one solubilizing compound as disclosed herein.

The solubilizing compounds are disclosed above in detail and these solubilizing compounds form a microemulsion or a nanoemulsion with the carboxylic acid. The solubilizing compounds have the same preferred carbon atom number as disclosed above, the same preferred structure as disclosed above, are preferably arginine derivatives as disclosed herein, have the same preferred pH range for the solubilization reaction, the same preferred molar ratio of carboxylic acid to solubilization compound and the same preferred reaction conditions as disclosed above for the solubilization compounds in general.

Major Characteristics of Micro- and Nanoemulsions as Defined in Section B.

Essential is the spontaneous molecular self-assembly of the solubilizing substance and the carboxylic acid that is built by electrostatical forces as mentioned above. They are composed by dimers which have a low tendency to aggregate to micelles. In nanoemulsions all carboxylic acids may be bound to an inventive solubilizing substance creating a monophasic emulsion without micelles. The majority of vesicular structures measurable by dynamic light scattering (DLS) was <150 nm for an emulsion with a molecular ratio of 1:1, see also example 12. With a higher ratio of the solubilizing compound the measurable vesicles became smaller. At a ratio of 10:1 98% of the vesicles were <2 nm in diameter and no aggregates larger than 25 nm were found. This self-assembly of nanoparticles is a central characteristic of a nanoemulsion. The nanoemulsion is completely transparent and stable over more than 6 months at temperatures between −20 and 100° C. Decrease of pH by addition of acid (HCl) reduces the solvation capacity which could be overcome by addition of arginine. However, the pH of the solution is critical for the nanoemulsification capacity of arginine which decreases below pH 8.

A further central characteristic of the inventive use of micro- or nanoemulsions is the solubilizing/liberating effect due to reduction of surface tension. This enables penetration and flooding of nanoscaled voids and capillaries. The amphiphilic nature of the 1:1 aggregates enables adherence or adsorption to lipophile or hydrophile substances, respectively solids, thereby changing interfacial forces of aforesaid substances, respectively solids and/or allowing partition of the molecules of said inventive micro- or nanoemulsions and/or of molecules dissolved in said inventive micro- or nanoemulsions within or at aforesaid substances, respectively solids, and enabling solvation, liquefaction, detachment or convection of aforesaid substances, respectively solids as shown in examples 5, 9 and 10.

A decisive advantage of arginine or a solubilizing compound according to formula I or II is that a cosolvent is not necessary to build micro- or nanoemulsions. However, addition of a cosolvent can enhance the described solubilizing effect.

The microemulsions and nanoemulsions have preferably a pH value >7.0 and more preferably within a pH range of 7.0 to 9.0. However depending on the medium from which the carboxylic acids should be separated, pH values of the microemulsions and nanoemulsions up to pH 14 can be obtained, while a pH range between 7.0 and 8.0 is preferably used if the carboxylic acids should be removed from blood. However, if not complete solubilization is obtained which can be seen if the microemulsion or the nanoemulsion is not clear and/or not colorless, more solubilizing compound might be added or the pH value might be increased or both possibilities might be used until a clear and in most cases colorless microemulsion or nanoemulsion is obtained.

Furthermore, micro- or nanoemulgation of carboxylic acids can be used to enable, respectively to enhance or decrease, respectively to terminate chemical reactions thereof as known in the art. Non-ionic liquids or amphiphilic surfactants have been used to dissolve carboxylic acids for this purpose. However, the use of arginine or a solubilizing compound according to formula I or II for such changes in chemical reactivity was not reported so far. It was found that nanoemulgation enhanced chemical reactions of both the alkyl- and the carboxyl groups, as shown in example 11. The low ionic strength and a high stability those emulsions are decisive advantages as compared to ionic or non-ionic emulsifiers. Furthermore, they can be used as a reactant- or product-specific emulsifier that can be easily removed from the solubilized carboxylic acid as well as from an organic reaction solution (Example 9).

FIGURES

Figure 3:
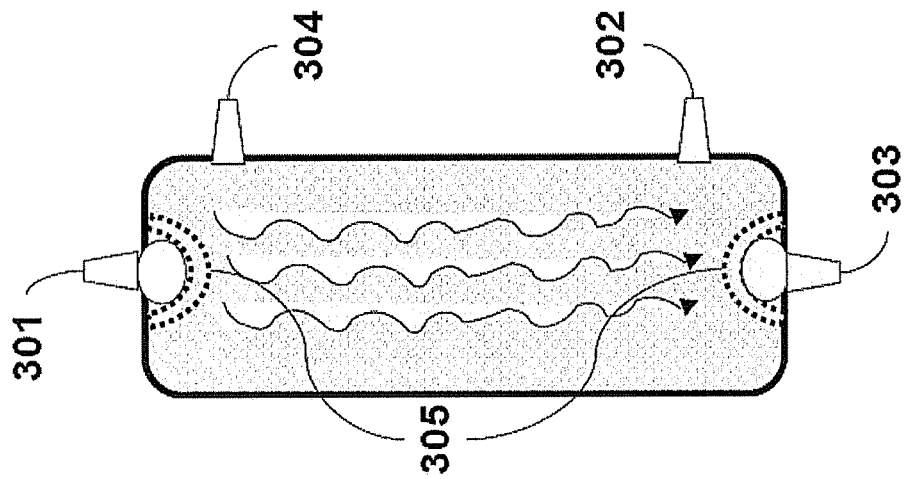
FIG. 3 shows a carboxylic acid exchange module.
Figure 1:
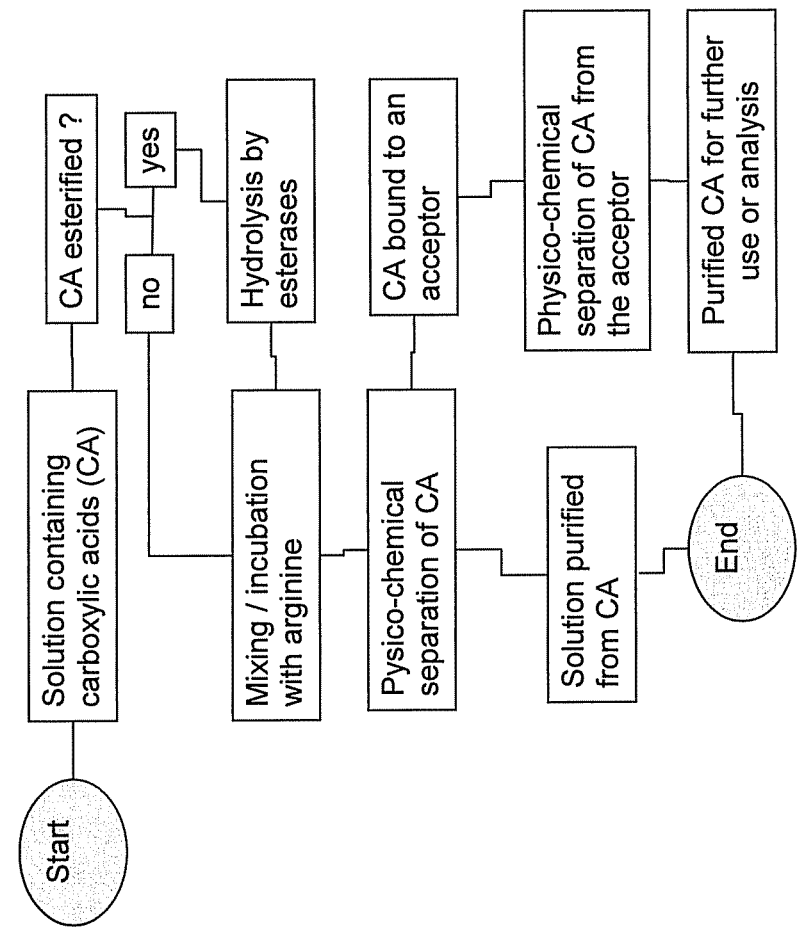
FIG. 1 is a flow diagram of the inventive solubilisation process and separation techniques.
Figure 2:
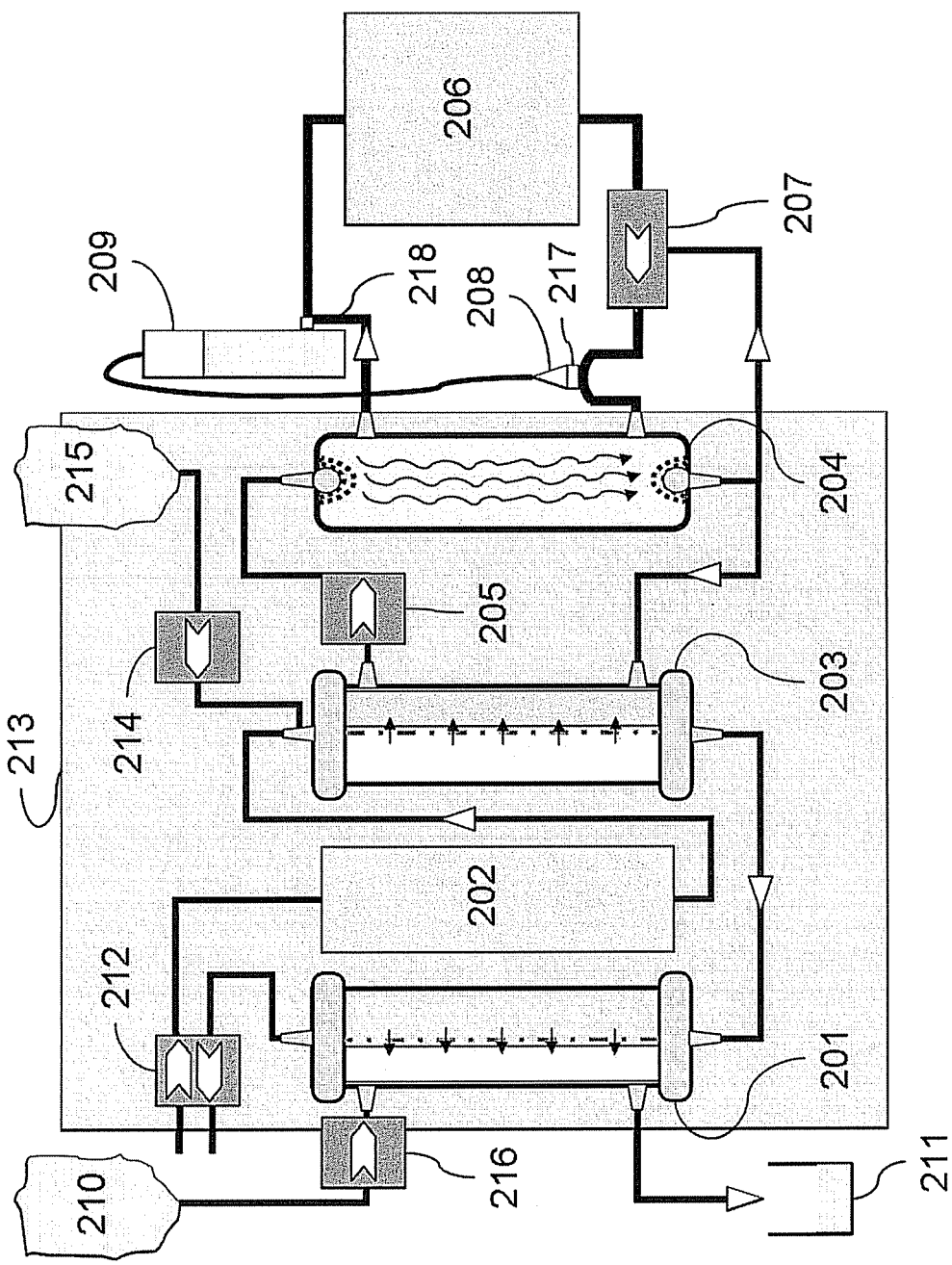
FIG. 2 is an integrated dialyser/extractor for purifying blood from volatile fatty acids.
Figure 4:
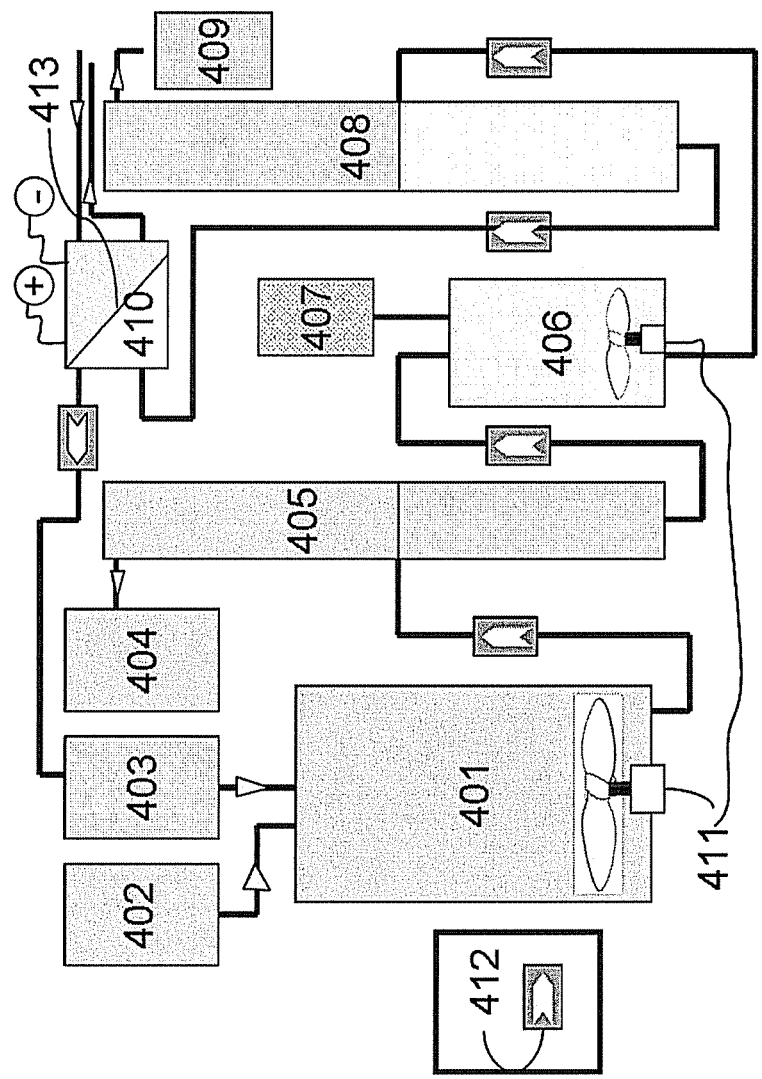
FIG. 4 is an integrated dialyser/extractor for solubilizing carboxylic acid impurities to be used in industrial oil processing.
Figure 5:
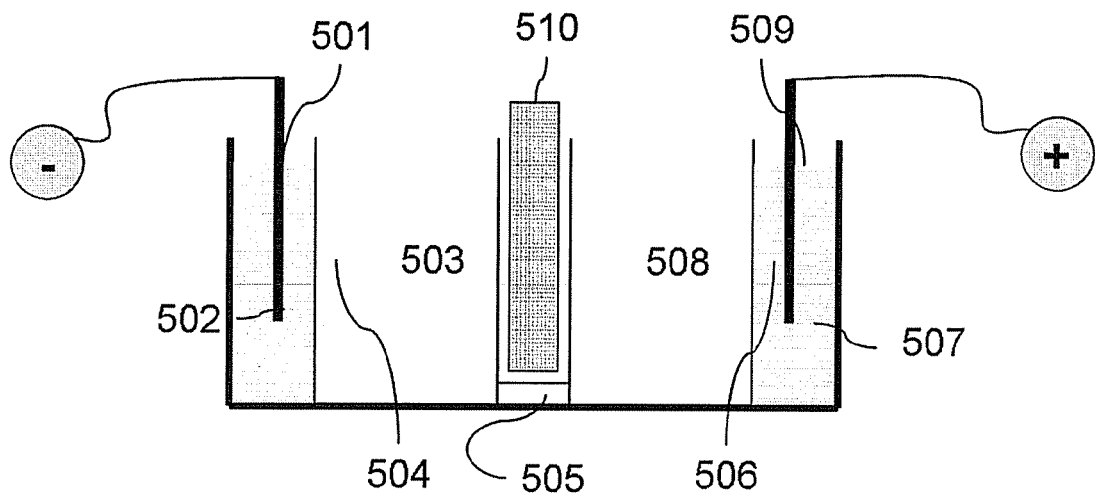

FIG. 5 refers to an electrophoretically- or electrostatically-driven filtration or diffusion for separation to be used with the inventive solubilisation.

Figure 6:
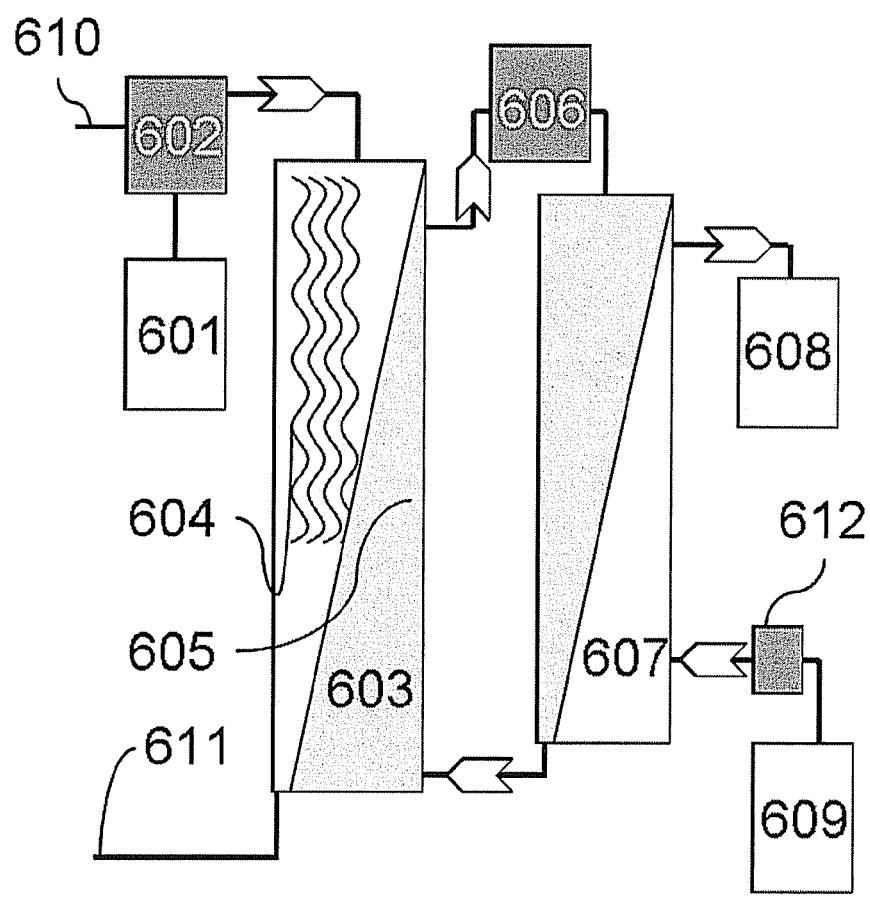

FIG. 6 shows an other embodiment of an integrated dialyser/extractor for purifying blood from volatile fatty acids.

Figure 7:
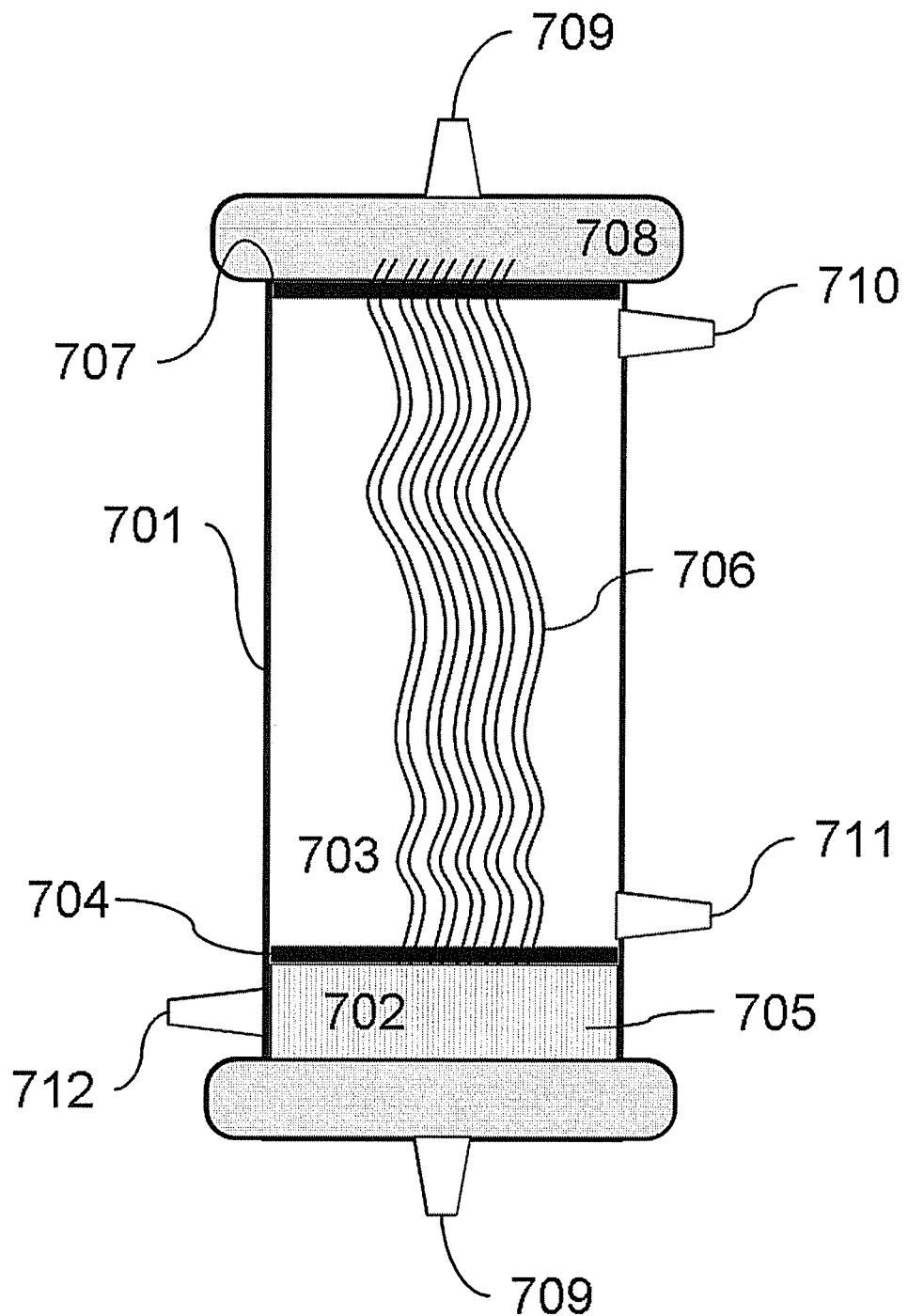

FIG. 7 depicts a typical integrated dialyser/extractor.

Figure 8:
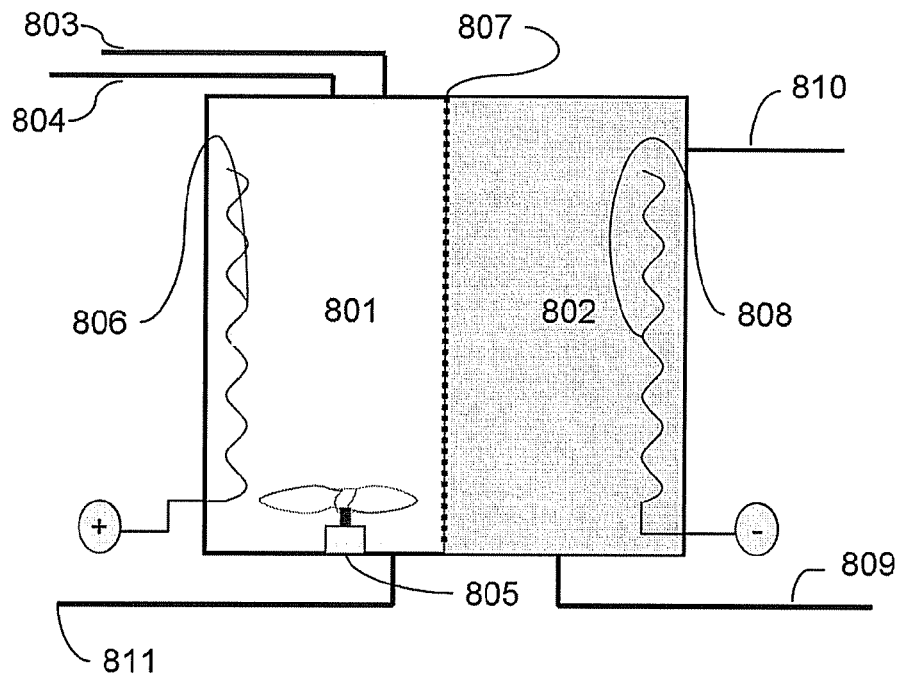

FIG. 8 refers an embodiment of an integrated dialyser/extractor to be used for crude oil processing, industrial food processing, in the processing of sewage containing bioorganic compounds or in any another industrial production or environmental technique.

Figure 9:
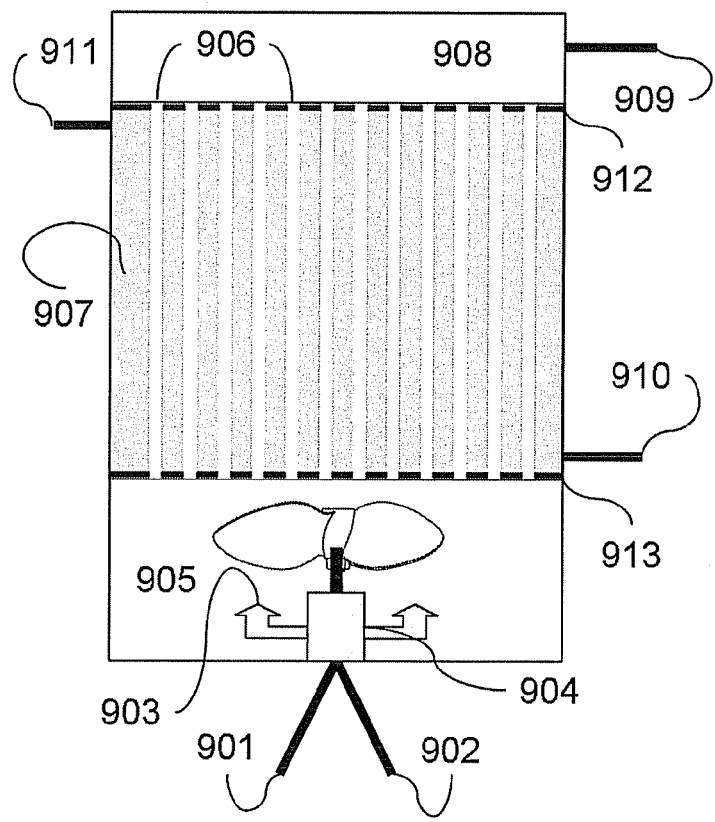

FIG. 9 shows the embodiment of a simplified integrated dialyser/extractor for industrial applications.

Figure 10:
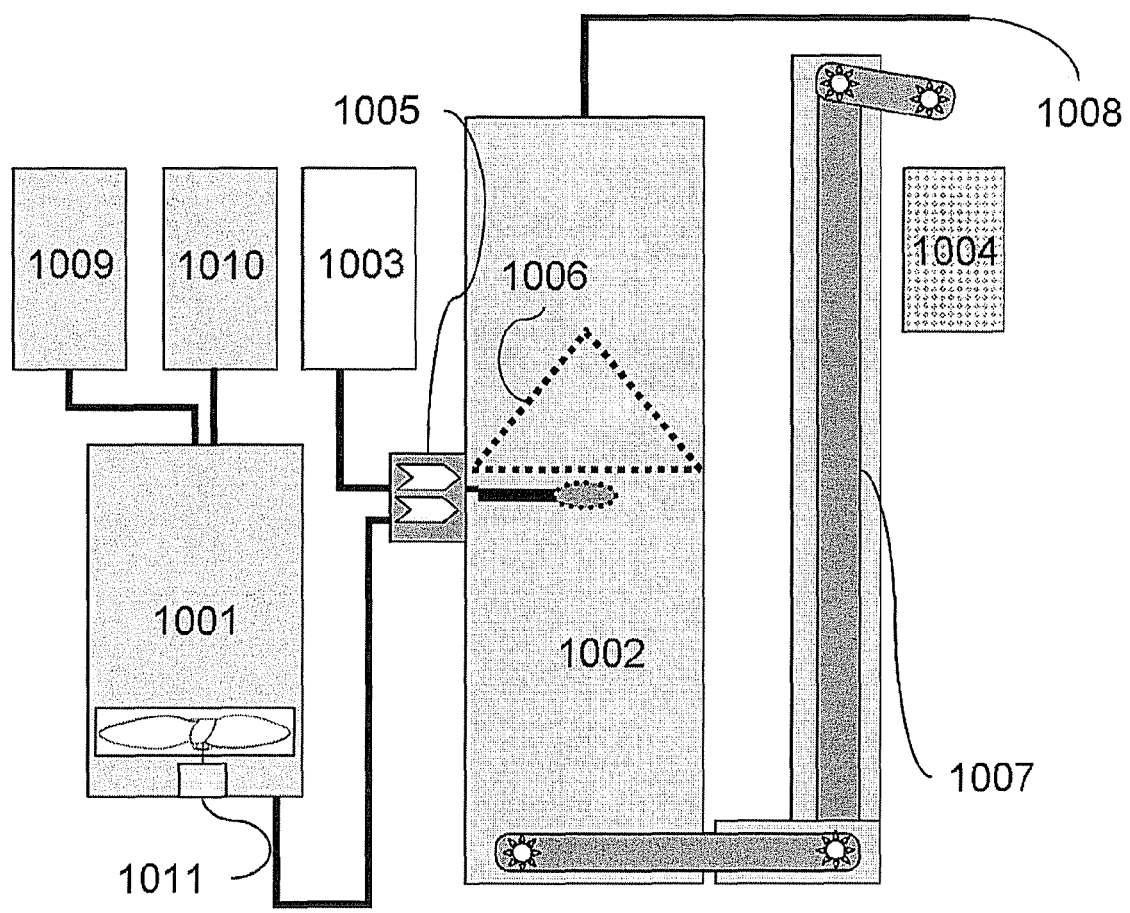

FIG. 10 refers to a further embodiment of a simplified integrated dialyser/extractor to be used for the solubilisation and separation of carboxylic acids from organic solutions consisting of proteins, amino acids and other water-soluble molecules during pharmaceutical, chemical, biological or industrial processing by means of fluid-fluid separation.

EXAMPLES

Example 1

Investigation of the Feasibility to Dialyse Fatty Acids from Plasma.

Non-esterified fatty acids although being small molecules are not dialysable when suspended in an aqueous medium because they form micelles because of their low CMC and therefore are too large to pass conventional micropores. The inventive solubilisation elevates the CMC and allows the formation of a nanoemulsion displaying a high partitition of the fatty acids. Therefore, the solubilised fatty acids are present as anions.

The use of the inventive solubilisation for refinement of plasma from volatile fatty acids was investigated in a dialysis model system. This system consisted of a dialysator cell connected to tubings, two reservoirs and two roller pumps. The dialysis cell consisted of two flattened glass hemispheres having flattened margins. The margins of both hemispheres were pressed against a Teflon membrane holder by a ferrule thereby sealing up the cavities. The dialysis membrane holder consisted of two Teflon O-rings that had a tongue and groove design to take up a membrane with a diameter of 47 mm and seal the membrane up by compressing both O-rings together. Each of the glass hemispheres had a drilling at the opposite poles where a glass funnel was mounted being connected with the glass of the hemispheres with the tip and with its basis being directed towards the membrane. The funnel is operated as an inlet. A further drilling of the hemispheres was connected with a glass tube operating as an outlet. In- and outlet were connected with PTFE tubings. The tubing connected with the inflow was intersected by a silicone tubing being part of the roller pump. The ends of the in- and outflow tubings joined in a PTFE reservoir which had a filling volume of 200 ml. The inflow tubing was interconnected with a Y-adapter which had a squeeze-type gasket through which a pressure sensor wire was advanced into the dialysis chamber and sealed to the outside. Investigations were performed in duplicate using one of the following membranes: Polycarbonate track-etch, 0.4 µm (Satorius, Germany); polyarylethersulfone with a 10,000 Dalton cut off (Gambro, Germany); PVDF with 40 kD (Rhone-Poulenc, France); PTFE, 0.05 µm (Sartorius, Germany); aluminium oxide (Anodisc), 0.02 µm (Whatman, USA).

Blood plasma from human source was used for the experiments. Oleic acid (technical grade, Sigma, Germany) was added as to achieve a 100 mmol solution. The prepared solution was allowed to dissolve during stirring at 37° C. for 10 minutes. Then 100 ml of deionised water or arginine solution (0.5 mol/l) was added in a volume ratio of 1:1. The donor site of the dialysis system was filled with 250 ml of that solution; care was taken to exclude air bubbles. The acceptor site of the dialysis system was filled with 250 ml of a 10% albumine solution. The roller pumps conveyed a volume of 200 ml/min through both hemispheres. Care was taken to maintain an identical pressure within both dialysis chambers, differences between hemisphere pressures were levelled by a valve interconnected in the outflow tubing. Dialyses were carried out for 30 min each. Sample volumes were taken after filling the system, every 10 minutes from the donor and the acceptor side. Aqueous samples were transferred in iso-octane and dried by nitrogen stream. Methylation was performed by adding methanol containing 2% sulphuric acid and heating the sample for 15 minutes at 70° C. Samples were resolved in water and iso-octane. The organic phase was separated after centrifuge and analyzed by GC.

Analysis showed that when dialysis was performed without arginine there was no or only minor amounts of oleic acid found in the acceptor solutions. In dialysis performed with arginine there was a proportional increase in the oleic acid content of the acceptor solution to the oleic acid concentration in the donor solution and the duration of the dialysis. This increase was lower when hydrophilic membranes like cellulose or polyarylethersulfone were used, and higher when hydrophobic membranes were used like PVDF and PTFE membranes.

In a further setting the feasibility of electrodialysis was investigated. For that purpose the described dialysator cell was modified by placing a platin mesh into both funnels. They were connected to a high voltage generator (EasyPhor, Biozyme, Germany) via sealed wires which were put through the Y-connectors. Dialyses were performed with the identical membranes as in the previous experiments and under the same conditions but applying a variable DC with a fixed voltage of 40V. Sample preparation was done as described before. Investigations were repeated using stearic acid and linoleic acid. Results found for oleic acid could be confirmed.

Conclusion: Solubilisation of fatty acids bound to plasma proteins using an arginine solution and separation of fatty acids by means of an electro-dialysis is feasible.

Example 2

Investigation of the Use of Arginine Solvation for Analysis of the Fatty Acid Content of Plasma Unesterified and esterified fatty acids have important functions in physiology. However, a disproportion of critical fatty acids is pathogenic in several diseases like atherosclerosis, hypertension or diabetes mellitus. Thus, there is a need for their exact determination for prevention, diagnosis and therapy control. Clinical routine analysis is established only for the determination of triglycerides. Available analytical methods for the determination of volatile fatty acids in blood are rare and expensive. Determination of triglycerides is done by default. However, results can only estimate the true content of esterified fatty acids because enzymatically liberated glycerine is determined. Since the content of fatty acids esterifed with glycerine can vary the actual concentration is ambiguous. In addition, there is no universal method to characterize fatty acids according to their classes.

A comparison of 10 blood samples between clinical routine methods for determination of the triglyceride fraction, the inventive analytic procedure and a reference procedure was performed.

For all measurements blood from fastening persons was drawn into a serum monovette. Samples were allowed to coagulate for 20 min and centrifuged at 3000 U/min for 15 min. Plasma was separated and homogenized before separation of sample volumes to up to 3 Eppendorf vials. Margarinic acid was used as an internal standard in samples used for GC and nano-organogel-electrophoresis.

Enzymatic Standard Procedure for Triglyceride Determination

The clinical procedure was performed by a standard enzymatic assay (Serum Triglyceride Determination Kit, Catalog Number TR0100, Sigma-Aldrich, USA). Samples were prepared as follows:

Free Glycerol Reagent (0.8 ml) was pipetted into each cuvette and 10 ml (0.01 ml) of water, Glycerol Standard were added. Then they were mixed by gentle inversion, and incubated for 5 minutes at 37° C. Initial absorbance (IA) of blank, standard, and sample at 540 nm versus water as reference was recorded. Reconstituted Triglyceride Reagent (0.2 ml) was added to each cuvette, mixed, and incubation continued at 37° C. for 5 minutes more. Final absorbance (FA) of blank, standard, and sample at 540 nm versus water as the reference was recorded. The concentrations of glycerol, true triglycerides and total triglycerides in the sample were calculated.

The reaction steps are shown in the following:

Triglyceride Assay Enzymatic Reactions:

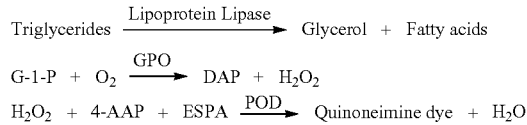

True Serum Triglyceride Concentration:

True Serum Triglyceride Concentration (equivalent triolein concentration)=

$$\frac{(FA_{SAMPLE} - (IA_{SAMPLE} \times F))}{(FA_{STANDARD} - (IA_{BLANK} \times F))} \times \text{Concentration of Standard}$$

Where F=0.81/1.01=0.80

Calculations:

Total Triglyceride Concentration in Serum or Plasma:

Total Serum Triglyceride Concentration (equivalent triolein concentration)=

$$\frac{(FA_{SAMPLE} - FA_{BLANK})}{(FA_{STANDARD} - FA_{BLANK})} \times \text{Concentration of Standard}$$

Glycerol in Serum or Plasma:

Glycerol Concentration (equivalent triolein concentration)=

$$\frac{(IA_{SAMPLE} - IA_{BLANK})}{(IA_{STANDARD} - IA_{BLANK})} \times \text{Concentration of Standard}$$

GC Measurements of Fatty Acids

Samples for GC determination were extracted according to the modified method of Folch (Folch, Lees & Sloan Stanley, 1957). In brief, 2 grams of a sample were weighed into a glass; 10 ml methanol+0.01% BHT were added, shaken and sedimented for a few minutes. CHCl$_3$ (20 ml) was added, the solution was shaken and sedimented for a few hours or over night in a refrigerator under N$_2$. The solution was filtered twice and 7 ml KCl were added and filled up to 250 ml with methanol. The lower fraction was then extracted by filtering through Na$_2$SO$_4$ into a clean large centrifuge tube and the solvent is evaporated. Then the lipid is transferred into a GC vial by adding 0.5 ml hexane+0.01% BHT into the tube, shaken well in other lipid dissolving, then using Pasteur pipettes all samples were transferred into a GC vial, GC was performed according to the following protocol: Aqueous samples were transferred in iso-octane and dried by nitrogen stream. Methylation was performed by adding methanol containing 2% sulphuric acid and heating the sample for 15 minutes at 70° C. Samples were resolved in water and iso-octane. The organic phase was separated after centrifuge and analyzed by GC.

Analysis of Fatty Acids with the Inventive Analytic Procedure

The analytic device was constructed as described before. In brief, a donor chamber and an analytic chamber are separated by a slot for placing the separation medium. The margins of the slot have gaskets which allow complete sealing between the chambers and the removable phase separation interface. Chambers for the anolyte and the catholyte are separated to the donor and the acceptor chambers, respectively, located at the opposite sites to the phase separation interface. Anolyte and catholyte chambers are separated to the donor and acceptor chambers by an ion selective membrane. In the anolyte and catholyte chambers platin electrodes (Umicor, Germany) were mounted which were connected to a high voltage generator (EasyPhor, Biozyme, Germany).

The disposable phase separation interface consisted of a PTFE O-ring having a diameter of 2.5 cm and a depth of 3 mm which was filled up to the margins with a liquid sol-gel-mixture. The organogel was prepared as described elsewhere (Suzuki et al: Two-component organogelators based on two L-Amino acids: Effect of Combination of L-Lysine with Various L-Amino Acids on Organogelation behaviour, Langmuir, 2009, 25, 8579-8585). After gelation, both sides of the organogel were covered with a Track-Etched polycarbonate membrane having pore diameters of 1.0 μm (Nucleopore, Whatman, USA), which were sticked to the margins of the O-ring. The phase separation interface was fitted tightly in the slot between the donor and acceptor chambers and controlled for tightness.

Plasma (1 ml) and 1 ml of an arginine solution (200 mmol/l) were vortexed for 2 min., incubated for 5 min at 40° C. and again vortexed for 2 min. Three commercial lipases (lipases A1 and A2 were pregastric lipases and lipase A3 was a fungal lipase) dissolved in toluol were added and gently mixed for 15 min at 37° C. The sample was weighed before and after pipetting 100 μl. The pipette volume was poured into the donor chamber of the analytic device. The acceptor chamber was filled with 100 μl acetonitril. Anolyte and catholyte chambers were filled with a 100 mmol/l arginine solution. DC at a potential of 40V was applied for 15 min. The acceptor chamber volume was pipetted and transferred into a probe. The acceptor chamber was washed with another 100 μl acetonitril which was added to the probe volume. Then measurement of fatty acids was carried out with a FT-NIR spectrometer MPA (Bucker Optic, Germany) From those measurements the fatty acid content of the whole sample was calculated.

Results: Comparison of the results from the three analysis methods show that (1) the enzymatic indirect method for determination of triglycerides underestimates the amount of fatty acids content in human blood when compared to both other methods, (2) results of the inventive analytic procedure and GC for the total amount of fatty acids are the same, and (3) determination of the various fatty acids with the inventive analytic procedure exhibits a high correlation with results from GC.

Example 3

Investigation of the Purification Capacity of Arginine and Other Solubilizing Compounds for the Refinement of Crude Vegetable Oils Crude vegetable oils contain various amounts of non-esterified fatty acids. Since those fatty acids reduce the stability of the oil they are separated during refinement processing to values below 0.5%. There are two methods performed in oil processing: Saponification and distillation. During these refinement processes alterations of the esterified fatty acids can occur. It was therefore intended to investigate the suitability of the inventive method to solubilise and separate non-esterified fatty acids with arginine and analyze the effects of the procedures on the quality of esterified fatty acids.

Crude oils from soy and rape were investigated. For that purpose 10 liters of crude oil were poured in a 50 liter tank. A 0.5 molar arginine solution was prepared by adding 871 g arginine to 10 liter deionized water. Arginine was allowed to solve by slow rotation and heating the solution to 40° C. for 2 hours. According investigations were performed using L-NG-monomethyl-arginin, argininosuccinic acid, L-canavanine, 2-guanidinoglutaric acid. The solutions were added to the crude oil and the emulsions were stirred for 1 hour while heating up to 40° C. Then the emulsions were allowed to settle for 24 hours. Thereafter the aqueous phases were drained through a hydrophilic sieve that can not be passed by triglycerides and which was located at the conic bottom of the tank. The aqueous solutions were weighed and samples were taken from the organic and the aqueous phases. Samples of the aqueous phases were acidified with sulfuric acid to a pH of about 3.

Samples of the organic phase were poured into a sample tube of a titration unit. To 5 ml of the organic phase 20 ml of a mixture of ethanol/hexane (1:1, v/v) with 3 drops 1% phenolphthalein in ethanol was added and stirred until the solution was completely clear. Then the samples were titrated with KOH in ethanol until a pinkish hue appeared, indicating the amount of non-esterified fatty acids. The fatty acids content was calculated according to the formula $$C_{FFA}[\text{mmol/l}] = (V_{KOH}[l] \cdot C_{KOH}[\text{mol/l}]) / V_{sample}[l] \cdot 1000$$

$V_{KOH}/C_{KOH}$: volume/concentration of consumed KOH in ethanol $V_{sample}$: applied volume of sample $C_{FFA}$: concentration of free fatty acids Samples of edible oil coming from the same source as the crude oil after industrial purification were analysed accordingly for their content of non-esterified fatty acids.

Furthermore, samples from the organic phases were hydrolyzed and analysed by GC as described before.

Results: Analyses showed that the content of non-esterified fatty acids of crude oil which initially was 2.0 and 2.6% can be lowered to 0.2 and 0.6% by using the inventive technique by means of fluid-fluid extraction in combination with the inventive solubilisation. The values found for non-esterified fatty acids were non-significantly lower than those after industrial removal thereof. Furthermore, comparison of the triglyceride fatty acids analysed by GC differed in their contents between the extraction methods. As compared to fatty acids of the organic phase of the foresaid fluid-fluid extraction fatty acids of the oil purified by saponification displayed a lower concentration of unsaturated fatty acids, while the contents of fatty acids with the same carbon number were about the same. On the other hand, the fatty acids of the oil purified by distillation exhibited more trans-isomers of the unsaturated fatty acids as compared to the fluid-fluid-extraction as well as a slightly less overall content of unsaturated fatty acids.

Example 4

Investigation on the Capacity of Arginine to Solve Lamer Amounts of Carboxylic Acids in Crude and Spent Oils Crude palm oil has a content of non-esterified fatty acids of up to 35%, and spent oils of up to 40%. For their commercial use the non-esterised fatty acids have to be removed. An aqueous extraction with an arginine solution was performed twice. 10 L of each crude oil were mixed with 30 L 0.5 mol/l arginine solution in a 50 L tank. The mixture is stirred for 15 minutes and allowed to separate for 5 h. The aqueous phase was drained off. Then the procedure was repeated with 10 L of a 100 mmol/l arginine solution. Analogous experiments were performed with solutions of 1,1-dimethylbiguanide, Arg-Gly-Asp, NG,NG-dimethylarginine, poly-L-arginine. An analysis of fatty acids was done according to example 2.

The contents of non-esterified fatty acids in the crude palm oil and the spend oil was 33% and 36%, respectively, which were reduced to a final concentration of 0.1 and 0.3% using arginine for extraction. The other tested compounds yielded reductions to final concentrations of 0.2-0.5, and 0.4-0.9%, respectively.

Conclusion: Carboxylic acids can be separated from various oils by aqueous solutions of arginine and comparative compounds, even when present in high concentrations.

Example 5

Investigation on the Capacity of Arginine and Other Solubilizing Compounds to Solve Carboxylic Acids and Crude Oil Ingredients Extractable oil fractions of plants and vegetables contain non-triglycerides at various contents that have to be removed in order to purify the oil product. Non-triglycerides comprise carboxylic acids, pigments, sterols, glycolipids, phospholipids, among others. Of those, amphiphiles like phospholipids, carboxylic acids and glycolipids aggregate to vesicles incorporating other non-triglycerides. The amphiphiles self-assemble to laminae and membranes. It was investigated whether the inventive solubilizing effect of the inventive compounds on vesicles of amphiphiles containing carboxylic acids is able to remove those carboxylic acids along with the amphiphiles complexed with the carboxylic acids.

Crude sun flower and maize oils were vigorously stirred with solutions of arginine, 4-guanidinobenzoeic acid, cimetidine, polyhexanide, and melamin (100 mmol/l; vol 1:1), respectively. The phases separated spontaneously resulting in a yellow-green-olive turbid aqueous phases and a creamy yellow oil phases. The aqueous phases were acidified with HCl in order to to achieve a pH of 5. Carboxylic acids were extracted by mixing with n-hexane, which was removed and analysed according to the methods described above. Results documented the presence of fatty acids in the analytes without a substantial difference in their content between the substances investigated. The remaining aqueous phases were further analysed by HP-TLC (LiChrosphere). Among substances that could be identified were: Phospholipids, green pigments, tocopherol, phytosterols. The total phosphate content in the oil phases was analyzed according to F-I 6(99) DGF. The free acid in the oil was determind by titration with ethanol KOH solution. It was found that more than 90% of non-esterified fatty acids have been removed after the first extraction with the investigated substances. The calculated total amount of extracted fatty acids correlated with the calculated amount of fatty acids recovered from the n-hexane extraction of the aqueous phases.

The phosphate contents of the crude oils were reduced by more than the half by the aqueous extraction procedures with the tested substances.

Conclusion: The inventive solubilizig effect of arginine and other solubilizing compounds can be used to liberate complexed carboxylic acids in solutions or emulsions of oils and amphiphiles enabling their extraction into an aqueous medium. Furthermore, amphiphiles complexed with the solubilized carboxylic acids can be separated (to an aqueous phase) at the same time to a large extent.

Example 6

Investigation of the Capacity of Arginine and Other Solubilizing Compounds to Liberate, Solve and Extract Complexed Carboxylic Acids from Solid Biological Materials Most biological materials contain non-esterified carboxylic acids usually complexed with other organic materials. One of these solid materials is rice bran which contains fatty acids and oils in up to 35% of its dry weight. Superfine milled rize bran was suspended in a 200 mmol/l solutions of arginine, Nw-nitro-L-arginine, octopine, 2-guanidinoglutaric acid, and agmantin, respectively. Solutions were continuously stirred for 24 hours. The solutions turned beige-grey and were very turbid in all cases. Solid matter was filtered off. The aqueous phases which had a pH of between 8-10 with the substances used were extracted with diethylether. Thereafter the aqueous solutions were acidified with ascorbinic acid in order to achieve a pH of 6.

Extractions of non-esterified carboxylic acids as well as their determination were performed as in example 5. The fractions extracted with diethylether were dried and weighed. Thereafter they were resolved and analyzed by HP-TLC according to example 5. The same was done for the residual aqueous solutions.

Results: The diethylether fractions contained triglycerides typically found in rice oils, the content was not significantly different between the substances used. The weight of the triglycerides corresponded to about 10-15% of the dry weight of the rice bran. The n-hexane fractions contained carboxylic acids and in the residual aqueous phases amphiphils like phospholipids and glycolipids could be identified as well as pigments.

Conclusion: Carboxylic acids frequently remain in organic solids that arise during food processing and which are commonly complexed with phospholipids and other lipids. An aqueous solution of arginine or other solubilizing compounds is able to liberate these complexed carboxylic acids, thereby also reducing the adhesion of phospholipids and other lipids to the solid material, thus allowing their aqueous extraction.

Example 7

Investigation of the Capacity of Arginin to Solve and Extract Aggregated Carboxylic Acids in Mineral Oils Fossile oils contain significant amounts of carboxylic acids that cause corrosion during oil refinement. Therefore there is a demand to lower the content of carboxylic acids. The most common carboxylic acid in mineral oils is naphthenic acid. The capacity of the solubilizing compounds to separate the carboxylic acid content of a crude oil sample was investigated. The oil was a gift from an oil processing company and had a density of 0.85 g/cm$^3$. The TAN (total acid number) was determined by KOH titration.

100 ml crude oil (containing about 40 mmol carboxylic acids) was mixed with 200 ml of a 300 mmol/l solution of either arginine or L-2-amino-3-guanidinopropionic acid, or L-canavanine in water for 1 h at 45° C. Phases of each of the three samples were separated by centrifugation. Thereafter the oil phase was mixed with 100 ml of a 100 mmol/l solution in water of again either arginine or L-2-amino-3-guanidinopropionic acid, or L-canavanine used in the first step for 30 minutes at room temperature and phases were separated preferably by centrifugation. Thereafter the TAN of the oil phase was determined.

Results: The TAN was reduced in all three samples from 1.8 mg KOH/g to 0.16-0.3 mg KOH/g by the aqueous extraction with the solubilizing compounds.

Conclusion: The TAN of crude oil can be reduced by the solubilizing compounds. Since naphthenic acid prevails in crude oils, a significant reduction is possible.

Example 8

Investigation on the Stability of Oils in the Presence of Arginine and Other Solubilizing Compounds Refined sun flower oil was mixed with arginine solutions varying the concentrations and the duration. The solutions had concentrations of 100, 200, 300, and 500 mmol arginine, histidine, H-Cit-OH citrullin, N-ω-hydroxy-L-norarginine, and L-NIL. They were added in a 1:1 volume ratio. All solutions were vigorously stirred for 60 minutes, and then allowed to separate by sedimentation. One sample for each concentration was analysed after 3 hours, another after 7 days and yet another after 14 days. The fatty acid concentrations were determined as described in example 2. At concentrations of 100 and 200 mmol arginine the concentration of fatty acids were the same in all samples. At a concentration of 300 and 500 mmol there was an insignificant rise of fatty acid concentrations depending on the arginine concentration and the duration of exposure.

Conclusion: Arginine and other solubilizing compounds do not hydrolyse triglycerides at low or moderate concentrations. However, at higher concentrations hydrolysis might occur to a small extent.

Example 9

Investigation of the Capacity of the Solubilizing Compounds to Solve and Extract Carboxylic Acids from Oil During Fuel Production Biodiesel production relies on the hydrolysis of esterified carboxylic acids. Most commonly, hydrolysis is accomplished by hydrolases. However, these enzymes are inhibited by their reaction products. Therefore it is necessary to remove glycerin and carboxylic acids from the active center of the enzymes.

The dialysis apparatus of example 1 was used to test the feasibility and effectiveness of a continuous removal of fatty acids while performing hydrolysis of triglycerides from soy oil. Lipase (Novozyme 435) was immobilized according to the method of Lee (Lipase Immobilization on Silica Gel Using a Cross-linking Method, D H Lee, C H Park, J M Yeo, and S W Kim, J. Ind. Eng. Chem., Vol. 12, No. 5, (2006) 777-782). 150 ml refined soy oil and 50 ml of a either arginine, H-homoarginine-OH, or polyhexanide solution (100 mmol/l) were vigorously stirred and filled into the reaction chamber. The circulation system constantly circulated the emulsion at a speed that did not allow for phase separation. A PTFE filter with an exclusion size of 0.4 μm was mounted in the funnel-shaped outlet of the donor/reaction chamber in order to retain silica beads in the chamber while circulating the reaction solution. The acceptor chamber and the circulation system were filled with a 200 mmol/l solution of the respective compound. A PTFE separation membrane mounted between the reaction/donor and the acceptor chambers was used. DC was applied between the reaction chamber and the acceptor chamber during the hydrolyzing process, as in example 1. The solution in the acceptor chamber was continuously circulated and samples were taken every 10 minutes. The process was stopped after 30 minutes. 82% of the calculated fatty acid content of the triglycerides subjected to hydrolysis was present in the acceptor chamber. The solution of the acceptor chamber was separated and acidified with HCl to a pH of 4. Fatty acids were separated by n-hexane extraction. The separated hexane phase (10 ml) was mixed with 2 ml methanol. Novozyme 435 immoblilized on silica as described before was added. The esterification reaction was stopped after 30 minutes by filtration of the solution. The solution was vigorously stirred with a 50 mmol/l solution of the solubilizing substance used in the previous step. The organic phase was separated after phase separation and forwarded to a rotary evaporator to destill residual methanol and hexane.

Results: There was a quick rise in fatty acids concentration in, the acceptor solutions up to a plateau. No mono-, di-, or triglycerides or glycerin were found in the acceptor solutions. Fatty acids that had passed to the acceptor chamber could be purified from water soluble anions that had passed also by acidification and solvent extraction. The purified fatty acids were esterified in a non-aqueous medium by immobilized esterases. Not converted fatty acids were removed by an aqueous extraction with the solubilizing compounds. Evaporation of the alcohol and the solvent resulted in a highly purified solution of fatty acid methylester with a purity of >98%.

Conclusions: Hydrolysis of esterified fatty acids in an arginine solution is feasible, thus improving the convection of free fatty acids and thereby the process conditions. Hydrolyzed fatty acids can be further purified by solutions of the solubilizing compounds and conducted to a non-aqueous reaction medium for methylesterification (i.e. formation of a methyl ester). Furthermore, the non-reactive carboxylic acids can be removed in a final purification step using an aqueous solution of solubilizing compounds. Highly purified fatty acid methyl esters were produced after solvent evaporation without need for distillative separation of the fatty acid methyl esters.

Example 10

Investigation of the Capacity of Solubilizing Compounds to Solve Poorly Solvable Substances in Aqueous Solutions Many reaction substrates or reaction components have to be present in an aqueous medium in a non-complexed form, especially of biological systems. Nanoemulsification of substances improved their accessibility to biological transport mechanisms and reactions. However, many amphiphilic carrier systems exhibit biological toxicity or low bio-compatibility. Many of the solubilizing compounds are biocompatible. Therefore the emulsifying capacity of micro- or nanoemulsions of these compounds and carboxylic acids were investigated in poorly dissolvable substances (mg soluble in water) such as tetraphenylporphyrin (2 mg/l), sudan red (unsoluble), azoxystrobin (6.7 mg/l), co-phthalocyanine (unsoluble), chlorpropham (110 mg/l).

The investigated substanzes were first dissolved in an organic solvent: tetraphenylporphyrin in dichlormethan (50 mg/ml), Sudan red in acetone (2 mg/nril), azoxystrobin in toluol (50 mg/ml), co-phthalocyanine in acetonitril (2 mg/ml), chlorpropham in ethanol (50 mg/ml).

Nanoemulsions (50 ml) of oleic acid (50 mmol/l) and arginine (80 mmol), linoleic acid (50 mmol) and L-2-Amino-3-guanidinopropionic acid (100 mmol), and 12-hydroxy-9-octadecen acid (50 mg) and Nw-nitro-L-arginine (130 mmol) were dissolved in the organic medium containing the completely solubilized substances. The mixture was vigorously stirred. The organic solvent was evaporated while slowly stirring at room temperature or temperatures up to 50° C. The respective nanoemulsions were added until the solution became transparent or up to a volume of 100 ml. The solutions were analyzed for transparency and residual solids immediately and after 24 hrs.

Results: The investigated poorly water-soluble substances could be emulsified in aqueous media due to nanoemulgations after pre-solving in an appropriate organic solvent. Solvent-free nanoemulsified substances gave transparent emulsions without residual solid formation.

Conclusion: Micro- and nanoemulsions of solubilizing compounds and carboxylic acids can establish aqueous micro- or nanoemulsification of pooly water-soluble substances, yielding a biocompatible transport or carrier system for those substances in aqueous media.

Example 11

Investigation of Micro- or Nanoemulsification of Carboxylic Acids to Enable Alternative Chemical Reactions Hydrophobic carboxylic acids need to be dissolved in solvents for enabling many chemical reactions, like peroxydation or poymerization. Since many of those reactions can be performed in aqueous media, solvent-free procedures would be advantageous. Nanoemulgated molecules bring reactants close enough to react. Whether carboxylic acids nanoemulgated with arginine or other solubilizing substances can be used to enable chemical reactions usually performed in organic solvents was tested in two experiments.

To prove the capability of microemulsified carboxylic acids to react with peroxides by enzymatic esterification, 200 mmol 2-ethylhexanoic acid and 4-guanidinobutyric acid (1.5 mol equivalents) were dissolved in a mixture of water and THF at room temperature. Tert. butylhydroperoxide (200 mmol/l) was added and gently stirred. The solution was heated to 45° C. and a suspension of 40 mg Lipase PS was added in order to allow for a condensation reaction to tert.-butylperoxo-2-ethylhexanoate. The reaction was terminated after 1 h. The turnover rate was calculated by the peroxide fraction still present, as calculated by iodometric analysis. Repeated investigations yield a turnover rate of 65-72%. Experiments were repeated with agmantin and 6-guanidinohexanoic acid. The respective turn over rates ranged between 55-78%.

A nanoemulsion of 50 mmol/l perilla acid and 60 mmol/l arginine in water/THF (9:1 vol:vol) was mixed with 2. eq. m-CPBA in 3 aliquots at 25° C. over 3 h, and stirred for further 12 h. The reaction mixture was acidified to a pH of 4, extracted 3 times with $CHCl_3$. The organic phase was dried over $Na_2SO_4$, evaporated to 10 ml and a GC was measured. Yield by GC 65%. This procedure was also applied to geranium acid, citronella acid, oleylic acid, linolic acid using arginine, 1,1-dimethylbiguanide and, N-ω-hydroxy-L-arginine as solubilizing compounds. The yield ranged between 45-85%.

Conclusion: Nanoemulsified carboxylic acids using the inventive solubilizing substances enable chemical reactions in aqueous media without need of a solvent.

Example 12

Investigation of the Solubility of Various Carboxylic Acids in an Aqueous Medium by Arginine and Other Solubilizing Compounds Several solubilizing compounds were tested in aqueous medium for their potential to solubilize a reference fatty acid, namely oleic acid.

At the beginning the influence of the pH on the solubility of oleic acid in aqueous medium was tested. These tests were conducted in order to exclude the possibility that the observed solubility of oleic acid was due to pH changes and not primarily because of the interaction of functional groups.

The tests showed that there is no interaction between oleic acid and the solution in a pH range of 9-12 at room temperature. Starting at pH 13 oleic acid begins to dissolve. At pH 14 the addition of oleic acid led to the formation of a solid precipitate.

In the following tests oleic acid was mixed with the test substances in $H_2O$, Subsequently, log P and pH were measured and the solubility of the test substance in $H_2O$ was estimated together with an estimation of the interaction between oleic acid and the test substance according to the scheme shown below.

Solutions of the solubilizing compounds in water were prepared in a concentration of 6 to 600 mmol/l, and preferably about 60 mmol/l. To the aqueous solutions of the solubilizing compounds 0.833 mol equivalents of oleic acid or a respective carboxylic acid were added and mixed. The solutions were rested for 1 h and pH was measured. In case of incomplete dissolution and a pH below 7 a 1M NaOH solution was added dropwise until turbidity resolved. Then the mixtures were stirred or shaken. In order to assess the stability of the obtained micro or nanoemulsion, the solution were heated for 1 hour to 60° C. and cooled to room temperature. An other part of the clear solution was stored over night at 4° C. and then rewarmed to room temperature. Thereafter solutions were analysed for solid formation, residual oil, viscosity, turbidity, and DLS measurements were performed.

In emulsions either micelles or vesicles are formed. Their size and volume can be heterogeneous. In micro- and nanoemulsions only view cluster of vesicles sizes may prevail. The respective distribution and their relative frequency can be measured by dynamic laser light scattering (DLS), that was carried out on those samples that displayed a micro- or nanoemulsifying solubilization behavior for oleic acid. For DLS measurements a Zetasizer Nano S from Malvern (USA) was used. All measurements were repeated three times undiluted, or 1:10 and 1:100 diluted by water. For the measurements the viscosity of water and the refractory index of water were used. It could be demonstrated that all solubilizing compounds used caused solubilization of lipophilic carboxylic acids in water.

The column "Solubilizing Compound" in Table A indicates the form of the solubilizing compound dissolved in water. If for instance "hydrochloride" is indicated, the hydrochloride salt was dissolved in water. However, at the pH used for solubilization of the carboxylic acid, the solubilizing compound may no longer be in the form of the hydrochloride salt. Thus the column "Solubilizing Compound" indicates the starting material and not the active form of the solubilizing compound which is able to emulsify the carboxylic acid in the aqueous medium.

Peak Maximum by Intensity: Size is directly determined from the measurement without a weighting of volume or particle number.

Peaks are presented corresponding to their percentage in the sample.

Ratio of peak maxima: Percentual distribution of particle sizes.

Estimation of Solubility:

X=Compound is completely dissolved (X)=Compound is partially dissolved ((X))=Compound is not dissolved (visual appearance) but there is a change in pH. Therefore it is assumed that at least a small part is dissolved.

—=insoluble

Estimation of the Interaction Between Oleic Acid and the Test Substance:

X=Interaction between oleic acid and the test substance (X)=Interaction between oleic acid and test substance. There is significantly less oleic acid than water in the solution. E=Emulsion S=Formation of a solid precipitate E, S=The solution becomes cloudy, followed by the formation of a solid precipitate n.d.=not determined

TABLE A

| Solubilizing Compound | Dissolved ($H_2O$) | log P | pH | Interaction with Oleic Acid | Mean Size by Intensity [nm] | Part [%] |
|---|---|---|---|---|---|---|
| Amino acids | | | | | | |
| L-2-Amino-3-guanidinopropionic acid hydrochloride | X | −3.8094 | 11.05 | X, E | 113 | 87.2 |
| L-Arginine | X | −3.517 | 10.20 | X, E | 145 | 99.0 |
| L-Lysine | X | −3.424 | 9.56 | X, E | 133 | 95.6 |
| L-NIL | X | −3.517 | 9.12 | X, E | 349 | 94.1 |
| H-Homoarg-OH | X | −4.264 | 8.66 | X, E | 107 | 68.5 |
| Histidine hydrochloride monohydrate | X | −4.367 | 9.30 | X, E | 647 | 81.9 |
| Arginine derivatives | | | | | | |
| N-ω-Nitro-L-arginine | X | −5.2386 | 11.95 | X, E | 85.5 | 46.7 |
| N-ω-Hydroxy-L-norarginine | X | −3.98584 | 9.51 | X, E, S | 325 | 93.9 |
| D-arginine methyl ester dihydrochloride | X | −2.1082 | 11.35 | X, S | n.d. | n.d. |
| N-ω-monomethyl-L-arginine acetate | X | −4.044 | 8.49 | X, E | n.d. | n.d. |
| NG,NG-Dimethylarginine dihydrochloride | X | −3.752 | 9.45 | X, E | 22.9 | 87.4 |
| D-(+)-Octopine | | −4.0096 | 6.70 | X, E | 435 | 94.7 |
| Argininosuccinic acid disodium salt hydrate | X | −2.50212 | 9.93 | X, E | 721 | 74.6 |
| L-Canavanine free base | X | −3.98584 | 8.67 | (X), S, E | n.d. | n.d. |
| | | | 9.04 | X, E | | |
| Guanidine carboxylic acid derivatives | | | | | | |
| Creatine | X | −0.8842 | 8.32 | (X), E | n.d. | n.d. |
| | | | 10.01 | (X), E | | |
| Guanidine acetic acid | ((X)) | −2.387 | 6.20 | (X), E/S | n.d. | n.d. |
| 3-Guanidinopropionic acid | X | −3.765 | 11.71 | X, E | 153 | 64.7 |
| 4-Guanidinobutyric acid | X | −3.443 | 10.41 | X, E | n.d. | n.d. |
| 4-(4,5-Dihydro-1H-imidazol-2-ylamino)-butyric acid | X | −1.601 | 8.63/11.5 | X, E | 627 | 58.9 |
| (S)-(−)-2-Guanidinoglutaric acid | X | −3.1378 | 10.15 | X, E | n.d. | n.d. |
| 6-Guanidinohexanoic acid | (X) | −3.604 | 9.01 | (X), E | n.d. | n.d. |
| 4-Guanidinobenzoic acid hydrochloride | (X) | 0.6036 | 11.19 | X, E | n.d. | n.d. |
| Guanidine derivatives | | | | | | |
| Guanidinehydrochloride | X | −1.03 | 12.71 | X, E | n.d. | n.d. |
| Sulfaguanidine | ((X)) | −1.242 | 8.25 | X, S | n.d. | n.d. |
| Agmatin sulfate | X | −1.811 | 10.53 | X, S | n.d. | n.d. |
| 1,3-Di-o-tolyl-guanidine | ((X)) | 3.008 | n.b. | X, S | 723 | 73.5 |
| Clothianidine | (X) | −2.02559 | 9.81 | X, E | 153 | 53.9 |
| N-Guanylurea sulfate salt hydrate | X | 3.541 | 8.93 | X, E | n.d. | n.d. |
| Cimetidine | ((X)) | 0.19022 | 9.54 | X, E | 239 | 67.2 |
| Biguanidine derivatives | | | | | | |
| 1-(o-Tolyl)biguanide | (X) | 1.414 | 11.53 | X, E | 850 | 95.5 |
| Chlorhexidine diacetate | (X) | 6.18 | 6.51 | X, S | n.d. | n.d. |
| Chlorhexidine diacetate | (X) | 6.18 | 9.58 | X, S | n.d. | n.d. |
| 1,1-Dimethylbiguanide hydrochloride (97%) | X | −1.633 | 9.20 | X, E | 106 | 89.4 |
| Proguanil hydrochloride | (X) | 2.532 | 7.66 | X, E | n.d. | n.d. |
| Polymers (** = log P values are calculated on basis of the monomer units) | | | | | | |
| Polyhexanide −5% (2300 bis 3100 MW) | X | 2.78** | 5.61 | X, S | n.d. | n.d. |
| Polyhexanide −5% (2300 bis 3100 MW) | X | 2.798** | 8.61 | X, S | n.d. | n.d. |
| Poly-L-arginine HCl (70.000-150.000 MW) | X | −1.32** | 11.37 | X, S | n.d. | n.d. |

TABLE A-continued

| Solubilizing Compound | Dissolved (H₂O) | log P | pH | Interaction with Oleic Acid | Mean Size by Intensity [nm] | Part [%] |
|---|---|---|---|---|---|---|
| Other compounds | | | | | | |
| Diminazene aceturate (basic) | X | 0.90535 | 8.07 | X, S, (E) | 426 | 60.7 |
| Comparative compound DL-N-Acetylhomocysteine thiolactone (basic) | X | −0.4908 | 10.70 | — | n.d. | n.d. |
| Melamine | (X) | −0.96075 | 8.25 | X, S | n.d. | n.d. |
| 4-(4,6-Diamino-2,2-dimethyl-2H-[1,3,5]triazine-1-yl | (X) | 0.2952 | 11.28 | X, E, S | n.d. | n.d. |
| Comparative compound Urea | X | −3 | 8.59 | RT: −60° C.: ((X)) | 341 | 96.3 |
| Imidazole | X | −0.67 | 9.50 | X, E/S | 244 | 84.6 |
| Methylimidazole | X | −0.43 | 8.90 | X, E/S | 224 | 96.7 |
| Di, tri, and tetrapeptides | | | | | | |
| Tyr-Arg (Kyotorphin acetate) | X | −4.0044 | 8.54 | X, E | n.d. | n.d. |
| Arg-Gln hydrochloride | X | −6.5634 | 8.15 | X, E | n.d. | n.d. |
| Gly-Arg | X | −5.0644 | 9.18 | X, E | n.d. | n.d. |
| Arg-Phe | X | −3.3374 | 8.39 | X, E/S | n.d. | n.d. |
| Arg-Glu | X | −7.9134 | 8.83 | X, E | 191 | 97.7 |
| Lys-Arq acetate | X | −5.0554 | 11.93 | X, E | 254 | 89.9 |
| His-Arg | X | −5.7384 | 8.39 | X, E/S | 265 | 69.0 |
| Arg-Gly-Asp (RGD) | X | −8.2394 | 6.04 | (X), E | n.d. | n.d. |
| Arq-Gly-Asp (RGD)-basic | X | −8.2394 | 8.25 | X, E | 220 | 96.9 |
| Arg-Phe-Ala acetate | X | −3.595 | 8.25 | X, E | 223 | 90.0 |
| Thr-Lys-Pro-Arq (Tuftsin) | X | −3.982 | 8.68 | X, E | 174 | 96.3 |
| Gly-Gly-Tyr-Arg | X | −6.77304 | 8.57 | X, E | n.d. | n.d. |
| Others | | | | | | |
| Comparative compound Aminophenylacetic acid | (X) | 0.73 | 9.23 | ((X)) | n.d. | n.d. |
| Comparative compound L-Glutamin | (X) | −2.05 | 8.37 | ((X)) | n.d. | n.d. |
| Comparative compound Gly-Phe | X | −0.65 | 7.25 | ((X)) | 834 | 86.3 |
| Comparative compound 4-Aminobutyric acid | X | −0.82 | 8.57 | ((X)) | n.d. | n.d. |
| Gly-His | X | −2.42 | 12.1 | X, E | n.d. | n.d. |

The following solubilizing compounds (A) to (T) L-arginine (A), L-2-amino-3-guanidinopropionic acid (B), L-NIL (C), N-ω-nitro-L-arginine (D), NG,NG-dimethylarginine (E), agmatin (F), 1,1-dimethylbiguanide (G), L-canavanine (H), argininosuccinic acid (I), octopine (J), nω-monomethyl-L-argenine (K), arginine methylester (L), N-ω-hydroxy-L-arginine (M), histidin (N), H-homoarginine-OH(O), L-2-amino-3-guanidinopropionic (P), 6-guanidinohexanoic acid (Q), N-ω-hydroxy-L-norarginine (R), 4-guanidinobenzoic acid (S) and polyhexanide (T) were each used to solubilize the following carboxylic acids (I) to ( ):

hexadecaoic acid (I), eicosanoic acid (II), stearic acid (III), docosapentaenoic acid (IV), benzoic acid (V), caffeic acid (VI), terephthalic acid (VII), naphthenic acid (VIII), perfluorooctanoic acid (IX), eicosapentaenoic acid (20:5) (X), linolenic acid (18:3) (XI), and docosapentaenoic acid (22:5) (XII).

All carboxylic acids could be solibilized with the respective solibilization compound used in 1.5 mol equivalents at pH values between 8 and 10 as shown in Table B below:

TABLE B

| | (I) | (II) | (III) | (IV) | (V) | (VI) | (VII) | (VIII) | (IX) | (X) | (XI) | (XII) |
|---|---|---|---|---|---|---|---|---|---|---|---|---|
| (A) | X | X | X | X | (X) | X | X | X | X | X | X | X |
| (B) | X | X | (X) | X | X | X | X | X | X | X | X | X |
| (C) | X | X | X | (X) | X | X | X | X | X | X | X | X |
| (D) | X | X | X | X | X | X | X | X | X | X | X | X |
| (E) | X | X | X | X | X | X | X | X | X | X | X | X |
| (F) | X | X | X | X | X | X | X | X | X | X | X | X |
| (G) | X | X | X | X | X | X | X | X | X | X | X | X |
| (H) | X | X | X | X | X | X | X | X | X | X | X | X |
| (I) | X | X | X | X | X | X | X | X | X | X | X | X |
| (J) | X | X | X | X | X | X | X | X | X | X | X | X |
| (K) | X | X | X | X | X | X | X | X | X | X | X | X |
| (L) | X | X | X | X | X | X | X | X | X | X | X | X |
| (M) | X | X | X | X | X | X | (X) | X | X | X | X | X |
| (N) | X | X | X | (X) | X | X | X | X | X | X | X | X |
| (O) | X | X | X | X | X | X | X | X | X | X | X | X |

TABLE B-continued

|     | (I) | (II) | (III) | (IV) | (V) | (VI) | (VII) | (VIII) | (IX) | (X) | (XI) | (XII) |
|-----|-----|------|-------|------|-----|------|-------|--------|------|-----|------|-------|
| (P) | X   | X    | X     | X    | X   | X    | X     | X      | X    | X   | X    | X     |
| (Q) | X   | X    | X     | X    | X   | X    | X     | X      | X    | (X) | X    | X     |
| (R) | X   | X    | X     | X    | X   | X    | X     | X      | X    | X   | X    | X     |
| (S) | X   | X    | X     | X    | X   | X    | X     | X      | X    | X   | X    | X     |
| (T) | X   | X    | X     | X    | X   | X    | X     | X      | X    | X   | X    | X     |

X: Compound completely dissolved
(X): Compound partly dissolved

The invention claimed is:

1. The method for solubilising and separating carboxylic acids with a solubilizing compound from aqueous or organic solutions, emulsions, suspensions arising in medical therapy, medical analytics, food analytics, food processing, oil processing, oil analytics, fuel processing, modulation of chemical or physico-chemical reactions, solubilization of poorly solvable molecules, analytics in pharmaceutical or chemical industry or science, removal of carboxylic acids from sewage from private, commercial or industrial cleanings, removal of carboxylic acids from bioreactor processes, organogelation or nanoemulsification of carboxylic acids, wherein said solubilizing compound contains at least one amidino group and/or at least one guanidino group and wherein the solubilizing compound has a partition coefficient between n-octanol and water of $K_{OW} < 6.30$, and wherein the method comprises the following steps:
   i) providing the solution or emulsion or suspension containing the carboxylic acids;
   ii) adding of at least equimolar amounts of at least one solubilizing compound;
   iii) separating the solubilized carboxylic acids from the solution or emulsion or suspension by phase separation, filtration, nanofiltration, dialysis, absorption, complexation, electrophoresis, evaporation, distillation and/or extraction.

2. The method according to claim 1, wherein step iii) is achieved by means of one of the following separation methods or a combination thereof:
   passing the carboxylic acids separately or together with the at least one solubilizing compound through a separation membrane or a tube or hollow capillary assembly by applying a concentration gradient, a thermic gradient, a physico-chemical gradient, a pneumatic gradient, an electric gradient or a combination thereof; or
   performing phase separation by combining two or more media building phase separations; or
   passing the carboxylic acids together with the at least one solubilizing compound through a phase separation interface that allows the passage of said carboxylic acids and said at least one solubilizing compound by applying a concentration gradient, a thermic gradient, a physico-chemical gradient, a pneumatic gradient, an electric gradient or a combination thereof, wherein the phase separation interface consists of a gel, an organogel or a solid material or a combination thereof; or
   filtrating the carboxylic acids by using at least one solubilizing compound; or
   nanofiltrating the carboxylic acids by using at least one solubilizing compound; or
   dialyzing the carboxylic acids by using at least one solubilizing compound; or
   adsorbing the carboxylic acids by using at least one solubilizing compound; or
   complexing the carboxylic acids by using at least one solubilizing compound; or
   distilling the carboxylic acids by using at least one solubilizing compound; or
   separating the carboxylic acids by using at least one solubilizing compound by supercritical fluid extraction.

3. The method according to claim 1, comprising the following steps:
   a) preparing said solution by reducing ionic strength by means of complexation, adsorbtion, separation or dialysis of bound and unbound cations and anions;
   b) adjusting the pH of the solution by means of adding an acid or a base;
   c1) adjusting the molarity of the solubilizing compound to be in the range of 1:10 to 20:1 compared to the estimated concentration of the carboxylic acids to be solubilized; and
   d) adding said solubilizing compound in a solid form or in a solution to said carboxylic acid-containing aqueous or organic solution for generating a micro- or nanoemulsion;
   optionally comprising any of the steps
   a1) liberation of carboxylic acids bound by complexation or covalent binding
   c2) If the solubilizing compound is administered in a solution, adjusting the pH of said solution in order to optimize compatibility and reaction conditions with the carboxylic acids to be solubilized by means of acidification or alkanisation;
   e) adding esterases, hydrolases or a complex builder;
   f) adding water and/or a cosolvent to the solution; and/or
   g) optimizing reaction conditions by means of heating and/or mixing the solution, thereby generating an improved micro- or nano-emulsion.

4. The method according to claim 3 comprising additionally the steps after step g):
   g2) conducting the reactive solution from a first chamber to a second chamber through a separation panel using nanofiltration technique by applying a concentration gradient, a chemical gradient, a pneumatic gradient, an electric gradient or a combination thereof;
   optionally comprising the steps
   h) removing the associates of carboxylic acid and solubilizing compound from the filtrated solution through convection of an acceptor solution being led through an inlet into said second chamber and allowed to flow off through an outlet of said second chamber; and
   i) removing the purified solution from said second chamber through a further outlet.

5. The method according to claim 3, wherein the aqueous solution is the ex vivo blood sample of a subject from which blood micro- and/or nanoemulsions of fatty acids shall be removed, additionally comprising the following steps g1) to m) after step g):

g1) liberating esterified fatty acids in the blood of a subject by hydrolases immobilized on support materials inside said first chamber thus generating a micro- or nanoemulsion;
h) pumping the filtrated solution from said second chamber to a first chamber of a second dialyser;
i) conducting the carboxylic acid-containing solution from said first chamber of the second dialyser to a second chamber of the second dialyser through a second separation panel by applying a concentration gradient, a chemical gradient, a pneumatic gradient, an electric gradient or a combination thereof;
j) removing the associates of carboxylic acid and solubilizing compound passing through said second separation panel by means of a tertiary circulation;
k) pumping the carboxylic acid acceptor solution from an acceptor solution storage container into said second chamber of the second dialyser;
l) removing the loaden carboxylic acid acceptor solution into a waste container; and
m) reconducting the purified solution containing the solubilizing compound exiting said first chamber of the second dialyser to the inlet of said second chamber of the first dialyser.

6. The method according to claim 5, wherein the effect is reached by means of dialysis, hemofiltration, hemoperfusion, centrifuge-plasma-separation, plasma-apheresis, cascade-filtration and thermo-filtration.

7. The method according to claim 5, wherein the separation efficacy is increased by additional hydrolysis of esterified fatty acids, enhacement of lipolysis and/or the use of a central venous blood aspiration site for blood purification.

8. The method according to any one of claims 1, wherein the medical indication for applying said method is selected from diabetes mellitus, metabolic syndrome, overweight, obesity, arterial hypertension, hypertriglyceridemia, hypercholesterinemia, hyperuricemia, cellulitis, atherosclerosis, fatty liver, lipomatosis, ventricular premature beats, ventricular tachycardia and supraventricular fibrillation.

9. The method according to any one of claims 1, wherein the solution to be purified arises from plants, organisms, fossile materials, natural or synthethic reaction mixtures.

10. The method according to any one of claims 1, wherein the use of said solubilizing compound leads to micro- or nanoemulsion of said carboxylic acids and allows their separation by means of complexation, adsorption, absorption, diffusion, osmosis, dialysis, filtration, nanofiltration, distillation, fluid-fluid extraction or supercritical fluid extraction using a concentration gradient, a thermic gradient, an electrical gradient, a physico-chemical gradient or a combination thereof.

11. The method according to any one of claims 1, wherein the at least one solubilizing compound is added to an emulsion, solution or suspension containing the carboxylic acids in order to use said emulsion to liberate, decomplex, detach, react, aggregate, complex, coagulate, flocculate, sediment or separate the carboxylic acid-containing complexes.

12. The method according to claim 10, wherein micro- or nanoemulsions are used for diminishing a physico-chemical or chemical reaction, enabling, enhancing the up-take and transport of reaction products or components in biological or chemical reaction processes, detaching, solubilizing, liberating, convecting, transporting substances by vesicle up-take or enabling or enhancing the penetration of the emulsified carboxylic acids through hydrophilic or amphiphilic media or solids.

* * * * *